US011371101B2

(12) United States Patent
Haber et al.

(10) Patent No.: US 11,371,101 B2
(45) Date of Patent: Jun. 28, 2022

(54) DIGITAL ANALYSIS OF BLOOD SAMPLES TO DETERMINE EFFICACY OF CANCER THERAPIES FOR SPECIFIC CANCERS

(71) Applicant: The General Hospital Corporation, Boston, MA (US)

(72) Inventors: Daniel Haber, Chestnut Hill, MA (US); Shyamala Maheswaran, Lexington, MA (US); Tanya Todorova, Malden, MA (US); Mark Kalinich, Cambridge, MA (US); David Tomoaki Miyamoto, Wellesley, MA (US); Xin Hong, Medford, MA (US)

(73) Assignee: The General Hospital Corporation, Boston, MA (US)

( * ) Notice: Subject to any disclaimer, the term of this patent is extended or adjusted under 35 U.S.C. 154(b) by 14 days.

(21) Appl. No.: 16/344,557

(22) PCT Filed: Oct. 27, 2017

(86) PCT No.: PCT/US2017/058855
§ 371 (c)(1),
(2) Date: Apr. 24, 2019

(87) PCT Pub. No.: WO2018/081625
PCT Pub. Date: May 3, 2018

(65) Prior Publication Data
US 2019/0391134 A1 Dec. 26, 2019

Related U.S. Application Data

(60) Provisional application No. 62/413,952, filed on Oct. 27, 2016.

(51) Int. Cl.
*C12Q 1/6886* (2018.01)

(52) U.S. Cl.
CPC ..... *C12Q 1/6886* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,767,512 | B1 | 7/2004 | Lurz et al. |
| 7,074,367 | B2 | 7/2006 | Lurz et al. |
| 8,535,889 | B2 | 9/2013 | Larson et al. |
| 8,841,071 | B2 | 9/2014 | Link |
| 9,068,181 | B2 | 6/2015 | Edd et al. |
| 9,074,242 | B2 | 7/2015 | Larson et al. |
| 2003/0064385 | A1 | 4/2003 | Dressman et al. |
| 2003/0073623 | A1 | 4/2003 | Drmanac et al. |
| 2003/0143539 | A1 | 7/2003 | Bertucci et al. |
| 2006/0275794 | A1 | 12/2006 | Carrino et al. |
| 2007/0021597 | A1 | 1/2007 | Edwards et al. |
| 2007/0083334 | A1 | 4/2007 | Mintz et al. |
| 2008/0050393 | A1 | 2/2008 | Tang et al. |
| 2009/0275486 | A1 | 11/2009 | Kurn et al. |
| 2010/0162416 | A1 | 6/2010 | Krtolica |
| 2011/0059556 | A1 | 3/2011 | Strey et al. |
| 2012/0015835 | A1 | 1/2012 | Fuchs et al. |
| 2012/0252015 | A1 | 10/2012 | Hindson et al. |
| 2014/0303005 | A1 | 10/2014 | Samuels et al. |
| 2015/0168413 | A1 | 6/2015 | Haber et al. |
| 2015/0233927 | A1 | 8/2015 | Giannakakou et al. |
| 2015/0240314 | A1 | 8/2015 | Danila et al. |
| 2015/0301055 | A1 | 10/2015 | Spetzler |
| 2018/0057899 | A1 | 3/2018 | Haber |
| 2021/0189501 | A1 | 6/2021 | Haber et al. |

FOREIGN PATENT DOCUMENTS

| | | |
|---|---|---|
| JP | 2005-512510 A | 5/2005 |
| JP | 2014-507160 A | 3/2014 |
| JP | 2014-532409 | 12/2014 |
| JP | 2016-528252 A | 9/2016 |
| WO | WO 2009/051734 | 4/2009 |
| WO | WO 2011/112903 | 9/2011 |
| WO | WO 2012/115885 | 8/2012 |
| WO | WO 2014/165762 | 10/2014 |
| WO | WO 2014/028378 | 2/2015 |
| WO | WO 2015/023710 | 2/2015 |
| WO | WO 2015/058206 | 4/2015 |
| WO | WO 2016/145308 | 9/2016 |
| WO | WO 2016/154600 | 9/2016 |

OTHER PUBLICATIONS

Wang et al. J Molecular Diagnostics. Sep. 2015. 17(5): 515-520 (Year: 2015).*
Pouladi, N. "Dissecting the Heterogeneity of Breast Tumor Subtypes." Thesis. 2014, UMI Dissertation Publishing, UMI 3634164, ProQuest LLC (Year: 2014).*
EP Extended European Search Report in EP Appln. No. 17865612, dated May 27, 2020, 9 pages.
IL Office Action in Appln. No. IL254639, dated May 19, 2020, 4 pages (with English abstract).
Lingeng et al., "Circulating tumor cell clusters-associated gene plakoglobin and breast cancer survival," Breast Cancer Research and Treatment, May 2015, 151:491-500.
Nolan et al., "Quantification of mRNA using real-time RT-PCR," Nature Protocols, 2006, 1(3):1559-1582.

(Continued)

*Primary Examiner* — Carla J Myers
(74) *Attorney, Agent, or Firm* — Fish & Richardson P.C.

(57) ABSTRACT

This disclosure relates to new assay methods for analysis of RNA, e.g., from circulating tumor cells (CTCs), tumor-specific exosomes, or tumor-specific cell-free RNA, in a subject's blood sample to determine an expression level of one or more lineage markers in the blood sample, wherein the expression level of a specific one or more lineage markers is predictive of progression-free survival and overall survival for a specific anti-cancer treatment regimen in that subject.

15 Claims, 16 Drawing Sheets

Specification includes a Sequence Listing.

(56) References Cited

OTHER PUBLICATIONS

Pomerantz et al., "The androgen receptor cistrome is extensively reprogrammed in human prostate tumorigenesis," Nature Genetics, Nov. 2015, 47(11):1346-1351.
Rozen et al., "Primer3 on the WWW for General Users and for Biologist Programmers," Bioinformatics Methods and Protocols. Humana Press, Totowa, NJ, 2000, 365-386.
Untergasser et al., "Primer 3Plusan enhanced web interface to Primer3," Nucleic Acids Research, 2007, 35(2):W71-W74.
Yu et al., "Ex vivo culture of circulating breast tumor cells for individualized testing of dmg susceptibility," Science, Jul. 2014, 345(6193):216-220.
Aceto et al., Circulating tumor cell clusters are oligoclonal precursors of breast cancer metastasis, Cell, 2014, 158:1110-1122.
Agresti et al., "Ultrahigh-Throughput Screening in Drop-Based Microfluidics for Directed Evolution," PNAS, 2010, 107:4004-9.
Baret, "Surfactants in droplet-based microfluidics," Lab on a Chip, 2012, 12: 422-433.
Barretina et al., The Cancer Cell Line Encyclopedia enables predictive modelling of anticancer drug sensitivity, Nature, 2012, 483:603-607.
Chiappini, "Circulating tumor cells measurements in hepatocellular carcinoma," International Journal of Hepatology, May 28, 2012, 2012, 16 pages.
Droplet Digital PCR: QX100 System, Bio-Rad Laboratories, Inc., Apr. 2014, 8 pages.
Eastburn et al., "Identification and genetic analysis of cancer cells with PCR-activated cell sorting," Nucleic Acids Research, 2014, 42: e128.
EP European Search Report and Written Opinion in Application No. 16769818.2, dated Jul. 31, 2018, 10 pages.
EP Office Action in Appln. No. 20160769818, dated Jun. 27, 2019, 7 pages.
EP Office Action in European Appln. No. 17865612.0, dated Jun. 11, 2019, 3 pages.
GEO Accession No. GSE24759, "Densely interconnected transcriptional circuits control cell states in human hematopoiesis," Mar. 22, 2017, 2 pages.
GEO Accession No. GSE30811, "SuperSAGE evidence for CD14++ CD16+ monocytes as a third monocyte subset," May 15, 2019, 2 pages.
GEO Accession No. GSE48060, "Transcriptome from circulating cells suggests dysregulated pathways associated with long-term recurrent events following first-time myocardial infarction," Mar. 25, 2019, 2 pages.
GEO Accession No. GSE51808, "Systems biological analysis of immunity to dengue," July 26, 2019, 2 pages.
GEO Accession No. GSE51827, "Circulating Tumor Cell Clusters are Oligoclonal Precursors of Breast Cancer Metastasis," May 15, 2019, 2 pages.
GEO Accession No. GSE54514, "Whole blood transcriptome of survivors and nonsurvivors of sepsis," Aug. 16, 2018, 2 pages.
GEO Accession No. GSE60407, "Human Pancreatic CTCs Express the ECM Protein SPARC," May 15, 2019, 2 pages.
GEO Accession No. GSE67980, "RNA-Seq of Single Prostate CTCs Implicates Non-Canonical Wnt Signaling in Antiandrogen Resistance," May 15, 2019, 2 pages.
Hayes et al. (Clinical Cancer Research 12.14 (2006): 4218-4224.). (Year: 2006).
Heitzer et al., "Digital circulating tumor cell analyses for prostate cancer precision oncology," Cancer Discovery, Mar. 1, 2018, 8(3):269-71.
Holtze et al., "Biocompatible surfactants for water-in-fluorocarbon emulsions," Lab on a Chip, 2008, 8: 1632-1639.
Hong et al., "Molecular signatures of circulating melanoma cells for monitoring early response to immune checkpoint therapy," Proceedings of the National Academy of Sciences, Mar. 6, 2018, 115(10):2467-72.
IL Office Action in Appln. No. IL254639, dated Feb. 17, 2019, 7 pages.
International Preliminary Report on Patentability in International Application No. PCT/US2016/024367, dated Aug. 22, 2016, 16 pages.
JP Office Action in Japanese Appln. No. 2017-549623, dated Jan. 7, 2020, 9 pages.
Kalinich et al., "An RNA-based signature enables high specificity detection of circulating tumor cells in hepatocellular carcinoma," Proceedings of the National Academy of Sciences, Jan. 31, 2017, 114(5):1123-8.
Kim et al., "Identification of novel markers that outperform EpCAM in quantifying circulating tumor cells," Cellular Oncology, Aug. 1, 2014, 37(4):235-43.
Kim et al., "Identification of novel markers that outperform EpCAM in quantifying circulating tumor cells," Supp. Table 3, Cellular Oncology, Aug. 1, 2014, 37(4), 2 pages.
Kwan et al., "A digital RNA signature of circulating tumor cells predicting early therapeutic response in localized and metastatic breast cancer," Cancer Discovery, Oct. 1, 2018, 8(10):1286-99.
Lowe et al., "A computer program for selection of oligonucleotide primers for polymerase chain reactions," Nucleic Acids Research, Apr. 11, 1990, 18(7):1757-61.
Man et al., "Newly identified biomarkers for detecting circulating tumor cells in lung adenocarcinoma," The Tohoku Journal of Experimental Medicine, 2014, 234(1):29-40.
Miyamoto et al., "An RNA-based digital circulating tumor cell signature is predictive of drug response and early dissemination in prostate cancer," Cancer Discovery, Mar. 1, 2018, 8(3):288-303.
Miyamoto et al., RNA-Seq of single prostate CTCs implicates noncanonical Wnt signaling in antiandrogen resistance, Science, 2015, 349:1351-1356.
Ozkumur et al., Inertial Focusing for Tumor Antigen-Dependent and -Independent Sorting of Rare Circulating Tumor Cells, Science Translational Medicine, Apr. 2013, 5: 179ra47, 11 pages.
PCT International Preliminary Report on Patentability for International Appln. No. PCT/US2017/058855, dated Apr. 30, 2019, 11 pages.
PCT International Preliminary Report on Patentability in International Application No. PCT/US2016/024367, dated Sep. 26, 2017.
PCT International Search Report and Written Opinion in International Appln. No. PCT/US2017/058855, dated Apr. 26, 2018, 23 pages.
Plaks et al., "Circulating tumor cells," Science, Sep. 13, 2013, 541(6151):1186-8.
Ramsköld et al, "Full-length mRNA-Seq from single-cell levels of RNA and individual circulating tumor cells," Nature biotechnology, Aug. 2012, 30(8):777.
Ramsköld et al, "Full-length mRNA-Seq from single-cell levels of RNA and individual circulating tumor cells," Supp. Table 4, Nature biotechnology, Aug. 2012, 30(8), 3 pages.
Sequist et al., "The CTC-Chip: An Exciting New Tool to Detect Circulating Tumor Cells in Lung Cancer Patients," Journal of Thoracic Oncology, Mar. 2009, 4: 281-283.
Smirnov et al., "Global gene expression profiling of circulating tumor cells," Cancer Research, Jun. 15, 2005, 65(12):4993-7.
Smirnov et al., "Global gene expression profiling of circulating tumor cells," Supp. Table 2, Cancer Research, Jun. 15, 2005, 65(12), 3 pages.
Stott et al., "Isolation and Characterization of Circulating Tumor Cells from Patients with Localized and Metastatic Prostate Cancer," Science Translational Medicine, Mar. 2010, 2: 111-120.
Taly et al., "Detecting biomarkers with microdroplet technology," Trends in Molecular Medicine, Jul. 2012, 18: 405-416.
Ting et al., Single-Cell RNA Sequencing Identifies Extracellular Matrix Gene Expression by Pancreatic Circulating Tumor Cells, Cell Rep, 2014, 8:1905-1918.
Wang et al., "Gene expression markers in circulating tumor cells may predict bone metastasis and response to hormonal treatment in breast cancer," Molecular and Clinical Oncology, Nov. 1, 2013;1(6):1031-8.
AU Office Action in Australian Appln. No. 2016238253, dated May 27, 2021, 5 pages.

(56) References Cited

OTHER PUBLICATIONS

CN Office Action in Chinese Appln. No 201680029396, dated Jun. 9, 2021, 8 pages (with English translation).
CN Office Action in Chinese Appln. No. 201680029396, dated Feb. 10, 2021, 13 pages (with English translation).
CN Office Action in Chinese Appln. No. 201680029396, dated Jun. 28, 2020, 11 pages (with English language translation).
IN Office Action in Indian Appln. No. 201747037524, dated Jul. 24, 2020, 7 pages.
JP Office Action in Japanese Appln. No. 2017-549623, dated Sep. 29, 2020, 8 pages (with English translation).
Stott et al., "Supplementary Materials for Isolation and Characterization of Circulating Tumor Cells from Patients with Localized and Metastatic Prostate Cancer," Sci. Transl. Med., 2010, 12 pages.
JP Office Action in Japanese Appln. No. 2019-522657, dated Sep. 7, 2021, 8 pages (with English translation).
Extended European Search Report in European Appln. No. 21212237.8, dated Mar. 23, 2022, 13 pages.
Ma et al., "Droplet digital PCR based androgen receptor variant 7 (AR-V7) detection from prostate cancer patient blood biopsies," International Journal of Molecular Sciences, Aug. 2016, 17(8): 1264, 11 pages.
Qu et al., "Association of AR-V7 and Prostate-Specific Antigen RNA Levels in Blood with Efficacy of Abiraterone Acetate and Enzalutamide Treatment in Men with Prostate Cancer," Clinical Cancer Research, Aug. 2016, 23(3):726-734.
Todenhofer Tilman et al., "AR-V7 transcripts in whole blood RNA of patients with metastatic castration resistant prostate cancer correlate with repose to abiraterone acetate," Journal of Urology, Jul. 2016, 197(1):135-142.

\* cited by examiner

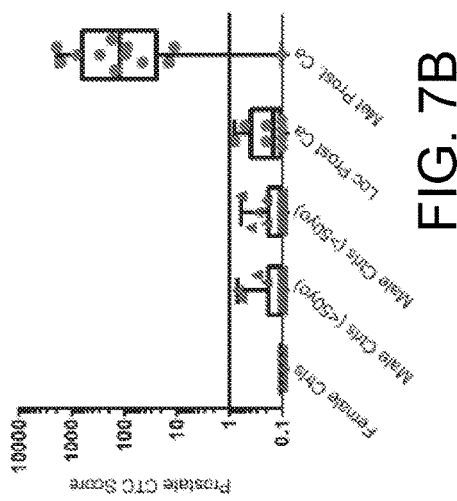
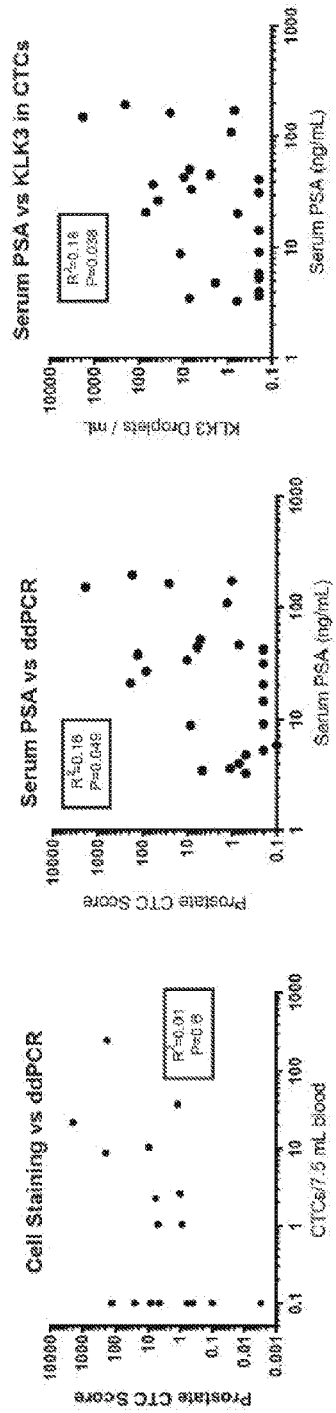
FIG. 7B
FIG. 7C
FIG. 7D
FIG. 7E

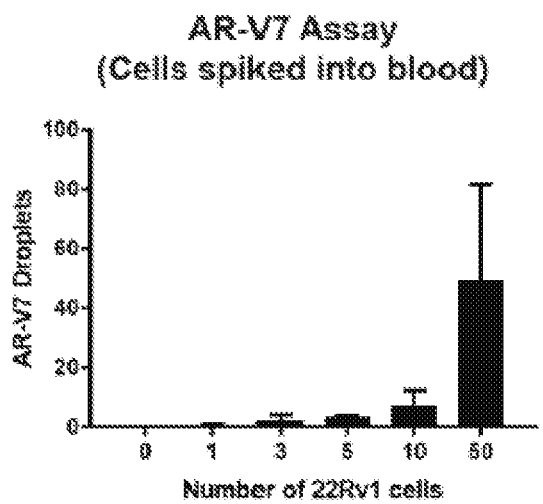
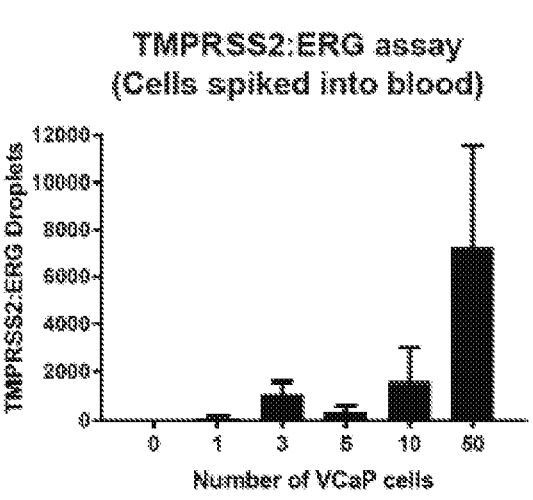
FIG. 8A  FIG. 8B
FIG. 8C  FIG. 8D

DIGITAL ANALYSIS OF BLOOD SAMPLES TO DETERMINE EFFICACY OF CANCER THERAPIES FOR SPECIFIC CANCERS

CROSS REFERENCE TO RELATED APPLICATIONS

This application is a 371 U.S. National Phase Application of PCT/US2017/058855, filed on Oct. 27, 2017, which claims priority from U.S. Provisional Application Ser. No. 62/413,952, filed on Oct. 27, 2016, which is incorporated herein by reference in its entirety.

TECHNICAL FIELD

This invention relates to sample analysis techniques, and more particularly to methods and systems for detecting and analyzing nucleic acids from cancer cells, e.g., in blood samples to determine which therapies would be most effective in a specific patient.

BACKGROUND

The ability to detect the presence of rare circulating tumor cells (CTCs), exosomes, and cell-free nucleic acids, such as cell-free deoxyribonucleic acid (DNA) or ribonucleic acid (RNA), using a simple blood test, or "liquid biopsy," has the potential to greatly enhance the monitoring of cancers, providing instant sampling of tumor cell numbers, genetic composition, and drug response parameters, without requiring invasive tumor biopsies. Thus, the detection of CTCs, exosomes, and cell-free DNA or RNA for early cancer detection has the potential to revolutionize the treatment of cancer, enabling the diagnosis of invasive cancer at a stage before it has metastasized, when curative treatment is expected.

However, CTCs, exosomes, and cell-free nucleic acids are very rare and/or small and/or are easily degraded, and thus identifying, visualizing, measuring, and scoring these rare components admixed with normal blood components remains a significant challenge, even after partial purification with known microfluidic devices or similar technologies. For example, per milliliter of whole blood, there are only 1-10 CTCs amongst more than 5 billion red blood cells (RBCs) and more than 5 million white blood cells (WBCs) (Plaks et al., "Cancer Circulating Tumor Cells," *Science*, 341:1186; 2013).

While exosomes are not that rare, they are only about 30-100 nm in diameter, making them difficult to isolate and detect in blood samples. Due to the complexity of body fluids such as blood, physical separation of exosomes from cells and similar-sized particles is challenging. Isolation of exosomes using differential ultracentrifugation and microfiltration or a gradient can improve purity. Single step isolation of extracellular vesicles by size-exclusion chromatography has been demonstrated to provide greater efficiency for recovering intact vesicles over centrifugation, although a size-based technique alone will generally not be able to distinguish exosomes from other vesicle types. To isolate a pure population of exosomes a combination of techniques is necessary, based on both physical (e.g. size, density) and biochemical parameters (e.g. presence/absence of certain proteins involved in their biogenesis). A key challenge to isolating tumor-derived exosomes is to differentiate them from exosomes produced by normal tissues.

When employing cell-free RNA, it is important to minimize release of cellular RNA following blood draw, because cell-free RNA is present at low quantities in the blood. Thus, blood samples require special handling and/or systems to avoid degradation or contamination with nucleic acids from cells, and to stabilize the cell-free RNA.

In addition, antibody staining of tumor cells is highly variable, due to high heterogeneity among cancer cells, even within an individual patient, as well as the poor physical condition of many tumor cells that circulate in the bloodstream, many of which have begun to undergo programmed cell death or anoikis. In addition, accurate scoring of antibody-stained tumor cells requires differentiation from large numbers of contaminating white blood cells, some of which bind to antibody reagents non-specifically. As such, only a subset of candidate tumor cells can be robustly identified by antibody staining, and as many as half of patients tested have no detectable cells, despite having widely metastatic cancer.

SUMMARY

The present disclosure relates to methods and uses to obtain the highest possible sensitivity of data relating to tumor-specific RNA, e.g., from rare CTCs, exosomes, and/or cell-free RNA, in standard blood samples to predict which cancer therapies may be most effective to treat a specific detected cancer in a given patient. In particular, the new methods do not need the CTCs and/or exosomes to be completely isolated from contaminating WBCs, and instead can reliably detect as few as one CTC or exosome in products containing, e.g., up to 10,000 WBCs or more. The new assay methods combine (1) an isolation system that can consistently obtain intact CTCs and exosomes with high quality RNA from blood with (2) a droplet-based digital polymerase chain reaction (PCR) assay focused on RNA markers of specific cancer lineages for each tumor type that are absent in blood of healthy patients. The new methods can be used to determine which therapeutic agents have the highest potential to effectively treat the specific cancer type found in each patient.

In general, the disclosure relates to methods for predicting the efficacy of specific therapeutic regimens, e.g., therapeutic agents, to treat specific cancers in a given subject or patient with ultra-high sensitivity and specificity. The new methods comprise or consist of obtaining tumor-specific RNA from a blood sample and determining which of a series of lineage markers are expressed in the RNA in the blood sample, wherein an expression level of or more specific lineage markers is predictive of progression-free survival and overall survival for a specific anti-cancer treatment regimen. For example, in some implementations, the methods can include or consist of isolating circulating tumor cells (CTCs) from a blood sample from the subject; converting CTC-derived RNA into cDNA; encapsulating the cDNA into individual droplets; amplifying the cDNA in each droplet in the presence of a reporter group configured to bind specifically to cDNA from CTCs and not to cDNA from other cells in the blood; and determining which of a series of lineage markers are expressed in the CTCs in the blood sample, wherein an expression level of a specific one or more lineage markers is predictive of progression-free survival, time to progression, overall survival, or other clinically relevant endpoints for a specific anti-cancer treatment regimen.

In some implementations, the potential efficacy of a specific anti-cancer treatment regimen for a specific cancer in the subject is determined by comparing the expression levels of one or more of the subject's specific lineage markers to a reference standard established for the specific anti-cancer treatment regimen for the specific cancer to determine whether the subject will be treated effectively with the specific anti-cancer treatment regimen. For example, in some implementations, the subject may have prostate cancer and if the subject's specific lineage markers assayed before treatment is begun include an elevated level of FOLH1 (PSMA) and HOXB13 above a background noise level as determined by evaluation of healthy donors without cancer, then the methods described herein predict that the patient will not improve if treated only with abiraterone (e.g., ZYTIGA®). In some implementations, such a subject is further prescribed a combination therapy of abiraterone and another anti-prostate cancer therapy.

In other implementations, the subject may have hormone receptor-positive ("HR+") breast cancer and if the subject's specific lineage markers assayed at three to four weeks after treatment with a drug targeting the estrogen-signaling pathway include an elevated level of one or more, e.g., one, two, three, four, five, or all six, of PIP, SERPINA3, AGR2, SCGB2A1, EFHD1, and WFDC2 genes above a background noise level determined by evaluation of healthy donors without cancer, then the methods described herein predict that the patient will not improve if treated only with a drug that targets the estrogen-signaling pathway. For example the drugs may be, e.g., ER inhibitors (e.g., tamoxifen), selective ER degraders (e.g., fulvestrant), and aromatase inhibitors (AI), which block the production of estrogen (e.g., anastrozole, letrozole, and exemestane). The results of the method may cause a healthcare provider to further prescribe for the subject a combination therapy of a drug targeting the estrogen-signaling pathway and another anti-breast cancer therapy.

In various implementations, the methods can include the use of microfluidic isolation of circulating tumor cells (CTCs), or exosomes or cell-free RNA, and digital detection of RNA derived from these components. In some embodiments, the RNA can be converted into cDNA and encapsulated into individual droplets for amplification in the presence of reporter groups that are configured to bind specifically to cDNA from CTCs (or other tumor RNA) and not to cDNA from other noncancerous cells.

The methods described herein can further include reducing a volume of the product before isolating RNA and/or removing contaminants from the cDNA-containing solution before encapsulating the cDNA molecules.

In various implementations of the new methods, generating cDNA molecules from the isolated RNA can include conducting reverse transcription (RT) polymerase chain reaction (PCR) of the isolated RNA molecules and/or amplifying cDNA molecules within each of the droplets can include conducting PCR in each droplet. In the new methods, encapsulating individual cDNA molecules and PCR reagents in individual droplets can include forming at least 1000 droplets of a non-aqueous liquid, such as one or more fluorocarbons, hydrofluorocarbons, mineral oils, silicone oils, and hydrocarbon oils and/or one or more surfactants. Each droplet can contain, on average, one target cDNA molecule obtained from a CTC. In some embodiments, the reporter groups can be or include a fluorescent label.

In various implementations, the methods described herein include using probes and primers in amplifying the cDNA molecules within each of the droplets that correspond to one or more genes selected from the list of cancer-selective genes in Table 1 herein. For example, the selected genes can include prostate cancer-selective genes, e.g., any one or more of AGR2, FOLH1, HOXB13, KLK2, KLK3, SCHLAP1, AMACR, AR variants, including AR-V7, UGT2B15, STEAP2, and TMPRSS2:ERG (as can be easily determined from Table 1). In another example, any one or more of ALDH1A3, CDH11, EGFR, FAT1, MET, PKP3, RND3, S100A2, and STEAP2 are selective for pancreatic cancer. Similar lists can be generated for the other types of cancers listed in Table 3.

In other examples, the selected genes include any one or more of the breast cancer-selective genes listed in Table 3. In other examples, the selected genes include genes selective for one or more of lung, liver, prostate, pancreatic, and melanoma cancer. For example, a multiplexed assay can include 2, 3, 4, 5, 6, 7, 8, 9, 10, 11, 12 or even all of the selected genes that are listed in Table 3 as being selective for a particular type of cancer, e.g., breast cancer, lung cancer, prostate cancer, pancreatic cancer, liver cancer, and melanoma. Typically, a group of primers and probes for 1, 2, 3, 4, 5, 6, 7, 8, 9, 10, 11, or 12 or more cancer-selective genes from Table 1 are used for a particular type of cancer. Other specific combinations of selected genes (markers for those genes) are described in the Examples below.

In the methods described herein, the CTCs can arise from metastatic or primary/localized cancers.

The disclosure also provides uses of the probes and primers related to one or more selected cancer genes listed in Table 3 for amplifying and detecting cDNA molecules obtained from circulating tumor cells (CTCs) in a blood sample, and for determining which of a series of lineage markers are expressed in the CTCs in the blood sample, wherein an expression level of a specific one or more lineage markers is predictive of progression-free survival and overall survival for a specific anti-cancer treatment regimen.

As used herein, the phrase "circulating tumor cells" (CTCs) refers to cancer cells derived from solid tumors (non-hematogenous cancers) that are present in very rare numbers in the blood stream of patients (e.g., about 1 CTC in about 10,000,000 WBCs in whole blood). CTCs can arise from both metastatic as well as primary/localized cancers.

As used herein, a "product" means a group of isolated rare cells and other contaminating blood cells, e.g., red blood cells, white blood cells (e.g., leukocytes), e.g., in some sort of liquid, e.g., a buffer, such as a pluronic buffer, that arise from processing in the methods described herein, e.g., using the systems described herein. A typical product may contain only about one to ten CTCs admixed with 500 to 2,500 or more WBCs, e.g., one to ten CTCs in a mixture of 1000 to 2000 WBCs. However, the limit of detection of the present methods can be about 1 CTC in 10,000 WBC. Thus, while the present methods can achieve a level of purity of about 1 CTC in 500 WBCs, the present methods do not require highly purified CTCs, as is required in some known methods of CTC analysis.

The polymerase chain reaction (PCR) is a process of amplification of known DNA fragments by serial annealing and re-annealing of small oligonucleotide primers, resulting in a detectable molecular signal.

Reverse Transcription (RT)-PCR refers to the use of reverse transcription to generate a complementary c-DNA molecule from an RNA template, thereby enabling the DNA polymerase chain reaction to operate on RNA. An important aspect of the new methods disclosed herein is the availability of high quality RNA from whole cell CTCs that are not lysed or treated in such a way that might destroy or degrade the RNA, or from exosomes or cell-free RNA.

As used herein, "positive droplets" are lipid-encapsulated molecules in which a PCR reaction performed with tagged primers allows visualization of the PCR amplified product. Thus, a droplet that contained a single template cDNA molecule of a particular targeted gene can become visible using fluorescence microscopy, while an "empty" or "negative" droplet is one that contains no targeted cDNA.

The new methods and systems provide numerous advantages and benefits. For example, the current methods and systems provide results that are far more accurate and robust than either of the prior known systems when used alone. By breaking down the signal from a single CTC or exosome into hundreds or thousands of brightly fluorescent droplets, each derived from a single cDNA molecule, the new digital-CTC assays enable dramatic signal amplification. Given the strict criteria in selecting and optimizing the biomarker genes described herein, the background signal from normal blood cells is negligible in d-CTC. Thus, d-CTC enables greatly amplified signal from patients with advanced cancer (nearly 100% of patients with prostate, lung, breast, and liver cancers). Not only is the fraction of patients with a positive score significantly increased, but also the high level of signal enables dynamic measurements as tumor load declines following cancer therapy, and enables accurate prediction of clinical outcomes of specific therapies even before the therapies are started.

In sum, this novel microfluidics platform provides a streamlined, ultrahigh-throughput, rapid (e.g., 3 hours per run), and extremely high sensitivity method of enriching, detecting, and analyzing CTCs in patient blood samples. The platform provides rich, clinically actionable information, including the prediction of clinical outcomes of specific cancer-directed therapies.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 7A-7D are a series of graphs showing the ddPCR expression signal for genes in metastatic patients and healthy donors.

FIG. 7A is a heatmap showing d-CTC assay signal for each gene in blood obtained from healthy donor controls, localized prostate cancer patients, and metastatic castration-resistant prostate cancer (mCRPC) patients.

FIG. 7B is graph showing the weighted prostate CTC score developed based on the relative signal to noise ratio of the ddPCR expression signal for each gene in metastatic patients relative to healthy donors.

FIGS. 7C, 7D, and 7E are graphs of relationships between CTC ddPCR signal and CTC staining signal, ddPCR CTC signal and serum PSA, and ddPCR CTC KLK3 signal and serum PSA, respectively.

FIGS. 8A-8F are a series of graphs and other results of analytical testing and validation of ddPCR expression assay for AR-V7 and TMPRSS2:ERG expression in prostate CTCs.

FIG. 8A is a bar graph of ddPCR signal for AV-7 for varying numbers of 22Rv1 cells micro-manipulated into healthy donor whole blood and processed using the CTC-iChip.

FIG. 8B is a bar graph of ddPCR signal for TMPRSS2:ERG for varying numbers of VCaP cells micro-manipulated into healthy donor whole blood and processed using the CTC-iChip.

FIG. 8C is a chart showing the results of ddPCR signal of metastatic prostate cancer patients having AR-V7 and/or TMPRSS2-ERG ddPCR signal.

FIG. 8D is a chart showing the results of ddPCR signal of healthy donors having AR-V7 and/or TMPRSS2-ERG ddPCR signal.

FIG. 8E is a concordance of ddPCR signal for TMPRSS2:ERG in prostate CTCs and matched archival FFPE specimens of prostate cancer biopsy or prostatectomy tissues from prostate cancer patients.

FIG. 8F is a concordance of ddPCR signal for AR-V7 in prostate CTCs and matched archival FFPE specimens of prostate cancer biopsy or prostatectomy tissues from prostate cancer patients.

FIG. 9A is a schematic of CTC draw time points in the prospective study of abiraterone in the first-line setting in patients with mCRPC.

FIG. 9B is a heatmap of digital CTC assay signal in patients at different time points of abiraterone treatment.

FIG. 10A is a set of Kaplan-Meier curves for radiographic progression-free survival (R-PFS) by AR-V7 status in CTCs at pretreatment (C1D1) and 12 weeks on treatment (C4D1).

FIG. 10B is a set of Kaplan-Meier curves for overall survival (OS) by AR-V7 status in CTCs at pretreatment (C1D1) and 12 weeks on treatment (C4D1).

FIG. 10C is a pair of Kaplan-Meier curves for radiographic progression-free survival (R-PFS) for HOXB13 in CTCs at pretreatment (C1D1) and 12 weeks on treatment (C4D1).

FIG. 10D is a pair of Kaplan-Meier curves for OS for HOXb13 in CTCs at pretreatment (C1D1) and 12 weeks on treatment (C4D1).

FIG. 10E is a set of Kaplan-Meier curves for R-PFS for FOLH1 in CTCs at pretreatment (C1D1) and 12 weeks on treatment (C4D1).

FIG. 10F is a series of Kaplan-Meier curves for OS for FOLH1 in CTCs at pretreatment (C1D1) and 12 weeks on treatment (C4D1).

FIG. 11A is a graphic representation of unsupervised clustering of marker expression at 3-4 weeks of treatment in HR+ patients receiving endocrine treatment. A set of markers (red) identifies a group of patients (blue) significantly enriched for progression within 120 days and poor survival (p-values show significance based on Fisher's exact test). ESR1 mutation status for each patient, established by either genotyping or ddPCR, is also indicated.

FIGS. 11B-1 and B-2 are a pair of graphs that show correlations between a metascore based on the expression of the 6 high risk genes and GSEA signatures associated with estrogen signaling (11B-1) and endocrine resistance (11B-2) across multiple publically available datasets are shown in red crosses. The dotted line on the right as 0.54 represents the median correlation across the multiple comparisons. Correlations with metascores based on 100 random sets of 6 genes are shown in blue circles.

FIGS. 11C-1 and 11C-2 are a pair of Kaplan-Meier curves of OS (11C-1) and TTP (11C-2) in HR+ patients receiving endocrine therapy based on RS score at 3-4 weeks on treatment. Groups were divided at 275 transcripts/ml; p-values based on log rank tests.

FIGS. 11D1 and 11D-2 are a pair of Kaplan-Meier curves depicting OS (left) and TTP (right) in HR+ patients receiving endocrine therapy based on presence of ESR1 mutations. p-values based on log rank tests.

DETAILED DESCRIPTION

Figures 1, 4:
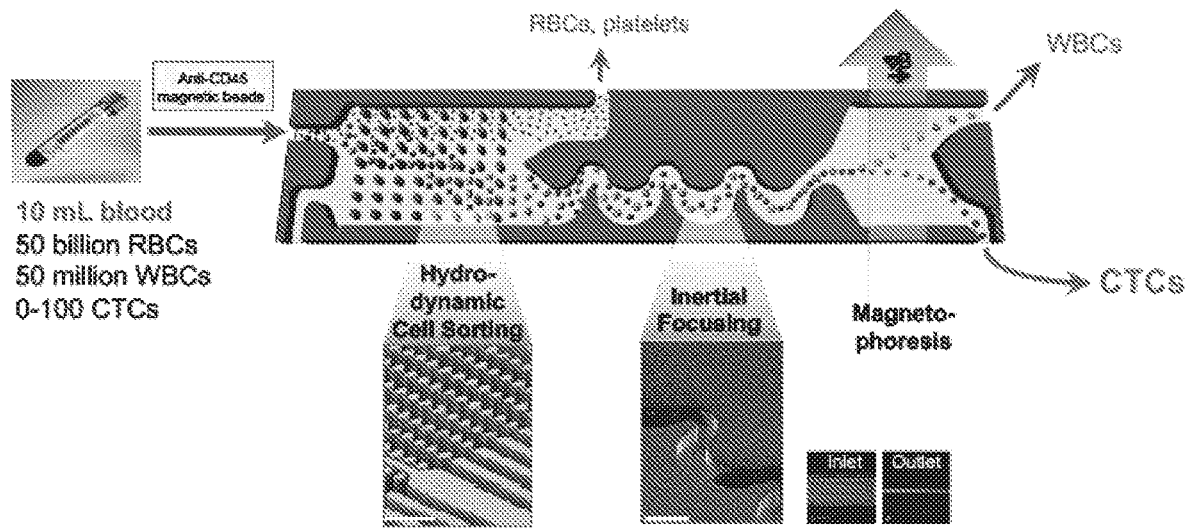
FIG. 1 is a schematic diagram of a microfluidic CTC isolation module (CTC-iChip).
FIG. 4 is chart showing the results of a multiplex prostate CTC assay that provides 4 lineage-specific genes (TMPRSS2, KLK3, KLK2, and FOLH1) and 4 cancer-specific genes (FAT1, HOXB13, AGR2, and STEAP2) and shows the list of genes contained within each multiplex prostate CTC assay with FAM/HEX ratio for each gene.

The present disclosure relates to methods and systems to obtain information from RNA from cancer cells, e.g., CTCs, in blood samples, exosomes from cancer cells in blood samples, or cell-free RNA from cancer cells, to help predict whether a given anti-cancer regimen will work effectively to treat a specific type of cancer in a given patient. These methods and systems combine the power of isolation techniques such as ultrahigh-throughput microfluidic techniques, for example, negative depletion techniques, e.g., those using negative depletion of hematopoietic cells to isolate untagged CTCs in a blood sample, with analysis techniques, such as droplet-based digital polymerase chain reaction (PCR) assays focused on RNA markers of specific cancer lineages. The specific assay methods, but not the new predictive analysis methods described herein, are described in further detail in PCT WO2016154600, which is incorporated herein by reference in its entirety.

The new methods include steps carried out by comparing the expression levels of various markers to reference standards, and by comparing these expression levels in patients who are destined to respond to specific cancer therapy or likely to have an early progression of their cancer. Such measurements can be informative at pretreatment baseline or they may emerge through serial blood monitoring once treatment is initiated. The value of these measurements lies in the information provided with respect to specific treatment choices. As multiple treatment options are available for patients with a variety of different cancers, information that helps individualize and guide the rational selection of therapy based on molecular markers becomes critical for effective cancer therapy.

As a specific example discussed in more detail below, patients with prostate cancer that have an elevated level of FOLH1 (PSMA) and/or HOXB13 before any therapy is started (e.g., above 2.5 transcripts per mL or other predetermined threshold) will not do well if treated only with abiraterone (e.g., ZYTIGA®). Such patients should be considered for alternative non-hormonal therapies (e.g., taxane chemotherapy or radio-isotope therapy), PARP inhibitors, or novel experimental therapies currently being developed, or combinations of existing therapies that are being tested in patients at high risk of recurrence.

In addition, other CTC isolation technologies than are described herein can also be used in the new methods as long as they provide partially purification of cells (e.g., filtration, positive tumor cell selection), although the quality of the RNA and hence the sensitivity of the assay will be inferior to the microfluidic technologies. Similarly, other digital PCR technologies applied to RNA are capable of detecting lineage-specific primers, although the sensitivity of the droplet-based assay is likely to be the highest.

General Concepts of the Assay Methods

The isolation techniques are used to enrich CTCs from a blood sample, e.g., using ultrahigh-throughput microfluidic such as the so-called "CTC-iChip" described in, for example, International PCT Application WO 2015/058206 and in Ozkumur et al., "Inertial Focusing for Tumor Antigen-Dependent and -Independent Sorting of Rare Circulating Tumor Cells," *Sci. Transl. Med.*, 5:179ra47 (2013). The CTC-iChip uses a CTC antigen-independent approach in which WBCs in the blood sample are labeled with magnetic beads, and the sample is then processed through two enrichment stages. The first stage uses deterministic lateral displacement to remove small and flexible cells/particles (RBCs, platelets, unbound magnetic beads, and plasma) while retaining larger cells (CTCs and WBCs). The second stage moves all cells into a narrow fluid stream using inertial focusing and then uses a magnetic field to pull bead-labeled WBCs out of the focused stream, leaving highly enriched CTCs. The CTC-iChip product from 10 ml of whole blood typically contains <500,000 RBCs, <5,000 WBCs, and a variable number of CTCs.

Some analysis techniques further enrich and analyze the isolated CTCs, e.g., as obtained from the CTC-iChip, e.g., using droplet microfluidics. Some basic information on droplet microfluidics is described generally in Jeremy et al., "Ultrahigh-Throughput Screening in Drop-Based Microfluidics for Directed Evolution," Proc. Natl. Acad. Sci. USA, 107:4004 (2010).

As used herein, the droplet microfluidic techniques can, in certain implementations, include encapsulation of single cells, RT-PCR reagents, and lysis buffer into droplets of typically non-aqueous liquids (e.g., fluorocarbons, hydrofluorocarbons, mineral oil, silicone oil, and hydrocarbon oil; surfactants can also be include in the non-aqueous liquid, e.g., Span80, Monolein/oleic acid, Tween20/80, SDS, n-butanol, ABIL EM90, and phospholipids), in the size range of, e.g., about 0.5 pL to 15 nL in volume and, e.g., 10 to 300 µm, e.g., 20 to 100 µm, e.g., 30 to 50 µm, e.g., 35 µm in diameter. As used in the new methods described in the present disclosure, these techniques further include amplification of cancer-specific transcripts within the droplets to produce a fluorescent signal, and sorting of amplification-positive drops. This approach results in isolation of pure CTCs that can be sequenced and analyzed for determining the potential efficacy of a specific anti-cancer therapy in a specific patient.

Due to the high heterogeneity of CTCs, it is useful to use multiplexed amplification to detect as many CTCs as possible. Thus, instead of using one pair of primers in the PCR mixture, one can increase the probability of detecting and sorting CTCs using a combination of tumor specific primers. For additional information on the use of PCR for sorting cancer cells, see, e.g., Eastburn et al., "Identification and genetic analysis of cancer cells with PCR-activated cell sorting," Nucleic Acids Research, 2014, Vol. 42, No. 16 e128.

In the new assay methods, CTCs are lysed to release RNA molecules, which are representative of the genes expressed in a cancer cell. Most are "lineage" specific, rather than cancer specific, for example any prostate cell (whether cancerous or not) expresses these markers. However, normal blood cells do not, and the fact that the signal is derived from a cell circulating in the bloodstream defines it as an abnormal signal. By converting the RNA to cDNA, one can amplify this lineage signal using PCR. Droplet digital PCR, which is extraordinarily sensitive, is used to allow converting the signal from a single cancer cell (i.e., one signal in an imaging assay) into thousands of positive immunofluorescent droplets. The combination of multiple, highly curated gene transcripts ensures high sensitivity and specificity for cancer, and also allows for functional insights (as in the status of hormone responsive pathways in prostate and breast cancers).

As noted, the new assay methods focus on the detection and analysis of high quality RNA rather than DNA. While there has been considerable work on DNA mutation detection in plasma and in CTCs, the present methods rely on RNA markers for the following reasons:

1. DNA mutations are not tumor specific, and the discovery that a healthy individual has some unidentified cancer cells in the blood is a very difficult clinical situation. In contrast, by selecting tumor-specific RNAs (e.g., prostate vs lung), the new methods can identify the source of cancer cells in the blood.

2. DNA mutations are very heterogeneous and besides a few recurrent mutations shared by many cancers, most blood-based mutation detection strategies require pre-existing knowledge of the mutations present in the primary tumor (i.e., not appropriate for screening for unknown cancers). In contrast, all tumor cells derived from specific organs express common lineage markers at the RNA level. Thus, a single cocktail of markers is used in the new methods for each individual type of cancer.

3. Low levels of CTCs are shed by invasive cancers before metastases are established (i.e., it is not too late for blood-based detection), but the presence of tumor cells in the blood connotes vascular invasion (i.e., invasive rather than indolent cancer). That is not the case for plasma DNA or plasma protein markers, which are leaked from dying cells in the primary tumor, and do not necessarily indicate vascular invasion. For example, serum PSA protein in the blood is shed by both benign prostate cells as well as primary prostate cancers. On the other hand, CTCs expressing PSA are shed only by invasive prostate cancers.

4. The analysis of RNA using the novel digital scoring technologies described herein is extraordinarily sensitive. However, free RNA is degraded in the bloodstream, and the use of isolation systems as described herein, such as microfluidic negative depletion systems (e.g., the CTC-Chip system) is unique in that the untagged tumor cells have high quality RNA that is extractable.

The choice of cDNA as a target molecule over DNA was made to not only to boost the signal originating from each tumor cell, but also to specifically target only tumor cell transcripts to the exclusion of white blood cell (WBC) transcripts. The boost in signal is a significant advantage, as it avoids the need for the isolation of CTCs to very high levels of purity. That is, it enables robust and repeatable results with products that contain one or more "isolated" CTCs that are still surrounded by hundreds or thousands of contaminating WBCs, e.g., leukocytes, in the same product. Nevertheless, the strategy of targeting cDNA made from RNA as used in the new methods allows the new assay methods to be exquisitely tailored for maximum specificity with minimal levels of CTC purity compared to prior approaches.

The CTC-iChip technology is highly efficient at isolating non-hematopoietic cells by microfluidic depletion of antibody tagged leukocytes. This feature of the CTC-iChip provides intact tumor-derived RNA (at levels far above those obtained using other technologies), and it is independent of tumor cell surface epitopes (which are highly heterogeneous among cancers and among epithelial vs mesenchymal cell subtypes within an individual cancer). Furthermore, even pre-apoptotic cancer cells whose antibody staining and selection is suboptimal for imaging analysis can provide a source of tumor-specific RNA that can be scored using the methods described herein. For all these reasons, an isolation technology or system that provides high quality RNA from intact CTCs with at least some reduction in the WBCs found in the sample along with the rare CTCs, such as a microfluidic negative depletion system, e.g., the CTC-iChip, is an important first step isolation before the tumor-specific digital readout is applied to the product.

The droplet-based digital detection of extremely rare molecules within a heterogeneous mixture was originally developed for PCR amplification of individual DNA molecules that are below detection levels when present within a heterogeneous mixture, but which are readily identified when sequestered within a lipid droplet before being subjected to PCR. The basic technology for droplet-based digital PCR ("Droplet Digital PCR (ddPCR)") has been commercialized by RainDance and Bio-Rad, which provide equipment for lipid encapsulation of target molecules followed by PCR analysis. Important scientific advances that made this possible include work in the laboratory of David Weitz at Harvard and Bert Vogelstein at Johns Hopkins. For example, see U.S. Pat. Nos. 6,767,512; 7,074,367; 8,535,889; 8,841,071; 9,074,242; and U.S. Published Application No. 2014/0303005. See also U.S. Pat. No. 9,068,181.

However, droplet digital PCR itself is not biologically significant unless coupled to a biological source of material, which is key to the new methods described herein. For instance, detection of lineage-specific RNAs (the central focus of the detection strategy described herein) does not distinguish between normal prostate epithelial cells and cancerous prostate cells. As such, detection of prostate-derived transcripts in the blood is not meaningful: they are present within debris from normal prostate cells or exosomes. It is only when coupled with the isolation of whole CTCs (i.e., intact CTCs in the blood) that the ddPCR assay achieves both extraordinary sensitivity and specificity. Hence, these two technologies are ideally suited for each other, because the isolation systems provide high quality RNA, and the droplet-based digital PCR assays are focused on RNA markers in the new methods.

One additional aspect is important to the overall success of the new assay methods. As noted, the new assay methods described herein use cDNA made from total RNA, but key to this use is the identification of appropriate biomarkers that are tumor lineage-specific for each type of cancer, yet are so unique as to be completely absent in normal blood cells (even with ddPCR sensitivity). The selection, testing, and validation of the multiple target RNA biomarkers for each type of cancer described herein enable the success of the new assay methods.

Assay Method Steps

The new assay methods start with the isolation of partially pure CTCs using an isolation system, such as a microfluidic negative depletion system, up to and including the analysis of data from a droplet digital PCR instrument. There are ten main assay steps, some of which are optional, though generally provide better results:

1. isolating from the blood sample a product including CTCs and other cells present in blood; e.g. from a patient or a subject;

2. reducing a volume of the rare cell-containing product (optional);

3. isolating ribonucleic acid (RNA) molecules from the product, e.g., by cell lysis, and generating cDNA molecules in solution from the isolated RNA; e.g., by RT-PCR of RNA released from cells contained in the product;

4. cleanup of cDNA synthesized during the RT-PCR step (optional);

5. pre-amplifying the cDNA using gene-specific targeted preamplification probes, e.g., using the Fluidigm BioMark™ Nested PCR approach, or non-specific whole-transcriptome amplification, e.g., using the Clontech SMARTer™ approach (optional);

6. encapsulating cDNA molecules in individual droplets, e.g., along with PCR reagents;

7. amplifying cDNA molecules within each of the droplets in the presence of reporter groups configured to bind specifically to cDNA from CTCs and not to cDNA from other cells, e.g., using PCR;

8. detecting droplets that contain the reporter groups (e.g., "positive" droplets) as an indicator of the presence of cDNA molecules from CTCs in the droplets;

9. analyzing CTCs in the detected droplets, e.g., to determine the presence of a particular disease in a patient or subject; and 10. detecting the expression of specific cancer-specific or lineage-specific genes in the cancer cells, e.g., CTCs, above the low background levels as determined by healthy donor controls (set at a level of 2.5), to determine whether a specific anti-cancer regimen is expected to be effective for that specific patient's specific tumor.

The background levels of these cancer-specific or lineage-specific genes are determined by measuring their expression in CTCs (or exosomes) in the blood of many patients without cancer (age-matched to those patients with cancer for a given type of cancer). The predictive value of these cancer-specific or lineage-specific gene markers are then evaluated by monitoring their expression prior to initiation of and during treatment with a specific cancer therapy in many patients over time, e.g., 6 to 12 months, 15 months, 18 months, 21 months, 24 months or more, and determining each patient's progression-free survival and overall survival statistics over each time period. These data are then used to prepare reference standards for each gene and each anti-cancer treatment regimen against which new patient samples can be compared to determine whether a proposed anti-cancer treatment regimen is likely to be effective in a specific patient, and if so, how effective compared to another potential treatment regimen.

For example, in patients with metastatic castration-resistant prostate cancer, the present inventors have discovered that those patients not having detectable expression of the genes HOXB13 and FOLH1 (PSMA), in their CTCs, as measured by the digital CTC quantitation assay, e.g., a level lower than 2.5 transcripts per mL of blood, will have a better overall survival and progression-free survival when treated with anti-androgen therapy than patients who have a high expression level of these two genes in their CTCs, e.g., a level higher than 2.5 transcripts per mL of blood. The expression of these prostate lineage markers is also detectable in exosomes and other tumor-derived RNA in the blood of patients with prostate cancer.

As described in further detail below, one of the important features of the new d-CTC assay methods is the careful selection of a number of target gene biomarkers (and corresponding primers) that deliver excellent sensitivity, while simultaneously maintaining nearly perfect specificity. A unique list of target gene biomarkers described herein (Table 3, below) was determined using bioinformatics analyses of publicly available datasets and proprietary RNA-Seq CTC data. Great care was taken to select markers that are not expressed in any subpopulations of leukocytes, but are expressed at a high enough frequency and intensity in CTCs to provide a reliable signal in a reasonably wide array of different and distinct patients. A specific set of markers was selected for each cancer type (e.g., prostate cancer, breast cancer, melanoma, lung cancer, pancreatic cancer, among others) and it is specific ones or sets of these markers that are predictive of the potential efficacy of various anti-cancer therapies.

The digital measurement of CTC-derived mRNAs provides not only a level of overall tumor burden for these specific cancers, which is an indicator of cancer activity and response or non-response to particular therapies, but it also provides specific information related to the genes being tested. For example, HOXB13 and FOLH1 in prostate cancers are markers of abnormal androgen signaling, a key characteristic of prostate cancers that are resistant to anti-androgenic therapies. Similarly, in breast cancer, response to hormonal therapies is dependent on the activity of the estrogen receptor pathway, which can be measured within CTCs or exosomes using RNA transcripts. In patients undergoing immunotherapy for cancer, such as melanoma, the presence of differentiation markers within CTCs or related blood vesicles can also indicate the expression of unique sets of genes that activate the immune system, and hence predict response or non-response to immunological treatments.

The separate steps of the assay methods will now be described in more detail.

1. CTC Isolation

Patient blood is run through the CTC-iChip, e.g., version 1.3M or 1.4.5T and a sample is collected in a 15 mL conical tube on ice. CTC-iChips were designed and fabricated as previously described (Ozkumur et al., "Inertial Focusing for Tumor Antigen-Dependent and -Independent Sorting of Rare Circulating Tumor Cells," Science Translational Medicine, 5(179):179ra47 (DOI: 10.1126/scitranslmed.3005616) (2013)).

The blood samples (~20 mls per cancer patient) are collected in EDTA tubes using approved protocols. These samples are then incubated with biotinylated antibodies against CD45 (R&D Systems) and CD66b (AbD Serotec, biotinylated in house) and followed by incubation with Dynabeads® MyOne® Streptavidin T1 (Invitrogen) to achieve magnetic labeling of white blood cells (Ozkumur et al., 2013).

The sample is then processed through the CTC-iChip, which separates the blood components (red and white blood cells and platelets) as well as unconjugated beads away from the CTCs. The CTCs are collected in solution while the red blood cells, platelets, unconjugated beads and the tagged white blood cells are collected in a waste chamber. The process is automated and 10 ml of blood is processed in 1 hour.

2. Volume Reduction and Storage of the Rare Cell-Containing Product

To fully lyse all cells isolated in the product, it is preferable to reduce the product volume from a typical starting point of several milliliters to a final volume of about 100 µl. This can be achieved, for example, by centrifuging the product, and resuspending in pluronic buffer in preparation for cell lysis and generation of cDNA. At this point samples can be processed for long-term storage by adding RNAlater™ (ThermoFisher), followed by flash-freezing in liquid nitrogen and storage at −80 C.

3. Isolating RNA and Generation of cDNA from Cells in the Product

The RNA isolation step is important to the process to fully release all RNA molecules from cells in preparation for RT-PCR. A one-step, in-tube reaction can be used to minimize the risk of cell and RNA loss likely to be incurred during standard transfer steps. For example, one can use the Invitrogen SuperScript III® First-Strand Synthesis Supermix® for qRT-PCR kit, by adding the RT-PCR mastermix directly to the pelleted product, pipetting to lyse fully, and performing the reaction according to the kit protocol targeting a 1:1 RNA:cDNA ratio. Once cDNA has been synthesized, RNase H is applied to the reaction to remove any remaining RNA. Alternatively, if one wants to perform whole transcriptome pre-amplification of the sample in a later step, cDNA can be synthesized using the SMARTer™ Ultra Low Input RNA Kit protocol, which uses proprietary oligonucleotides and reverse transcriptase enzyme.

4. Cleanup of cDNA Synthesized During RT-PCR

Another useful, yet optional, step in the process involves the removal of lysis reagents from the cDNA-containing solution. The presence of harsh detergents can lead to the destabilization of the droplets used in the ddPCR method, once the cDNA-containing solution is transferred to the ddPCR instrument. Detergent removal can be accomplished, e.g., through the use of Solid Phase Reversible Immobilization (SPRI). This technique uses coated magnetic beads to first bind cDNA of a specific size range, then allows removal of detergent-containing supernatant, and finally elution of pure cDNA for input into the ddPCR instrument. In addition to the cleanup of the RT-PCR, the SPRI process also accomplishes a size selection of cDNA, which reduces the number of non-target cDNA molecules that enter the ddPCR phase of the process, which in turn reduces background and noise.

5. Pre-Amplification

Pre-amplification of the cDNA is an optional step that increases the number of template molecules that can be detected in the droplet PCR step thus improving signal-to-noise ratio and boosting the confidence in a positive readout. It can be a very powerful approach for the detection of markers that are expressed at low levels in CTCs, and for analyzing samples that contain very small numbers of possibly apoptotic CTCs, such as in the context of early detection of pre-metastatic disease. These two approaches have been modified to be applied in the workflow of d-CTC assay. Specific Targeted Amplification (STA), based on the Fluidigm BioMark™ Nested PCR protocol, relies on the use of primers specifically designed to amplify the region targeted by the probes used in the droplet PCR step (see Table 2). These primers were carefully designed and tested in conjuncture with their respective fluorescent probes to ensure efficient and specific amplification without increase in noise in healthy controls. Alternatively, whole transcriptome amplification, based on the SMARTer™ Ultra Low Input RNA Kit protocol, relies on the amplification of every transcript in the product, including both those found in WBCs and those found in CTCs, using random primers.

6. Encapsulation of cDNA Plus PCR Reagents in Droplets

Once cDNA has been synthesized and purified of contaminating detergents, the entire aggregate of cDNA molecules in solution plus qPCR reagents is divided into many tiny compartmentalized reactions, for example, by a droplet making to instrument, e.g., a droplet generator such as the Biorad Automated Droplet Generator, which generates 20,000 droplets per sample. Each reaction consists of an extremely small droplet of non-aqueous fluid, e.g., oil (PCR stable, e.g., proprietary formulation from vendor), which contains Taqman-type PCR reagents with gene-specific primers and an oligonucleotide probe, and a small amount of sample. Once droplet generation is complete, the sample consists of an emulsion containing a vast number of individual PCR-ready reactions.

For this step, one can use the PCR probes and related primers for any one or two or more different target genes listed in Table 1 below for overall determination of tumor load, e.g., to determine tumor progression or response to therapy, in single or multiplex reactions. Thus, although in some cases a single set of PCR primers and probes for a particular gene from Table 1 can be included in each droplet, it is also possible to multiplex PCR primers and probes for two or more different genes in each droplet using different fluorescent probes for each primer/probe set, to maximize the detection of tumor cells, given the heterogeneity of gene expression in CTCs. It is also possible to multiplex PCR primers and probes for multiple genes targeting different cancer types in each droplet, thus enabling the broad yet specific detection of multiple tumor types in a single assay.

7. PCR of Droplet Encapsulated cDNA Molecules

Standard PCR cycling is performed on the entire emulsion sample using qPCR cycling conditions. The reaction is carried to 45 cycles to ensure that the vast majority of individual droplet-PCR volumes are brought to endpoint. This is important because, although the reaction is performed with Taqman-type qPCR reagents and cycled under qPCR conditions, the fluorescent intensity of the sample will not be measured during the PCR cycling, but rather in the next step.

8. Detection of Positive Droplets

Since each individual partitioned PCR is brought fully to endpoint before any measurement of fluorescence is performed, each individual droplet will be either a fully fluorescent droplet or will contain virtually no fluorescence at all. This enables the simple enumeration of all positive (fluorescent) and negative (non-fluorescent) droplets.

9. Analysis

Because the upstream RT-PCR targeted a 1:1 RNA:cDNA ratio, each positive droplet should represent a single originating RNA transcript. This interpretation depends on the number of individual droplets far exceeding the number of target cDNA molecules. In the new process, at one extreme we consider the possibility of a single CTC being isolated and lysed, releasing some number of RNA transcripts that are then reverse-transcribed 1:1 into cDNA, partitioned, PCR-amplified, and enumerated.

We estimate that in the case of a moderately expressed gene, such as the KLK3 gene in prostate cancer cells, each cell contains approximately 80-120 copies of KLK3 mRNA. The Biorad QX200 ddPCR System generates 20,000 droplets, which ensures that for small numbers of isolated CTCs and moderately-expressed target genes there will never be more than one target cDNA molecule per droplet. On the other hand, in cases where the numbers of CTCs reach dozens or hundreds, for moderately-expressing genes there will likely be multiple copies of target cDNA per droplet. In such cases, approximate numbers of originating transcript can be estimated using Poisson statistics.

10. Detecting and Determining Anti-Cancer Regimen Efficacy

The last step includes detecting the expression of particular cancer-specific or lineage-specific genes in the cancer cells, e.g., CTCs, above the low background levels as determined by healthy donor controls (e.g., set at a level of 2.5 transcripts per mL blood), to determine whether a specific anti-cancer regimen is expected to be effective for that patient's specific tumor.

The background levels of these cancer-specific or lineage-specific genes are determined by measuring their expression in CTCs (or exosomes) in the blood of many patients without cancer (age-matched to those patients with cancer for a given type of cancer). The predictive value of these cancer-specific or lineage-specific gene markers are then evaluated by monitoring their expression prior to initiation of and during treatment with a specific cancer therapy in many patients over time, e.g., 6 to 12 months, 15 months, 18 months, 21 months, 24 months or more, and determining each patient's progression-free survival and overall survival statistics over each time period. These data are then used to prepare reference standards for each gene and each anti-cancer treatment regimen against which new patient samples can be compared to determine whether a proposed anti-cancer treatment regimen is likely to be effective in a specific patient, and if so, how effective compared to another potential treatment regimen.

For example, in patients with metastatic castration-resistant prostate cancer ("CRPC"), those patients not highly expressing the genes HOXB13 and FOLH1 (PSMA), e.g., a level lower than 2.5 transcripts per mL blood, will have a better overall survival and progression-free survival when treated with anti-androgen therapy than patients who have a high expression level of these two genes, e.g., a level higher than 2.5 transcripts per mL blood.

In particular, by combining microfluidic enrichment of viable CTCs with digital quantitation of CTC-derived RNA, the new methods described herein provide a highly sensitive and specific assay for serial non-invasive sampling of prostate cancer. This approach overcomes a major limitation of CTC analyses to date, namely the microscopy-based quantitation of multiple immunofluorescence-conjugated antibody stains within mixed cell populations, with its associated requirement for calibration and thresholding of multiple fluorescence parameters, followed by manual verification of individual images. The extraordinary high sensitivity and specificity of sequence-based approaches, which are readily multiplexed to interrogate multiple markers simultaneously, provide greatly improved signal over traditional cell imaging methods. In a pilot cohort of men on first line therapy for early recurrence of prostate cancer, we demonstrated the potential utility of quantitative CTC measurements of both normal prostatic transcripts and aberrant RNA products in informing therapeutic choices.

Conceptually, the application of a digital RNA-based PCR output to microfluidic CTC-enriched cell populations presents a number of important advantages. The use of purified whole CTCs in the bloodstream as the source of RNA ensures that the measured signal is derived from invasive cancer cells, as opposed to normal tissues, and hence it enables the use of RNA-based markers that are not unique to cancer. Recurrent cancer-specific markers are rare in prostate cancer, which has limited the application of mutation-based plasma DNA sequencing. In addition to lineage-based RNA markers, the role of aberrant androgen receptor ("AR") splice forms in acquired resistance to hormonal therapy necessitates blood-based RNA measurement. In this context, the microfluidic depletion of normal hematopoietic cells from blood specimens is particularly effective in preserving RNA integrity within CTCs, which are not subject to antibody-manipulation or fixation and thus provide excellent signal for digital PCR quantitation. Along with microfluidic CTC isolation, digital scoring of CTC signal for both prostate lineage transcripts and prostate cancer-specific transcripts can be readily automated for high-throughput analyses, making it a realistic tool for clinical applications.

The recent development of multiple potent treatment modalities for metastatic prostate cancer brings with it the need to identify predictive makers of response. To date, the most significant markers have focused on the demonstration of continued activity of the androgen receptor, which is targeted by many therapeutic modalities. Molecular imaging-based strategies to measure androgen signaling have been demonstrated in some cases, but the availability of blood-based sampling would greatly enhance the utility of such monitoring. We have previously reported that scoring of CTCs for expression of the androgen-driven protein PSA versus the androgen-repressed protein PSMA can be translated into an androgen receptor-induced gene ("AR-on") versus an androgen-repressed gene ("AR-off") CTC immunofluorescence-based signature.

In treatment-naive patients, virtually all CTCs have AR-on signal, which converts to AR-off following initiation of Androgen Deprivation Therapy ("ADT"). Patients with CRPC, however, most frequently show simultaneous expression of AR-on and AR-off protein signatures, consistent with aberrant AR signaling. In this context, the predictive value of CTC-derived expression of the non-AR target genes HOXB13 and FOLH1 (PSMA) is consistent with altered AR signaling. Germline mutations in HOXB13 have been correlated with increased susceptibility to prostate cancer, and the gene encodes a transcriptional coactivator of AR, which is a known marker of less differentiated prostate cancer, which has also been linked to hormonal therapy resistance in ER-positive breast cancer. FOLH1 is a well-established marker for prostate lineage, normally suppressed by androgen signaling, but co-expressed with PSA in CRPC. Thus, overexpression of these markers within prostate CTCs identify cancers in which altered AR signaling pathways have significant roles in malignant proliferation, lessening the effectiveness of the androgen synthesis inhibitor abiraterone.

AR-V7 has recently emerged as a readily measurable surrogate for acquired androgen pathway independence, predicting resistance to third or fourth line abiraterone or enzalutamide therapy. Discordant results as to the predictive value of AR-V7 measurements most likely result from different CTC or exosome-based detection assays, as well as their application in patients at different stages of treatment and disease progression. For example, in a large retrospective clinical trial, AR-V7 was detectable in CTCs from only 3% of patients prior to fourth line therapy.

The application of a high sensitivity digital CTC assay and the serial sampling of patients before and during therapy provide a novel perspective on the significance of AR-V7 positivity. First, we note that detection of this splice variant in untreated patients at the time of first disease recurrence does not by itself indicate resistance to abiraterone; however, the persistence or emergence of AR-V7 in the setting of drug treatment is highly predictive of adverse outcome. In this context, it is likely that drug sensitive tumor cells are suppressed and AR-V7 directly measures the emergence of drug resistant tumor populations.

Second, the observation that downstream indicators of altered AR signaling (HOXB13 and FOLH1) are more commonly elevated than AR-V7 and are more predictive of adverse outcome when measured in pretreatment CTC specimens suggests that AR-V7 is one of a number of mechanisms that limit the efficacy of AR targeted therapies. The recent application of combined paclitaxel and leuprolide therapy in the initial treatment of high-risk prostate cancer shows the utility of risk stratification as described herein to enable individualized therapies in advanced disease.

The same techniques can be used to determine the expected efficacy of different therapies used for other types of cancers including melanoma and breast cancer. For example, as shown in Table 1 for melanoma, the following examples of treatments, treatment categories, and drugs can be tested for expected efficacy in specific patients using the assays and methods described herein. Similarly, Table 2 shows drugs and combinations of drugs used to treat breast cancer, which can be tested for efficacy in specific patients using the assays and methods described herein.

TABLE 1

| Melanoma Treatments | Treatment category | Drugs |
| --- | --- | --- |
| BRAFV600E inhibitors | Targeted therapy | Vemurafenib, Dabrafenib, Encorafenib |
| MEK inhibitors | Targeted therapy | Cobimetinib, Trametinib, Binimetinib |
| Anti-CTLA4 antibody | Immunotherapy | Ipilimumab |
| Anti-PD1 antibody | Immunothreapy | Pembrolizumab, Nivolumab |
| CDK4/CDK6 inhibitor | Targeted therapy | Palbociclib |

TABLE 2

| Mono-therapies: | Combination therapies: |
| --- | --- |
| Endocrine therapies (including ESR1 inhibitors, Aromatese Inhibitors, SERDS) | Endocrine therapies + CDK 4/6 inhibitors |
| Chemotherapy | Endocrine therapies + PI3K inhibitors |
| HER2 Inhibitors | Endocrine therapies + mTOR inhibitors |
| PI3K Inhibitors | Chemotherapy + PARP inhibitors |
| Immunotherapy | Chemotherapy + HER2 inhibitors |

Novel Gene Panels to Enable Lineage-Specific Identification of CTCs

As discussed above, the identification of gene transcripts that are highly specific for cancer cells within the context of surrounding normal blood cells is central to the new methods. While many genes are known to be more highly expressed in cancer cells, the vast majority of these genes also typically have at least limited expression in normal tissues, including blood. Given the extraordinary sensitivity required for this assay, complete absence of signal in normal blood cells is essential for high confidence identification of tumor cells in the bloodstream.

Candidate tumor-specific transcripts used to detect CTCs in blood are first selected by analyzing publicly available gene expression data sets derived from breast, prostate, lung, pancreas, and liver cancers and melanoma, as well as our lab-generated single cell RNA-Seq data from CTCs isolated from breast, prostate and pancreatic cancer patients and mouse models of these cancers. Transcripts whose expression is restricted to tumors and absent or undetectable in blood components are chosen for further downstream analysis. Demonstrating and validating total absence of expression (with the highest level of sensitivity, i.e., Digital PCR assays) in normal blood cells is important. In general, only ~10% of candidate genes predicted based on computational models or RNA Seq data are truly negative in human blood samples.

In particular, candidate tumor-specific mRNA transcripts for the detection of CTCs were initially identified through the analysis of gene expression data sets (microarray and RNA-Seq) derived previously for human breast, prostate, lung, pancreas, hepatocellular, and melanoma cancers. Specific publically available data sets used for this analysis include The Cancer Genome Atlas (TCGA) (The Cancer Genome Atlas, available online at tcga-data.nci.nih.gov/tcga/tcgaHome2.jsp) and the Cancer Cell Line Encyclopedia (CCLE) (available online at broadinstitute.org/ccle/home; see also, Barretina et al., The Cancer Cell Line Encyclopedia enables predictive modelling of anticancer drug sensitivity, *Nature* 483:603-607 (2012)). In addition, single-cell RNA-seq gene expression data from CTCs isolated from human patients with breast, prostate, and pancreatic cancers were analyzed (GEO accession numbers GSE51827, GSE60407, and GSE67980) (Aceto et al., Circulating tumor cell clusters are oligoclonal precursors of breast cancer metastasis, *Cell,* 158:1110-1122 (2014); Ting et al., Single-Cell RNA Sequencing Identifies Extracellular Matrix Gene Expression by Pancreatic Circulating Tumor Cells, *Cell Rep,* 8:1905-1918 (2014); and Miyamoto et al., RNA-Seq of single prostate CTCs implicates noncanonical Wnt signaling in antiandrogen resistance, *Science* 349:1351-1356 (2015). Tumor specific transcripts identified through these databases were then compared to human leukocyte RNA-Seq gene expression data (GEO accession numbers GSE30811, GSE24759, GSE51808, GSE48060, GSE54514, and GSE67980). Transcripts that displayed significant differential expression, with high expression in tumors and low or undetectable expression in leukocytes, were then selected for further downstream analysis. Moreover, a literature search was performed to select additional candidate tumor-specific transcripts. Between 50 and 100 candidate genes were selected for each type of human cancer.

For each candidate gene within each specific cancer type, two to four sets of PCR primers were designed to span regions across the target transcript. Primers are synthesized by IDT (Integrated DNA Technologies), probes are labeled with FAM or HEX, ZEN, and IABkFQ to create a probe targeting the middle of the amplicon. Unique features of our PCR primer design methodology necessary for the successful application of digital PCR-based mRNA transcript detection in human CTCs include the following: 1) the specific targeting of the 3' end of each mRNA transcript, given the proclivity of cellular mRNA transcripts to degrade from the 5'-end, particularly in unfixed, fragile cells such as CTCs; 2) the design of primers to generate amplicons that span introns in order to exclude the unintentional amplification of contaminating genomic DNA, for example from excess contaminating leukocytes in the enriched CTC mixture; and 3) the design of primers to inclusively amplify multiple splice variants of a given gene, given the uncertainty in some cases regarding the clinical relevance of specific splice variants.

The specificity of the primers was first tested by qRT-PCR using cDNA derived from cancer cell lines (representing breast, prostate, lung, pancreas, and liver cancers and melanoma). For each type of human cancer, 2 to 5 established cancer cell lines were cultured and used for initial testing to evaluate PCR primer performance and assess for expression of the target transcript in the specified cancer. To provide an initial test of specificity, the same primers were used to evaluate expression of the target transcript in leukocytes from healthy individuals who do not have a diagnosis of cancer. Leukocytes from a minimum of five different healthy individuals were tested in this phase of testing (mixture of male and female individuals—this was dependent on the type of cancer; i.e. candidate prostate cancer and breast cancer genes required the use of male or female healthy donors only, respectively).

Leukocytes from healthy individuals were isolated from whole blood using Cell Preparation Tubes with Sodium Heparin (CPT) (Becton, Dickinson, and Co., NJ) following product insert instructions. RNA extraction and first-strand cDNA synthesis was performed for cancer cell lines and isolated leukocytes using standard methods. The specificity of expression of each gene (using 2 to 4 distinct sets of primers for each gene) was tested using qRT-PCR (cell line cDNA as positive controls, leukocyte cDNA from healthy donors as negative controls, and water as an additional negative control). Transcripts present in cancer cell lines, but absent in leukocytes based on qRT-PCR testing were then selected for further validation by droplet digital PCR. The selection criteria to pass this stage of testing were highly stringent, and required qRT-PCR signal to be present in at least one cancer cell line and absent in all healthy donor leukocyte samples tested.

Target transcripts and specific primer pairs that passed the qRT-PCR stage of testing were further validated using droplet digital PCR. For this stage of testing, the CTC-iChip (see, e.g., Ozkumur et al., "Inertial focusing for tumor antigen-dependent and -independent sorting of rare circulating tumor cells," *Sci Transl Med*, 5, 179ra147 (2013) was used to process whole blood samples donated by healthy individuals. The CTC-iChip performs negative depletion of red blood cells, platelets, and leukocytes from whole blood, and generates a sample product that is enriched for cells in the blood that do not express leukocyte markers, including CTCs (which should not be present in healthy individuals). For each blood sample, the product from the CTC-iChip was supplemented with an RNA stabilization solution (RNAlater®, Life Technologies) and processed for RNA extraction and cDNA synthesis using standard methods. Droplet digital PCR (Biorad, CA) was then used to quantitate the number of transcripts present in each sample based on the specific primer pairs being tested. Samples assessed by droplet digital PCR during this phase of testing included cDNA from cancer cell lines, leukocyte cDNA from healthy donors processed through the CTC-iChip (at least four healthy individuals per primer pair being tested), and water as a negative control.

Criteria for passing droplet digital PCR testing were stringent, and included: 1) the presence of transcript signal in cancer cell lines (at least one cell line with >10 positive droplets); 2) excellent signal-to-noise ratio represented by separation of signal between positive and negative (empty) droplets; 3) minimal or absent droplet signal in healthy donors (<3 droplets per healthy donor); and 4) absent droplet signal in water (0 positive droplets).

Primers that amplified transcripts specifically in cell lines and not in leukocytes in the above droplet digital PCR testing were then subjected to detailed testing of sensitivity of signal. Using single cell micromanipulation, precise numbers of cancer cells (1, 5, 10, 25, and 50 cells) were spiked into whole blood donated by healthy individuals, and then processed through the CTC-iChip. Each sample was then processed as above for testing with droplet digital PCR, and evaluated for sensitivity to ensure the signal was sufficient for the desired clinical application.

The above stringent procedure of evaluating candidate genes and primers using qRT-PCR and droplet digital PCR resulted in a final primer list consisting of approximately 10% of the initial list of 50-100 candidate genes for each type of cancer (total of approximately 400 initial candidate genes). These primers are then further evaluated for signal in patient CTCs using blood samples donated by cancer patients undergoing cancer treatment at the MGH Cancer Center, collected under an IRB-approved clinical protocol. Key to this portion of the evaluation is a comparison with blood collected from healthy individuals without a diagnosis of cancer. The following Table 3 lists the primers and probes for that have been developed thus far using these methods for the specific detection of CTCs from patients with prostate, breast, hepatocellular, pancreatic, lung, and melanoma cancers using droplet digital PCR.

While a single gene for each cancer type could be used, the presence of multiple genes within each panel is useful both for sensitivity (CTCs are heterogeneous even within individual patients in their expression patterns) and specificity (detection of multiple gene signals confers added confidence that this represents a true cancer cell signature).

The gene list provided below in Table 3 includes transcripts that are unique to specific types of cancer (e.g., highly specific markers of prostate or breast or liver cancers), as well as genes that are shared by several cancer types, e.g., all epithelial cancer types (and thus may serve as pan-cancer markers), and genes that are induced in certain conditions (e.g., active androgen signaling in prostate cancer or active estrogen signaling in breast cancer). Thus, each type of cancer was assigned a specific panel of genes that is designed for optimal sensitivity, specificity, and clinically actionable information for the given cancer type.

In addition, primers described in Table 4 are designed to pre-amplify some of the genes listed in Table 3, while maintaining their high specificity. If STA is a method of choice, these nested primers become additional components of each cancer panel.

Gene Lists for Different Types of Cancers

The following Table 3 provides a list of names of genes (with (Genbank ID) and Sequence Identification numbers (SEQ ID NO)), along with cancer types for which they are selective (Br: breast, Lu: lung, Li: liver, Pr: prostate, Panc: pancreatic, Mel: melanoma). In addition, optimized primer sets are listed for each gene (primers 1 and 2), along with the composition of the fluorescent primer probes (e.g., 6-FAM™ (blue fluorescent label) or HEX™ (green fluorescent label) for tagged probes, and ZEN-31ABkFQ quencher) for optimal visualization of the digital PCR product.

TABLE 3

| Gene | Disease Group | Seq ID | Primer 2 | Seq ID | Primer 1 | Seq ID | Probe |
|---|---|---|---|---|---|---|---|
| AGR2 (10551) | Br, Lu, Li, Pr | 1 | CTG ACA GTT AGA GCC GAT ATC AC | 2 | CAA TTC AGT CTT CAG CAA CTT GAG | 3 | /56-FAM/ATG CTT ACG/ZEN/AAC CTG CAG ATA CAG CTC/31ABkFQ/ |
| ALDH1A3 (220) | Br, Lu, Panc | 4 | GGT GGC TTT AAA ATG TCA GGA A | 5 | TGT CGC CAA GTT TGA TGG T | 6 | /56-FAM/TTT TCA CTT/ZEN/CTG TGT ATT CGG CCA AAG C/31ABkFQ/ |
| CADPS2 (93664) | Br, Li, Lu, MeI | 7 | CTC TGC ATT TTT GGA CAT AGG AG | 8 | GCC TTG CAC TTC CAT TAT GAC | 9 | /56-FAM/TCC GAC GTG/ZEN/GTA CTG TCA TTC ACC T/31ABkFQ/ |
| CDH11 (1009) | Br, Lu, Panc | 10 | GAG GCC TAC ATT CTG AAC GC | 11 | GTG GTT CTT TCT TTT GCC TTC TC | 12 | /56-FAM/CAT CCT CGC/ZEN/CTG CAT CGT CAT TCT/31ABkFQ/ |
| CDH3 (1001) | Br, Li, MeI | 13 | GTT TCA TCC TCC CTG TGC TG | 14 | GCT CCT TGA TCT TCC GCT TC | 15 | /56-FAM/CTG CTG GTG/ZEN/CTG CTT TTG TTG GT/31ABkFQ/ |
| COL8A1 (1295) | Br, Lu | 16 | GAT GCC CCA CTT GCA GTA | 17 | CCT CGT AAA CTG GCT AAT GGT | 18 | /56-FAM/AGT ATC CAC /ZEN/ACC TAC CCC AAT ATA TGA AGG AAA/31ABkFQ/ |
| EGFR (1956) | Br, Lu, Li, Panc | 19 | CTG CTG CCA CAA CCA GT | 20 | TTC ACA TCC ATC TGG TAC GTG | 21 | /56-FAM/CTG CCT GGT/ZEN/CTG CCG CAA ATT C/31ABkFQ/ |
| FAT1 (2195) | Br, Lu, Li, MeI, Pr, Panc | 22 | GAT CCT TAT GCC ATC ACC GT | 23 | ATC AGC AGA GTC AAT CAG TGA G | 24 | /56-FAM/TCT TGT CAG/ZEN/CAG CGT TCC CGG/31ABkFQ/ |
| FAT2 (2196) | Br, Lu | 25 | CCT GGA TGC TGA CAT TTC TGA | 26 | TCC TCC ACT CAT CTC CAA CT | 27 | /56-FAM/ACC TGC TAC/ZEN/ATC ACA GAG GGA GAC C/31ABkFQ/ |
| FOLH1 (2346) | Pr | 28 | CAA TGT GAT AGG TAC TCT CAG AGG | 29 | TGT TCC AAA GCT CCT CAC AA | 30 | /56-FAM/ATG AAC AAC/ZEN/AGC TGC TCC ACT CTG A/31ABkFQ/ |
| HOXB13 (261729) | Br, Lu, Pr | 31 | CAG CCA GAT GTG TTG CCA | 32 | CTG TAC GGA ATG CGT TTC TTG | 33 | /56-FAM/CAG CAT TTG/ZEN/CAG ACT CCA GCG G/31ABkFQ/ |
| KLK2 (3817) | Pr | 34 | GCT GTG TAC AGT CAT GGA TGG | 35 | GTC TTC AGG CTC AAA CAG GT | 36 | /56-FAM/TGG CTA TTC/ZEN/TTC TTT AGG CAA TGG GCA/31ABkFQ/ |
| KLK3 (354) | Pr | 37 | GTG TGC TGG ACG CTG GA | 38 | GTG ATA CCT TGA AGC ACA CCA TTA | 39 | /56-FAM/AAA GCA CCT/ZEN/GCT CGG GTG ATT CT/31ABkFQ/ |
| LSAMP (4045) | MeI | 40 | CAC ATT TGA GTG AAG CTT GTC G | 41 | GCG GAT GTC AAA CAA GTC AAG | 42 | /56-FAM/TCC AAG AGC/ZEN/AAT GAA GCC ACC ACA/31ABkFQ/ |
| MAGEA6-RM1 (4105) | MeI | 43 | GAA GGA GAA GAT CTG CCA GTG | 44 | GCT GAC TCC TCT GCT CAA G | 45 | /56-FAM/TTG CCC TG/ZEN/CCA GAG TCA TCA TGO/31ABkFQ/ |

TABLE 3-continued

| Gene | Disease Group | Seq ID | Primer 2 | Seq ID | Primer 1 | Seq ID | Probe |
|---|---|---|---|---|---|---|---|
| MET (4233) | Br, Li, Lu, Panc | 46 | CCA GTA GCC TGA TTG TGC AT | 47 | TGT CAG TGA TTC TGT TCA AGG A | 48 | /56-FAM/AGT CAT AGG/ZEN/AAG AGG GCA TTT GGT TGT/31ABkFQ/ |
| MLANA (2315) | MeI | 49 | ACT CTT ACA CCA CGG CTG A | 50 | CCA TCA AGG CTC TGT ATC CAT | 51 | /56-FAM/AAG ACT CCC/ZEN/AGG ATC ACT GTC AGG A/31ABkFQ/ |
| NPY1R (4886) | Br, Lu | 52 | GGA TCT GAG CAG GAG AAA TAC | 53 | GAA TTC TTC ATT CCC TTG AAC TGA | 54 | /56-FAM/AGC AGG AGC/ZEN/GAA AAA GAC AAA TTC CAA AG/31ABkFQ/ |
| OCLN (100506658) | Br, Lu, Li | 55 | AAG ATG GAC AGG TAT GAC AAG TC | 56 | ACT CTT TCC ACA TAG TCA GAT GG | 57 | /56-FAM/TGC AGA CAC/ZEN/ATT TTT AAC CCA CTC CTC G/31ABkFQ/ |
| PDZRN3 (23024) | MeI | 58 | TGT CCT GGC TGT TCA TTC TG | 59 | TGG ATC CCT ATC TCT TGC CA | 60 | /56-FAM/AGC TCC TCC/ZEN/CTG TCC ATC |
| PGR (5241) | Br | 61 | GGC AAT TGG TTT GAG GCA A | 62 | GGA CTG GAT AAA TGT ATT CAA GCA | 63 | /56-FAM/ACA AGA TCA/ZEN/TGC AAG TTA TCA GAA GTT TTT GTA GTT/31ABkFQ/ |
| PKP3 (11187) | Br, Li, Lu, Panc | 64 | CTG GTG GAG GAG AAC GG | 65 | GGT CGC TGG ATG AAA GGT T | 66 | /56-FAM/AGT GTC CGC/ZEN/AGC AGC TCG AA/31ABkFQ/ |
| PMEL (6490) | MeI | 67 | CAG GCA TCG TCA GTT TCC | 68 | ACA CAA TGG ATC TGG TGC TAA | 69 | /56-FAM/TTT GGC TGT/ZEN/GAT AGG TGC TTT GCT G/31ABkFQ/ |
| PPL (5493) | Br, Lu, Li | 70 | GAG GAG AGA ATC AAC AAA CTG C | 71 | AGG TTC AGG TAC TCC TTC CAG | 72 | /56-FAM/AGG AAC TCC/ZEN/ATT GAG GCG CAC AT/31ABkFQ/ |
| RXRG (6258) | MeI | 73 | ATA CTT CTG CTT GGT GTA GGC | 74 | AGC CAT TGT ACT CTT TAA CCC A | 75 | /56-FAM/CTC TGA GGT/ZEN/GGA GAC TCT GCG AGA/31ABkFQ/ |
| RND3 (390) | Br, Lu, Li, MeI, Panc | 76 | CCG AGA ATT ACG TTC CTA CAG TG | 77 | GCG GAC ATT GTC ATA GTA AGG A | 78 | /56-FAM/ACG GCC AGT/ZEN/TTT GAA ATC GAC ACA C/31ABkFQ/ |
| S100A2 (6273) | Br, Lu, Li, Panc | 79 | CTG CCT TGC TCT CCT TCC | 80 | CTT ACT CAG CTT GAA CTT GTC G | 81 | /56-FAM/ACC TGG TCT/ZEN/GCC ACA GAT CCA TG/31ABkFQ/ |
| SCGB2A1 (4246) | Br | 82 | ACT TCC TTG ATC CCT GCC A | 83 | GTC TTT TCA ACC ATG TCC TCC A | 84 | /56-FAM/CCATGA AGC/ZEN/TGC TGA TGG TCC TCA/31ABkFQ/ |
| SFRP1 (6422) | MeI | 85 | CAA TGC CAC CGA AGC CT | 86 | CTT TTA TTT TCA TCC TCA GTG CAA AC | 87 | /56-FAM/TGT GAC AAC/ZEN/GAG TTG AAA TCT GAG GCC/31ABkFQ/ |
| SOX10 (6663) | MeI | 88 | CTT GTC ACT TTC GTT CAG CAG | 89 | CTT CAT GGT GTG GGC TCA | 90 | /56-FAM/TTG TGC AGG/ZEN/TGC GGG TAC TGG/31ABkFQ/ |
| SCHLAP1/ SET 4 (101669767) | Pr | 91 | TCC TTG GAT GAC TCT CCC TAC | 92 | AGA TAC CAC CTC CCT GAA GAA | 93 | /56-FAM/CCA ATG ATG/ZEN/AGG AGC GGG ATG GAG/31ABkFQ/ |

TABLE 3-continued

| Gene | Disease Group | Seq ID | Primer 2 | Seq ID | Primer 1 | Seq ID | Probe |
|---|---|---|---|---|---|---|---|
| SCHLAP1 SET 5 | Pr | 94 | AGA GGT TTA ATG GGC TCA CAG | 95 | CTC TGG TCT GTC GTC ATG TAA G | 96 | /56-FAM/ACA TGC CTT/ZEN/TCA CCT TCT CCA CCA/ 31ABkFQ/ |
| AMACR (23600) | Pr | 97 | CAC ACC ACC ATA CCT GGA TAA T | 97 | TCA CTT GAG GCC AAG AGT TC | 99 | /56-FAM/AGA AAC GGA/ZEN/GGT CCA GCC AAG TTC/ 31ABkFQ/ |
| AR Variant 7/SET1 (367) | Pr | 100 | CTT TCT TCA GGG TCT GGT CAT T | 101 | CTT GTC GTC TTC GGA AAT GTT ATG | 102 | /56-FAM/AAG CAG GGA/ZEN/TGA CTC TGG GAG AAA/ 31ABkFQ/ |
| AR Variant 7 SET | Pr | 103 | GAG GCA AGT CAG CCT TTC T | 104 | TGT CCA TCT TGT CGT CTT CG | 105 | /56-FAM/TGA AGC AGG/ZEN/GAT GAC TCT GGG AGA/ 31ARFQ/ |
| AR Variant 12 SET 1 | Pr | 106 | GCT CAC CAT GTG TGA CTT GA | 107 | TGG GAG AGA GAC AGC TTG TA | 108 | /56-FAM/TGA TTG CGA/ZEN/GAG AGC TGC ATC AGT/ 31ARFQ/ |
| AR Variant 12 SET 4 | Pr | 109 | GAA AGT CCA CGC TCA CCA T | 110 | GCA GCC TTG CTC TCT AGC | 111 | /56-FAM/TGA TTG CGA/ZEN/GAG AGC TGC ATC AGT/ 31ARFQ/ |
| UGT2615 SET 1 (7366) | Pr | 112 | CTC TGC ACA AAC TCT TCC ATT TC | 113 | TTT CCT CGC CCA TTC TTA CC | 114 | /56-FAM/TTG GCT GGT/ZEN/TTA CAG TGA AGT CCT CC/31ARFQ/ |
| UGT2B15 SET 5 | PR | 115 | GGA AGG AGG GAA CAG AAA TCC | 116 | GTG AGC TAC TGG CTG AAC TAT T | 117 | /56-FAM/TGG CTA CAC/ZEN/ATT TGA GAA GAA TGG TGG A/31ARFQ/ |
| AFP SET 1 (174) | Li | 118 | AGG AGA TGT GCT GGA TTG TC | 119 | TCT GCA TGA ATT ATA CAT TGA CCAC | 120 | /56-FAM/AAT GCT GCA/ZEN/AAC TGA CCA CGC TG/31ABkFQ/ |
| AFP SET 2 | Li | 121 | ACT GCA GAG ATA AGT TTA GCT GAC | 122 | TCA CCA TTT TGC TTA CTT CCT TG | 123 | /56-FAM/TTG CCC AGT/ZEN/TTG TTC AAG AAG CCA C/31ABkFQ/ |
| STEAP2 (261729) | Br, Lu, Pr, Panc | 124 | CAT GTT GCC TAC AGC CTC T | 125 | TCT CCA AAC TTC TTC CTC ATT CC | 126 | /56-FAM/ACA TGG CTT/ZEN/ATC AGC AGG TTC ATG CA/31ABkFQ/ |
| TEAD3 (7005) | Br, Lu, Li | 127 | GAA GAT CAT CCT GTC AGA CGA G | 128 | CTT CCG AGC TAG AAC CTG TAT G | 129 | /56-FAM/AGC GTG CAA/ZEN/TCA ACT CAT TTC GGC/ 31ABkFQ/ |
| TFAP2C (7022) | Br, Lu, MeI | 130 | GAT CAG ACA GTC ATT CGC AAA G | 131 | GAC AAT CTT CCA GGG ACT GAG | 132 | /56-FAM/ACA GGG GAG/ZEN/GTT CAG AGG GTT CTT/ 31ABkFQ/ |
| TMPRSS 2 (7113) | Pr | 133 | CCC AAC CCA GGC ATG ATG | 134 | TCA ATG AGA AGC ACC TTG GC | 135 | /56-FAM/ACC CGG AAA/ZEN/TCC AGC AGA GCT/31ABkFQ/ |
| GPC3 (2719) | Li | 136 | TGC TGG AAT GGA CAA GAA CTC | 137 | GCT CAT GGA GAT TGA ACT GGT | 138 | /56-FAM/TCC TTG CTG/ZEN/CCT TTT GGC TGT ATC T/31ABkFQ/ |

TABLE 3-continued

| Gene | Disease Group | Seq ID | Primer 2 | Seq ID | Primer 1 | Seq ID | Probe |
|------|---------------|--------|----------|--------|----------|--------|-------|
| ALB (219) | Li | 139 | CTT ACT GGC GTT TTC TCA TGC | 140 | CCA ACT CTT GTA GAG GTC TCA AG | 141 | /56-FAM/ACA TTT GCT/ZEN/GCC CAC TTT TCC TAG GT/31ABkFQ/ |
| G6PC SET 1 (2538) | Li | 142 | GGA CCA GGG AAA GAT AAA GCC | 143 | GCA AGG TAG ATT CGT GAC AGA | 144 | /56-FAM/ACA GCC CAG/ZEN/AAT CCC AAC CAC AAA/31ABkFQ/ |
| G6PC SET 2 | Li | 145 | CAT TTT GTG GTT GGG ATT CTG G | 146 | GAT GCT GTG GAT GTG GCT | 147 | /56-FAM/CTG TCA CGA/ZEN/ATC TAC CTT GCT GCT CA/31ABkFQ/ |
| PRAME (23532) | MeI | 148 | GCC TTG CAC TTC CAT TAT GAC | 149 | CTC TGC ATT TTT GGA CAT AGG AG | 150 | /56-FAM/CAA GCG TTG/ZEN/GAG GTC CTG GG C/31ABkFQ/ |
| AHSG (197) | Li | 151 | ATG TGG AGT TTA CAG TGT CTG G | 152 | AGC TTC TCA CTG AGT GTT GC | 153 | /56-FAM/CCA CAG AGG/ZEN/CAG CCA AGT GTA ACC/31ABkFQ/ |
| GPR143 (4935) | MeI | 154 | ACG GCT CCC ATC CTC CT | 155 | CCA CTA TGT CAC CAT GTA CCT G | 156 | /56-FAM/TTC GCC ACG/ZEN/AGA ACC AGC AGC/31ABkFQ/ |
| PTPRZ1 (5803) | MeI | 157 | TGC TCT GAC AAC CCT TAT GC | 158 | GGC TGA GGA TCA CTT TGT AGA | 159 | /56-FAM/AGG CCAGGA/ZEN/GTCTTT GCT GAC ATT/31ABkFQ/ |
| MUCL1 (118430) | Br | 160 | CAT CAG CAG GAC CAG TAG C | 161 | TGT CTG TGC TCC CTG ATC T | 162 | /56-FAM/ACT CCC AAG/ZEN/AGT ACC AGG ACT GCT/31ABkFQ/ |
| PIP (5304) | Br | 163 | TCA TTT GGA CGT ACT GAC TTG G | 164 | CTT GCT CCA GCT CCT GTT C | 165 | /5HEX/CCT GCT CCT /ZEN/GGT TCT CTG CCT G/31ABkFQ/ |
| PGR (5241) | Br | 166 | GGT GTT TGG TCT AGG ATG GAG | 167 | ACT GGG TTT GAC TTC GTA GC | 168 | /56-FAM/AGT GGG CAG/ZEN/ATG CTG TATTTT GCAC/31ABkFQ/ |
| TFAP2C (7022) | Br, Lu | 169 | GTG ACT CTC CTG ACA TCC TTA G | 170 | CCA TCT CAT TTC GTC CTC CAA | 171 | /56-FAM/TTC GGC TTC/ZEN/ACA GAC ATA GGC AAA GT/31ABkFQ/ |
| SCGB2A1 (4246) | Br | 172 | ACT CTG AAA AAC TTT GGA CTG ATG | 173 | TCT AGC AAT CAA CAG ATG AGT TCT | 174 | /56-FAM/TAG CCC TCT/ZEN/GAG CCA AAC GCC/31ABkFQ/ |
| FAT1 (2195) | Br, Lu, Pr | 175 | AGC TCC TTC CAG TCC GAAT | 176 | GTC TGC TCA TCA ATC ACC TCA | 177 | /56-FAM/ATC CCA GTG/ZEN/ATA CCC ATT GTC ATC GC/31ABkFQ/ |
| FAT2 (2196) | Br, Lu, Pr | 178 | GGA CAG AGA GAA CAA GGA TGA AC | 179 | TGT GGG AGA ATA TAG GTG GAT TG | 180 | /56-FAM/TGG AGG TGA/ZEN/CTG TGC TGG ACA ATG/31ABkFQ/ |
| RND3 (390) | Br, Lu | 181 | GCT TTG ACA TCA GTA GAC CAG AG | 182 | CTG TCC GCA GAT CAG ACT TG | 183 | /56-FAM/ACA GTG TCC/ZEN/TCA AAA AGT GGA AAG GTG A/31ABkFQ/ |
| SFTPB (6439) | Lu | 184 | CCT GGA AAA TGG CCT CCT T | 185 | CAT TGC CTA CAG GAA GTC TGG | 186 | /56-FAM/CCG ATG ACC/ZEN/TAT GCC AAG AGT GTG AG/31ABkFQ/ |

TABLE 3-continued

| Gene | Disease Group | Seq ID | Primer 2 | Seq ID | Primer 1 | Seq ID | Probe |
|---|---|---|---|---|---|---|---|
| SCGB3A2 (117156) | Lu | 187 | CCA GAG GTA AAG GTG CCA AC | 188 | TCC CAG ATA ACT GTC ATG AAG C | 189 | /56-FAM/AAG GCA GTA/ZEN/GCA GAG TAA CTA CAA AGG C/31ABkFQ/ |
| SERPINA3 (12) | Br, Lu | 190 | CCT CAA ATA CAT CAA GCA CAG c | 191 | GGA AGC CTT CAC CAG CAA | 192 | /56-FAM/TAG CAG TCT/ZEN/CCC AGG GG TCC A/31ABkFQ/ |
| SFRP2 (6423) | Br, Lu | 193 | TTG CAG GCT TCA CAT ACC TT | 194 | GCC CGA CAT GCT TGA GT | 195 | /56-FAM/TTT CCC CCA/ZEN/GGA CAA CGA CCT TT/31ABkFQ/ |
| CRABP2 (1382) | Br, Lu | 196 | CTC TTG CAG CCA TTC CTC TT | 197 | CCC TTA CCC CAG TCA CTT CT | 198 | /56-FAM/TTT CTT TGA/ZEN/CCT CTT CTC TCC TCC CCT/31ABkFQ/ |
| AQP4 (361) | Lu | 199 | TGG ACA GAA GAC ATA CTC ATA AAG G | 200 | GGT GCC AGC ATG AAT CCC | 201 | /56-FAM/CCG ATC CTT/ZEN/TGG ACC TGC AGT TAT CA/31ABkFQ/ |
| TMPRSS4 (56649) | Br, Lu | 202 | ATC TTC CCT CCA TTC TGC TTC | 203 | CAG TTC CCA CTC ACT TTC TCA G | 204 | /56-FAM/CTC ACT CCA/ZEN/GCO ACC CCA CTC/31ABkFQ/ |
| GREM1 (26585) | Lu | 205 | TTT TGC ACC AGT CTC GCT T | 206 | GCC GCA CTG ACA GTA TGA G | 207 | /56-FAM/CCT ACA CGG/ZEN/TGG GAG CCC TG/31ABkFQ/ |
| FOXF1 (2294) | Lu | 208 | CGA CTG CGA GTG ATA CCG | 209 | CTC TCC ACG CAC TCC CT | 210 | /56-FAM/CTG CAC CAG/ZEN/AAC AGC CAC AAC G/31ABKFQ/ |
| NKX2-1 (7080) | Lu | 211 | TGC CGC TCA TGT TCA TGC | 212 | CAG GAC ACC ATG AGG AAC AG | 213 | /56-FAM/CCC GCC ATC/ZEN/TCC CGC ITC A/31ABkFQ/ |
| NKX2-1 (7080) | Lu | 214 | AAG ATG TCA GAC ACT GAG AAC G | 215 | CGA AGC CCG ATG TGG TC | 216 | /56-FAM/ATG TCG ATG/ZEN/AGT CCA AAG CAC ACG A/31ABkFQ/ |
| AFP (174) | Li | 217 | AGGAGATGTGCTGG ATTGTC | 218 | TCTGCATGAATT ATACATTGAC CAC | 219 | /56-FAM/AAT GCT GCA/ZEN/AAC TGA CCA CGC TG/31ABkFQ/ |
| AHSG (197) | Li | 220 | ATGTGGAGTTTACA GTGTCTG G | 221 | AGCTTCTCACTG AGTGTTGC | 222 | /56-FAM/CCA CAG AGG/ZEN/CAG CCA TA ACC/31ABKFQ/ |
| ALB (213) | Li | 223 | GAG ATC TGC TTG AAT GTG CTG | 224 | CAA CAG AGG TTT TTC ACA GCA T | 225 | /56-FAM/AGA TAT ACT/ZEN/TGG CAA GGT CCG CCC/31ABkFQ/ |
| ALB (213) | Li | 226 | CAT GGT AGG CTG AGA TGC TTT | 227 | GAC GAT AAG GAG ACC TGC TTT G | 228 | /56-FAM/ACT TGT TGC/ZEN/TGC AAG TCA AGCTGC/31ABkFQ/ |
| ALB (213) | Li | 229 | GCG CAT TCT GGA ATT TGT ACT C | 230 | GCT ATG CCA AAG TGT TCG ATG | 231 | /56-FAM/ACC TCT TGT/ZEN/GGA AGA GCC TCA GAA/31ABkFQ/ |
| APOH (350) | Li | 232 | TGA TGG ATA TTC TCT GGA TGG C | 233 | CCT GAA TCT TTA CTC TCT CTC CTT G | 234 | /56-FAM/CCA GTT TCC/ZEN/CAG TTT GGT ACA TTC TAT TTC TTC C/31ABkFQ/ |

TABLE 3-continued

| Gene | Disease Group | Seq ID | Primer 2 | Seq ID | Primer 1 | Seq ID | Probe |
|---|---|---|---|---|---|---|---|
| FABP1 (2168) | Li | 235 | GCA CTT CAA GTT CAC CAT CAC | 236 | ACC AGT TTA TTG TCA CCT TCC A | 237 | /56-FAM/AAC CAC TGT/ZEN/CTT GAC TTT CTC CCC TG/31ABkFQ/ |
| FGB (2244) | Li | 238 | ACA TCT ATT ATT GCT ACT ATT GTG TGT 1 | 239 | TGG GAG CCT CTT CTC TCT TC | 240 | /56-FAM/ACC CTC CTC/ZEN/ATT GTC GTT GAC ACC/31ABKFQ/ |
| FGG (2266) | Li | 241 | TTC ATT TGA TAA GCA CAC AGT CTG | 242 | ACC TTG AAC ATG GCATAG TCT G | 243 | /56-FAM/TGC CAT TCC/ZEN/AGT CTT CCA GTT CCA/31ABkFQ/ |
| GPC3 (2719) | Li | 244 | AATCAGCTCCGCTT CCTTG | 245 | TGCTTATCTCGT TGTCCTTCO | 246 | /56-FAM/TTC CAG GCG/ZEN/CAT CAT CCA CAT CC/31ABkFQ/ |
| RBP4 (5950) | Li | 247 | CAG AAG CGC AGA AGA TTG TAA G | 248 | TCT TTC TGA TCT GCC ATC GC | 249 | /56-FAM/AGG CTG ATC/ZEN/GTC CAC AAC GGT T/31ARFQ/ |
| TF (7018) | Li | 250 | AGA AGC GAG TCC GAC TGT | 251 | CAC TGC ACA CCA TCT CAC A | 252 | /56-FAM/CCA GACACA/ZEN/GCCCCA GGA CG/31ARFQ/ |

Note that PRAME is also named MAPE (Melanoma Antigen Preferentially Expressed In Tumors), OIP4 (Opa-Interacting Protein OIP4), and CT130 (Cancer/Testis Antigen 130).

The following Table 4 lists nested primers designed to specifically pre-amplify the regions targeted by primers listed in Table 3.

TABLE 4

| Primer name | Seq ID | Nested Forward | Seq ID | Nested Reverse |
|---|---|---|---|---|
| FAT1 | 253 | CAG ATG GAG GAG GAA GAT TCT G | 254 | GTA TAC TGC CTG GAG TTC TCT G |
| FAT2 | 255 | CTG GTT CAG GTC TCC ATT ACA G | 256 | GCT GTG ACT CTG AGC AAG TA |
| AGR2 | 257 | TGT CCT CCT CAA TCT GGT TTA TG | 258 | GAC AGA AGO OCT TGG AGA TTT |
| PKP3 | 259 | CGG TGG CGT TGT AGA AGA T | 260 | AGA AGA TCT CTG CCT CCG A |
| RND3 | 261 | CAA GAT AGT TGT GGT GGG AGA c | 262 | AGG GTC TCT GGT CTA CTG ATG |
| TFAP2C | 263 | TTTGGATTTACCGCTTGGG | 264 | GACTCCAGTGTGGGAGAG |
| S100A2 | 265 | GGG CCC ACA TAT AAA TCC TCA c | 266 | CTG CTG GTC ACT GTT CTC ATC |
| PRAME | 267 | CTTCGCGGTGTGGTGAA | 268 | GCTGTGTCTCCCGTCAAA |
| PIP | 269 | CTG GGA CAC ATT GCC TTC T | 270 | CCA CCA TGC ATT CTT TCA ATT CT |
| PGR | 271 | AAA CCC AGT TTG AGO AGA TGA G | 272 | CCC TGC CAA TAT CTT GGG TAA T |
| SCGB2A1 | 273 | ACA GCA ACT TCC TM ATC CC | 274 | GCG GCA TCA CTG TCT ATG AA |
| MUCL1 | 275 | CCT TGC CTT CTC TTA GGC TTT | 276 | AGC AGT GGT UC AGC ATC A |
| PGR | 277 | CAG ATA ACT CTC ATT CAG TAT TCT TGG | 278 | CTC TAA TGT AGC TTG ACC TCA TCT |

TABLE 4-continued

| Primer name | Seq ID | Nested Forward | Seq ID | Nested Reverse |
|---|---|---|---|---|
| TFAP2C | 279 | GAG AAG TTG GAC AAG KFT GGG | 280 | GCT GAG AAG UC TGT GAA TTC TTT A |
| SCGB2A1 | 281 | GTT TCC TCA ACC AGT CAC ATA GA | 282 | ACT TGT CTA GCA GTT TCC ACA TA |
| FAT1 | 283 | GGG AAA GCC TGT CTG AAG TG | 284 | TCG TAG CCT CCA GGG TAA TAG |
| FAT2 | 285 | GTT ACA GGT CTC CTA TCT ACA GC | 286 | GCT CAG CCT CTC TGG AAG |
| RND3 | 287 | CTC TCT TAC CCT GAT TCG GAT G | 288 | GGC GTC TGC CTG TGA TT |
| SFTPB | 289 | CCT GAG UC TGG TGC CAA AG | 290 | GGG CAT GAG CAG MT CAA |
| SCGB3A2 | 291 | CCA CTG OCT TGG TGG ATT T | 292 | TCA ACA GAA ATG CCC AGA GTT |
| SERPINA3 | 293 | CTT CTC CAG CTG GGC ATT | 294 | TGC TGT GGC AGC AGA TG |
| SFRP2 | 295 | CGG TCA TGT CCG CCT TC | 296 | GCG UT CCA TTA TGT CGT TGT c |
| CRABP2 | 297 | CCC TCC UC TAG GAT AGC G | 298 | AAC CCG GAA TGG GTG AT |
| AQP4 | 299 | AAACGGACTGATGTCACTGG | 300 | TGGACAGAAGACATACTCAT AAAGG |
| TMPRS S4 | 301 | CCCACTGCTTCAGGAAACATA | 302 | GTCAGACATCTTCCCTCCATT C |
| GREM1 | 303 | GCCGCACTGACAGTATGA | 304 | CAGAAGGAGCAGGACTGAAA |
| FOXF1 | 305 | AGC GGC GCC TCT TAT ATC | 306 | GCG TTG AAA GAG AAG ACA AAC T |
| NKX2-1 | 307 | CTA CTG CAA CGG CAA CCT | 308 | GGG CCA TGT TCT TGC TCA |
| NKX2-1 | 309 | CAG ACT CGC TCG CTC ATT T | 310 | CCT CCA TGC CCA CTT TCT 1 T |
| PIP | 311 | CCCAAGTCAGTACGTCCAAAT | 312 | GCCTAATTCCCGAATAACATC AAC |
| AGR2 | 313 | GCT TTA AAG AAA GTG TTT GCT G | 314 | CTG TAT CTG CAG GTT CGT AAG |
| SOX10 | 315 | AAG TTC CCC GTG TGC ATC | 316 | CTC AGC CTC CTC GAT GAA |
| MAGEA6 | 317 | GTGAGGAGGCAAGGTTCTG | 318 | GGCTCCAGAGAGGGTAGTT |
| TFAP2C | 319 | TTTGGATTTACCGCTTGGG | 320 | GACTCCAGTGTGGGAGAG |
| PRAME | 321 | CTTCGCGGTGTGGTGAA | 322 | GCTGTGTCTCCCGTCAAA |
| GPR143 | 323 | ATC CTG CTG TAT CAC ATC ATG | 324 | CTG ACA GGT TTC AAA GAA CCT |
| PMEL | 325 | CCAGTGCCTTTGGTTGCT | 326 | CAAGAGCCAGATGGGCAAG |
| MLANA | 327 | TGCCAAGAGAAGATGCTCAC | 328 | CATTGAGTGCCAACATGAAG AC |
| PTPRZ1 | 329 | AAG AAG CTG CCA ATA GGG AT | 330 | TGT CCA GAG AGG TGG ATG |

Multiplex Digital Analysis of Gene Transcripts from CTC-Chip Products

To improve the detection of tumor-specific mRNA from minimal amounts of RNA derived from CTCs, we established a multiplex assay capable of testing many different gene transcripts from a minute amount of CTC-Chip product. This combines the higher sensitivity/specificity of using multiple independent genes, with the fact that the amount of input template is limited (and hence should not be diluted into multiple reactions). Our assay includes 4 genes per reaction, with each gene being resolved uniquely in 2-dimensional space by selecting different ratios of fluorescent conjugated primers. Thus, in a single reaction, we can independently measure 4 gene transcripts without having to dilute the template. For different cancers, we have gone as far as up to 4 different reactions (i.e., up to 20 different gene transcripts), and with application of nested RT-PCR digital assays, there is no limit to the number of reactions that can be performed.

This multiplex strategy achieves the ideal balance between analyzing multiple transcripts (and hence ensuring against heterogeneous variation in cancer cell expression patterns), but not diluting the input material by performing multiple independent PCR reactions. Depending on tumor types and the number of genes required for optimal signal, we have developed assays ranging from 2-4 multiplex reactions (each multiplex reaction testing for 4-genes). Thus, without undue dilution of input template, we can interrogate the product of a single CTC for expression of anywhere from 8 to 16 different genes. It is important to the assay to be able to add the signal from all of these genes (i.e. cumulative signal), while also having individual gene results (to optimize signal/noise at the individual gene level, and also gather information from specific signaling pathways that each gene interrogates—for example androgen signaling in prostate CTCs).

To display the results of the multiplex reaction in a single view (and hence differentiate amplification of each gene is isolation), we varied the concentrations of the two fluorescent probes (FAM (blue) and HEX (green)). By doing this, each individual gene amplification reaction has a unique combination of FAM/HEX signal that reflects the composition of the gene-specific primers, and hence identifies the gene-specific PCR product. In 2-dimensional space, we can illustrate the signal position of 4 different gene amplification products produced from a single multiplex reaction. As applied to digital PCR using droplets to encapsulate each PCR reaction, this method separates the targets into individual clusters by modifying the binary signal amplitude of positive droplets, which are displayed quantitatively. As predicted, this method allows both cumulative scoring of total signal for multiple genes (e.g., 16 markers in a total of 4 reactions), while also retaining the ability to quantify the signal from each individual gene target.

Novel Gene Panels to Enable Lineage-Specific Prediction of the Potential Efficacy for Specific Anti-Cancer Treatment Regimens Virtually all patients with metastatic prostate cancer experience an initial clinical response following androgen deprivation therapy (ADT). As tumors develop castration-resistance, half of patients have a sustained second remission following treatment with the potent androgen synthesis inhibitor abiraterone (e.g., ZYTIGA®), while others have only a short response and would hence benefit from alternative or combination therapies. To test whether CTC-derived signatures provide predictive markers of response to anti-androgen therapies after ADT, we prospectively evaluated 25 patients with metastatic CRPC who were initiating abiraterone therapy in the first-line setting.

Remarkably, an elevated CTC-Score at pretreatment baseline was predictive of early progression, an effect that was driven by expression of FOLH1 (PSMA) and HOXB13 within CTCs. Both of these markers have been associated with aberrant androgen receptor ("AR") signaling, and HOXB13 has been associated with more aggressive, hormone refractory, prostate cancer. The correlation between HOXB13 and FOLH1 CTC-derived signal was evident for radiographic progression-free survival (HOXB13, $P=0.015$; FOLH1, $P=0.015$), as well as overall survival (HOXB13, $P=0.017$; FOLH1, $P=0.017$). In contrast, the pretreatment serum PSA protein level is correlated with reduced overall survival, but it is not indicative of radiographic progression-free survival or PSA progression, and it is no longer correlated with outcome following initiation of treatment.

Applications of the d-CTC Assay Methods

The early detection of epithelial cancers at a time when they can be surgically resected or irradiated provides the best chance of cure, and the administration of adjuvant chemotherapy in the setting of minimal cancer dissemination is far more effective in achieving cure than the treatment of established metastatic disease. Just as important as early detection is to select a proper anti-cancer therapy. The new methods described herein use the d-CTC assay methods to not only provide early detection of a specific type of cancer, but in combination with the appropriate reference standards, can be used to determine and compare the predicted efficacy of different therapeutic regimens in a specific patient depending on his or her tumor gene expression profile.

The d-CTC assays described herein can be used for both initial screening and to determine the best therapeutic regimen. The use of the new d-CTC assays described herein, in which each CTC (no matter how intact or pre-apoptotic) can give rise to hundreds of molecular signals, dramatically enhances the ability to detect and monitor CTCs in patients with known cancer, and to quantitatively monitor and analyze their response to therapeutic interventions. Beyond scoring for cell numbers through molecular markers, specific interrogation of mutations or cancer-associated rearrangements (e.g., EML4-ALK in lung cancer) can be achieved with comparable sensitivity.

As discussed in the examples below, the new methods described herein are illustrated in prostate cancer, where the analysis demonstrated that an elevated CTC-Score at pretreatment baseline was predictive of early progression, an effect that was driven by expression of FOLH1 (PSMA) and HOXB13 within CTCs.

EXAMPLES

The invention is further described in the following examples, which do not limit the scope of the invention described in the claims.

Example 1—Materials and Methods

The following materials and methods were used in the Examples set for the below.

Digital CTC Assay Protocol

This example provides a general digital CTC assay protocol that can be used for the methods described herein. Different aspects of this general protocol were used in Example 2 below.

1. Patient blood is run through I-Chip, version 1.3M or 1.4.5T. Sample is collected in a 15 mL conical tube on ice.

2. Sample is spun down at 4 C. Supernatant is decanted and SUPERase™ In (DTT independent RNAse inhibitor)+RNALater® Stabilization Solution (prevents RNA degradation by inhibiting RNAses) is added to the pellet. Sample is flash frozen and placed at −80 until further processing. Samples are stable at −80.

3. There are two different processing protocols for RNA purification to cDNA synthesis that were used in the examples described below.

Approach 1
 a. Sample was thawed on ice.
 b. Direct lysis of sample using detergents (NP40, Tween20).

c. Lysed sample was taken straight for cDNA synthesis (Superscript
d. After cDNA synthesis sample was purified via SPRI (Agencourt AMPure® XP beads) clean-up to clean up detergents and any nucleotides <100 bps.

Approach 2 a. Sample was thawed on ice.
b. Sample was processed on RNeasy Qiagen Micro Kit. Protocol has some slight variations compared to traditional Qiagen recommendations. Higher volumes of Buffer RLT (Lysis buffer) were used as well as higher ETOH concentrations. These modifications were made because of RNALater® addition to the sample.
c. After cDNA synthesis—sample was purified via SPRI (Agencourt AMPure XP beads) clean-up to clean up detergents and any nucleotides <100 bps.

4. cDNA (synthesized from Approach 1 or 2) can be processed in two different ways:
   a. cDNA was used directly for ddPCR; or
   b. cDNA was amplified used a Fluidigm BioMark™ Nested PCR approach (primers from genes used for nested PCR have been pre-validated). Amplified cDNA was diluted.

5. cDNA (from step 4a or 4b), Biorad Supermix™ for probes, primer or primers (for gene of interest; up to 4 different primers (FAM and HEX) can be multiplexed) were added in a total volume of 22 µl.

6. Droplets were generated (~15,000-18,000 droplets per well).

7. Droplet Sample were put in a PCR machine. The PCR conditions were different than Biorad recommendations. We used a step-down rather than a slow ramp to ensure that all droplets reach the same temperature. This is different than what both RainDance and Biorad uses. Better results (i.e., more signal and more separation between positive and negative droplets) can be obtained with the step-down rather than the gradient.

8. After the PCR, positive droplets were counted in a ddPCR machine.

9. Data is collected and analyzed using TIBCO® Spotfire® analysis software.

The reagents, reagent concentrations, and reaction volumes are provided below:

Reagents:
Biorad ddPCR™ Supermix for Probes (No dUTP)
IDT primers/probes (20× or 40×)
cDNA (1 ng/ul for cell lines)
Nuclease free water
Eppendorf semi-skirted 96 well plate (Only these plates work with the machine)

Testing Relevant Cell Lines
Per Single Reaction:

| | |
|---|---|
| ddPCR Supermix | 11.0 µl |
| Primer (20x) | 1.10 µl |
| cDNA (1 ng/ul) | 1.10 µl |
| Water | 8.80 µl |
| TOTAL | 22.0 µl per well |

A master-mix containing ddPCR supermix, cDNA, and water were aliquoted into wells and 1.1 µl of each the primer was added to each well and mixed well.

Patient Samples
Per Single Reaction for Individual Genes

| | |
|---|---|
| ddPCR Supermix | 11.0 µl |
| Primer (20x) | 1.1 µl |
| cDNA (patient) | Up to 9.9 µl (Balance with water if less) |
| TOTAL | 22.0 µl per well |

Per Single Multiplexed Reaction for Multiple Genes

| | |
|---|---|
| ddPCR Supermix | 11.0 µl |
| Primer 1 (40x) | .55 µl |
| Primer 2 (40x) | .55 µl |
| Primer 3 (40x) | .55 µl |
| Primer 4 (40x) | .55 µl |
| cDNA (patient) | 8.8 µl |
| TOTAL | 22.0 µl per well |

When testing multiple patients against a gene-specific primer or multiplexing primers against multiple genes, a master-mix, which includes the ddPCR supermix and primers, was aliquoted into wells followed by addition of patient cDNA to each well and mixed well.

Patients and Clinical Specimens

Patients with a diagnosis of prostate cancer provided informed consent to one of two Institutional Review Board approved protocols, DF/HCC 05-300 or DF/HCC 13-209. Patients donated 20 mL of blood for CTC analysis, including patients with metastatic prostate cancer and patients with localized prostate cancer. Formalin-fixed, paraffin-embedded primary tumor tissues from patients were sectioned, and subjected to RNA extraction, prior to processing for droplet digital PCR (see below).

Circulating Tumor Cell Isolation

CTCs were isolated from fresh whole blood following leukocyte depletion using the microfluidic CTC-iChip as previously described. To maximize recovery of intact CTCs with high quality RNA, blood samples were processed within 4 hours of being collected from the patient. The total time for CTC isolation after receipt of fresh blood samples in the lab was approximately 2.5 hours. Briefly, whole blood samples were spiked with biotinylated antibodies against CD45 (R&D Systems, clone 2D1) CD66b (AbD Serotec, clone 80H3), and CD16 (Janssen Diagnostics), followed by incubation with Dynabeads MyOne Streptavidin T1 (Invitrogen) to achieve magnetic labeling and depletion of white blood cells. After processing of whole blood with the CTC-iChip and collecting the enriched CTC product on ice, cells were centrifuged at 4750 rpm and flash frozen in liquid nitrogen in the presence of RNAlater® (Ambion) to preserve RNA integrity.

Droplet Digital PCR

CTC samples were subjected to RNA extraction using the RNeasy Plus Micro Kit (Qiagen), followed by reverse transcription using SuperScript III First-Strand Synthesis System (Life Technologies). cDNA and primers/probes were combined with ddPCR Supermix for Probes (Bio-Rad) in a 96-well plate and loaded onto Bio-Rad's automated droplet generator. Droplets were amplified using a modified 45-cycle PCR with a 70° C. step-down in between the denaturation and annealing steps. Following thermal cycling, amplified droplets were detected via fluorescence with the QX200 Droplet Reader System (Bio-Rad).

A list of potential gene candidates was generated using publically available databases as well as single cell RNA-seq data. A two-step approach using both RT-PCR and ddPCR was developed to validate these genes. In the first step, cDNA prepared from healthy donor leukocytes and prostate cell lines (LNCaP, PC3, VCaP) was tested against primers using the ABI 7500 and Bio-Rad CFX96 Real-Time PCR Systems. Leukocytes were isolated from male healthy donors using BD Vacutainer® CPT™ Cell Preparation Tubes. Total RNA was extracted from isolated leukocytes and prostate cancer cell lines using RNeasy Micro Kit (Qiagen) and 500 ng reverse transcribed with SuperScript III First-Strand Synthesis System (Life Technologies). 1 ng of total cDNA was used per RT-PCR reaction. Genes expressed in cell lines and absent in healthy donor leukocytes by RT-PCR were further validated in a second step using ddPCR. cDNA prepared from CTC-iChip products of healthy donor males and patients was tested against genes using the ddPCR platform. Differential expression between healthy donors and patients determined by droplet count was used to select genes for the assay (Table 5).

TABLE 5

Sequences of Final Primers and Probes Used for Each Gene

| Gene | Forward 5'-3' | SEQ ID NO: |
|---|---|---|
| TMPRSS2 | TCA ATG AGA AGC ACC TTG GC | SEQ ID NO: 331 |
| FAT1 | ATC AGC AGA GTC AAT CAG TGA G | SEQ ID NO: 332 |
| KLK2 | GTC TTC AGG CTC AAA CAG GT | SEQ ID NO: 333 |
| STEAP2 | TCT CCA AAC TTC TTC CTC ATT CC | SEQ ID NO: 334 |
| KLK3 | GTG TGC TGG ACG CTG GA | SEQ ID NO: 335 |
| HOXB13 | CTG TAC GGA ATG CGT TTC TTG | SEQ ID NO: 336 |
| AGR2 | CAA TTC AGT CTT CAG CAA CTT GAG | SEQ ID NO: 337 |
| FOLH1 | TGT TCC AAA GCT CCT CAC AA | SEQ ID NO: 338 |

| Gene | Reverse 5'-3' | SEQ ID NO: |
|---|---|---|
| TMPRSS2 | CCC AAC CCA GGC ATG ATG | SEQ ID NO: 339 |
| FAT1 | GAT CCT TAT GCC ATC ACC GT | SEQ ID NO: 340 |
| KLK2 | GCT GTG TAC AGT CAT GGA TGG | SEQ ID NO: 341 |
| STEAP2 | CAT GTT GCC TAC AGC CTC T | SEQ ID NO: 342 |
| KLK3 | GTG ATA CCT TGA AGC ACA CCA TTA C | SEQ ID NO: 343 |
| HOXB13 | CAG CCA GAT GTG TTG CCA | SEQ ID NO: 344 |
| AGR2 | CTG ACA GTT AGA GCC GAT ATC AC | SEQ ID NO: 345 |
| FOLH1 | CAA TGT GAT AGG TAC TCT CAG AGG | SEQ ID NO: 346 |

| Gene | Probe 5'-3' | SEQ ID NO: |
|---|---|---|
| TMPRSS2 | ACC CGG AAA CC AGC AGA GCT | SEQ ID NO: 347 |
| FAT1 | TCT TGT CAG CAG CGT TCC CGG | SEQ ID NO: 348 |
| KLK2 | TGG CTA TTC TTC TTT AGG CAA TGG GCA | SEQ ID NO: 349 |
| STEAP2 | ACA TGG CTT ATC AGC AGG TTC ATG CA | SEQ ID NO: 350 |
| KLK3 | AAA GCA CCT GCT CGG GTG ATT CT | SEQ ID NO: 351 |
| HOXB13 | CAG CAT TTG CAG ACT CCA GCG G | SEQ ID NO: 352 |
| AGR2 | ATG CTT ACG AAC CTG CAG ATA CAG CTC | SEQ ID NO: 353 |
| FOLH1 | ATG AAC AAC AGC TGC TCC ACT CTG A | SEQ ID NO: 354 |

Cell Spiking

To test the limit of detection for the ddPCR assay a series of cell spiking experiments were performed using the CTC-iChip. Single LNCaP cells were manipulated using 10 um Eppendorf TransferMan® NK2 transfer tips into Kolliphor P188 buffer and spiked into healthy donor male blood. The spiked samples were prepped for processing as described above and run through the CTC-iChip. RNA and cDNA were isolated and prepped from the CTC-iChip products and run on ddPCR using Reactions 1 and 2.

Example 2—Generation of CTC Digital Signature Using Prostate-Lineage Transcripts Given the limitations inherent in fluorescence-based imaging and scoring of CTCs admixed with contaminating blood cells, we tested whether RNA-based digital PCR quantitation could provide a higher throughput, more sensitive and more specific readout. Microfluidic (CTC-iChip) depletion of hematopoietic cells from blood samples achieves $10^4$ to $10^5$ purification of CTCs, with approximately 500 WBCs remaining per 1 mL of processed whole blood. The high quality of RNA within the purified CTCs allows the application of new and highly robust digital droplet-PCR technologies, in which rare cDNA templates are encapsulated within lipid droplets, followed by PCR amplification and fluorescence scoring of positive droplets. The combination of microfluidic whole cell isolation of CTCs from blood and RNA-based digital PCR of CTC-derived transcripts (d-CTC assay) allows the use of prostate tissue lineage-specific mRNAs as highly specific markers to monitor metastatic prostate cancer (FIG. 1).

To test the application of this strategy for prostate CTC detection, we first identified a panel of prostate-specific transcripts whose expression is virtually absent in normal hematopoietic cells, even following high sensitivity droplet-PCR amplification. We selected multiple markers, both to address the known heterogeneity of prostate cancer cells, as well as to allow interrogation of cellular signaling pathways, including androgen receptor activity. We derived an initial set of 40 candidate genes, both from RNA sequencing of single prostate CTCs (Miyamoto, et al. Science 2015; 349: 1351-6.), as well as from publicly available expression databases.

Figure 2:
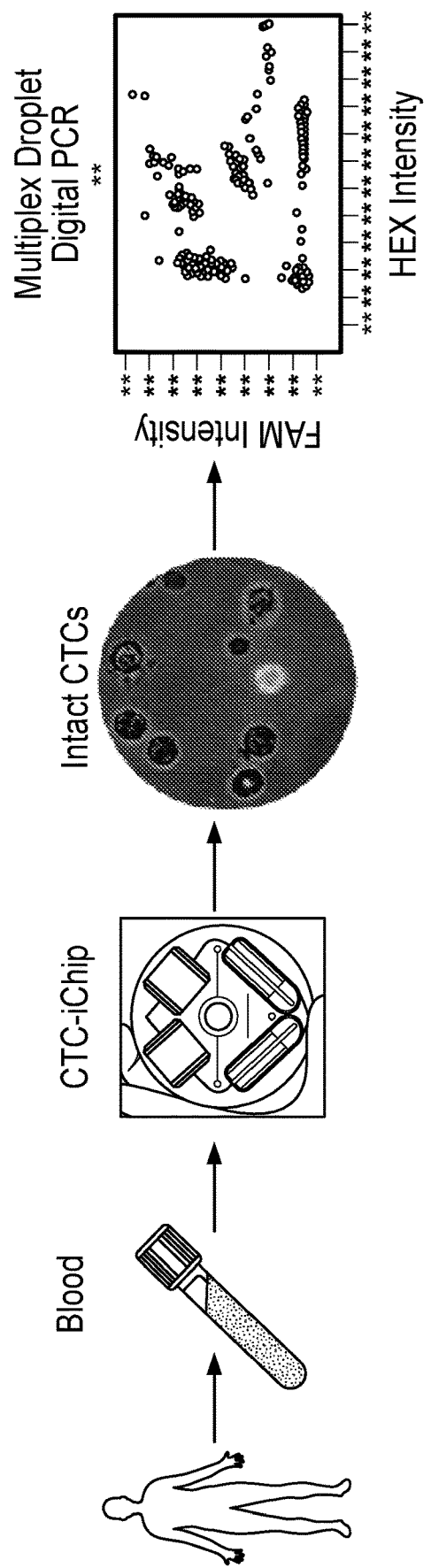
FIG. 2 is a schematic diagram showing a series of steps for obtaining intact CTCs from a patient blood sample, and then ending with a signal intensity plot that shows a d-CTC assay multiplexed for four different lineage specific transcripts to detect prostate cancer cell lines spiked into blood (shown as FAM label intensity vs. HEX label intensity).
Figure 3:
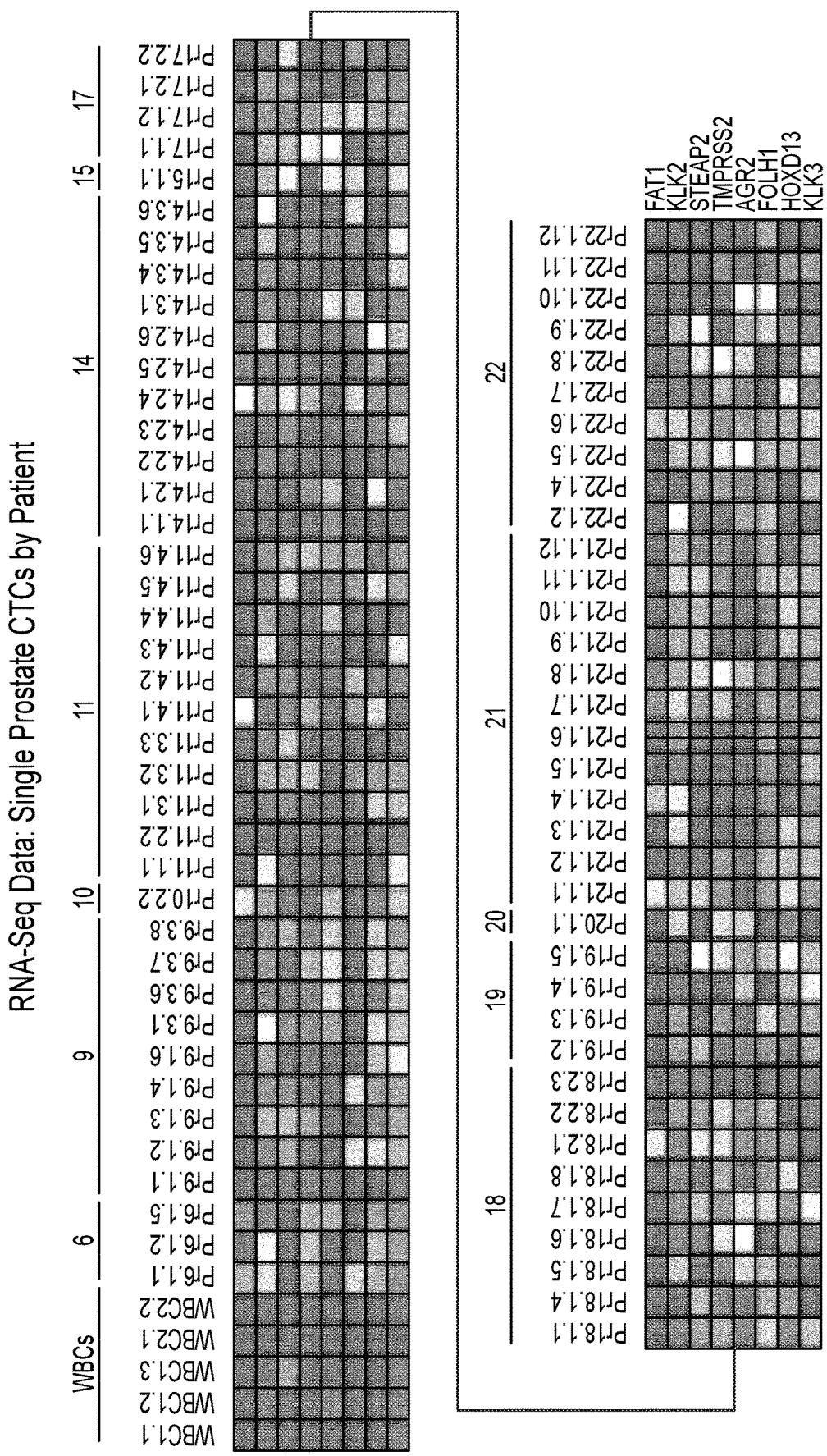
FIG. 3 is a single cell RNA-seq data showing the expression of final selected genes in white blood cells (WBC) and single prostate CTCs isolated from patients with metastatic prostate cancer.
Figure 5:
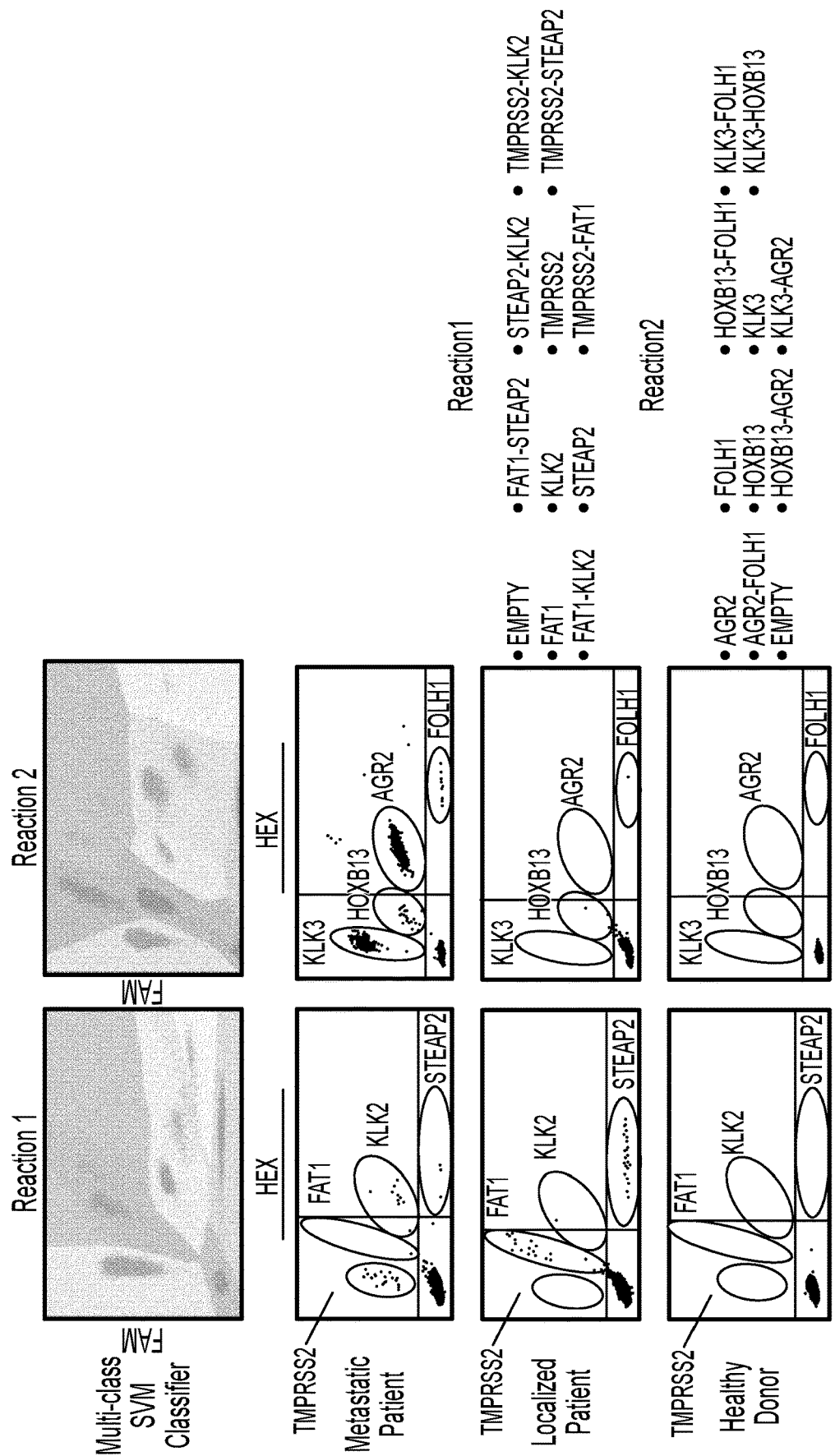
FIG. 5 is a multi-class support vector machine (SVM) classifier model that automatically classifies positive droplet signals. Representative multiplex ddPCR expression signal in CTCs from a metastatic prostate cancer patient, a localized prostate cancer patient, and a healthy donor.

Twenty-nine transcripts were identified as having high levels of expression in prostate tissue and/or prostate cancer, but without detectable RNA reads in normal blood cells contaminating the microfluidic CTC-iChip product (FIGS. 2 and 3). Multiple primers and conditions were optimized for a set of 8 genes, which together provided the most robust signal in rare prostate cancer cells admixed with normal blood cells. These genes included androgen responsive transcripts KLK3, KLK2, and TMPRSS2; androgen-repressed transcripts FOLH1 (PSMA) and HOXB13; and androgen-independent transcripts FAT1, AGR2, and STEAP2. To avoid dilution of rare templates while enabling amplification of multiple markers, we designed a multiplex assay (2 reactions with 4 genes per reaction), with differing relative ratios of FAM and HEX fluorescence to define the identity of the amplified product (FIG. 4). A multi-class support vector machine (SVM) classifier algorithm was developed to automatically classify droplets according to their position on the FAM-HEX coordinate system (FIG. 5).

Figure 6:
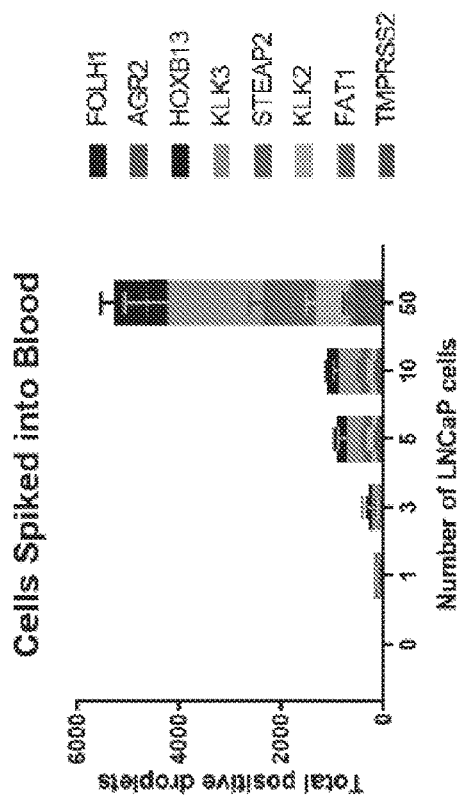
FIG. 6 is a graph of d-CTC assay signal for varying numbers of LNCaP cells micro-manipulated into healthy donor whole blood and processed using the CTC-iChip.

To validate the assay, we first micro-manipulated individual cells from the prostate cancer line LNCaP, and introduced these into 2.5 mL of whole blood from healthy donors, followed by processing through the CTC-iChip and droplet digital PCR quantitation. Introduction of a single LNCaP cell into a control blood sample generated 150 positive droplets (SD=65.3), with a progressive increase in signal as 3, 5, 10, and 50 cells were spiked into the blood samples (5562±1853 droplets for 50 prostate cell input) (FIG. 6). The distribution of signal among the 8 prostate-lineage transcripts remained comparable with increasing numbers of LNCaP cell input.

Example 3—CTC Scoring in Patients with Metastatic Prostate Cancer

Figure 7A:
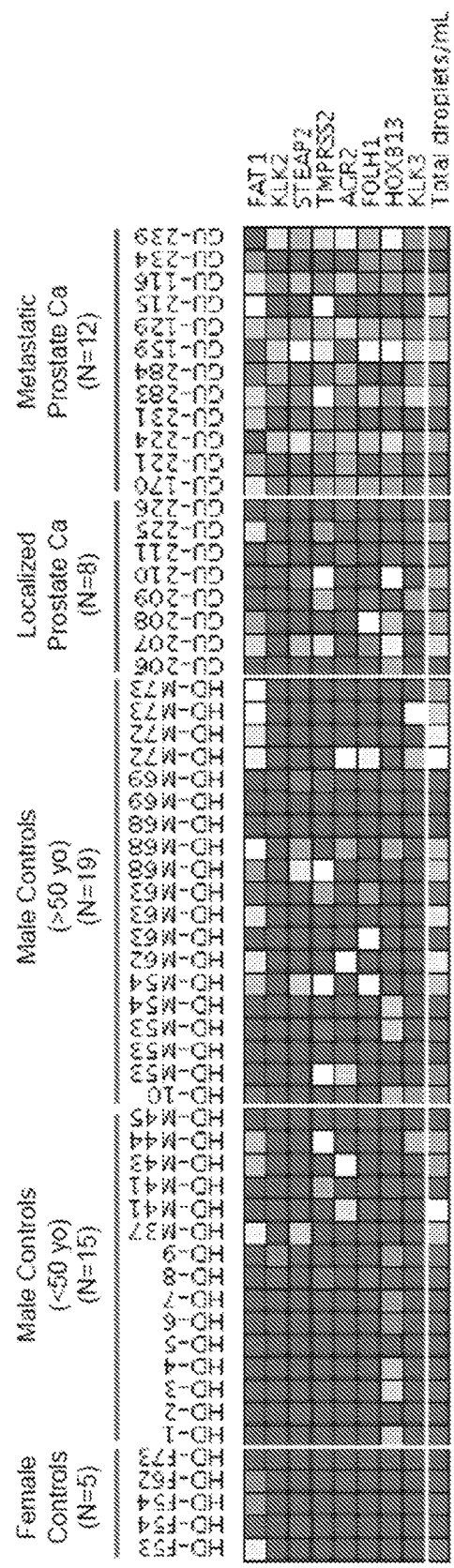

We tested the d-CTC detection strategy in 12 patients with metastatic prostate cancer, compared with 8 patients with localized prostate cancer, 34 male healthy blood donors (19>50 years old; 15<50 years old), and 5 female controls. The observed signal across all 8 markers is shown in FIG. 7A. Using the 19 age-matched male controls (>age 50) and 12 patients with metastatic prostate cancer, we established a signal threshold for each of the 8 genes at 2 standard deviations above the median in controls, and given the different signal intensity for each gene, we weighted each of these in proportion to the median difference between CRPC patients and age matched controls (see Example 1), thereby deriving a digital CTC-Score. A positive digital CTC-Score was present in $^{11}/_{12}$ (92%) patients with metastatic prostate cancer, compared with 0/34 healthy male blood donors (FIG. 7B). Under these stringent criteria, none of the 12 patients with localized prostate cancer had detectable CTC-Scores (FIG. 7B). Interestingly, while we established scoring criteria for highest specificity in monitoring patients with metastatic prostate cancer, low level digital signal was present in some individuals with localized cancer. Among healthy individuals, men >age 50 had higher background signal than those <age 50, and virtually no signal was present in female controls (FIG. 7B).

To compare the digital CTC assay with more traditional immunofluorescence-based detection of CTCs, pre-treatment blood samples were obtained from 25 patients with mCRPC enrolled on a prospective clinical trial of abiraterone in the first-line setting. Each blood sample was processed through the CTC-iChip and the output was equally divided between immunofluorescence-based microscopy scoring versus d-CTC assay. As expected, concordance between microscopic scoring and digital readouts was evident in samples with high numbers of CTCs, but the d-CTC assay was far more sensitive in identifying cases below microscopic detection, even using sophisticated multispectral fluorescence-based imaging. ($R^2$=0.01; P=0.6; FIG. 7C). Across patients with mCRPC in the first-line setting, the total digital CTC signal was moderately correlated with serum PSA protein measurements ($R^2$=0.16; P=0.049) (FIG. 7D). The levels of tumor-derived PSA protein in blood samples were also modestly correlated with the quantitation of CTC-derived KLK3 (PSA) mRNA ($R^2$=0.18; P=0.038; FIG. 7E). Taken all together, these observations indicate that the digital CTC-Score measures disease burden in patients with metastatic prostate cancer, but that by integrating multiple AR-dependent and independent transcripts within invasive tumor cells in the blood, it appears to provide information on disease status that is non-overlapping and potentially orthogonal to serum PSA protein measurements.

Figure 8E:
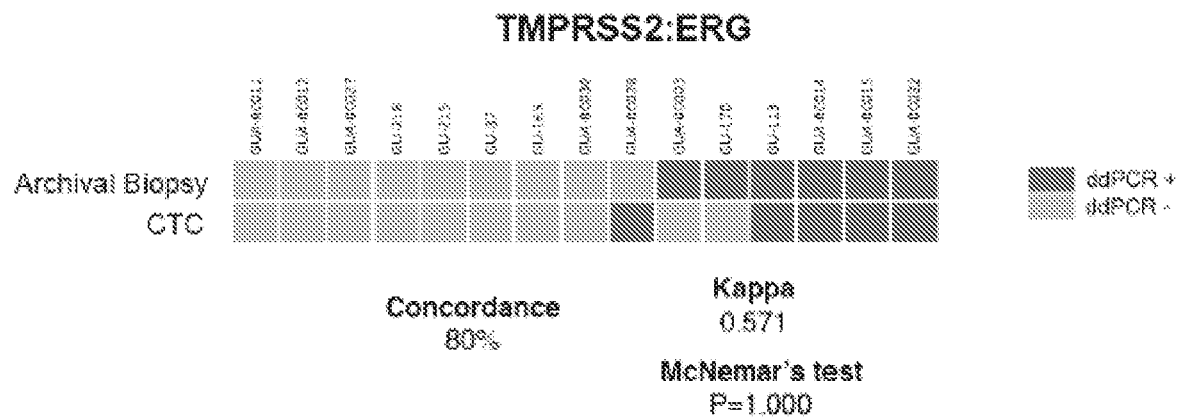
Figure 8F:
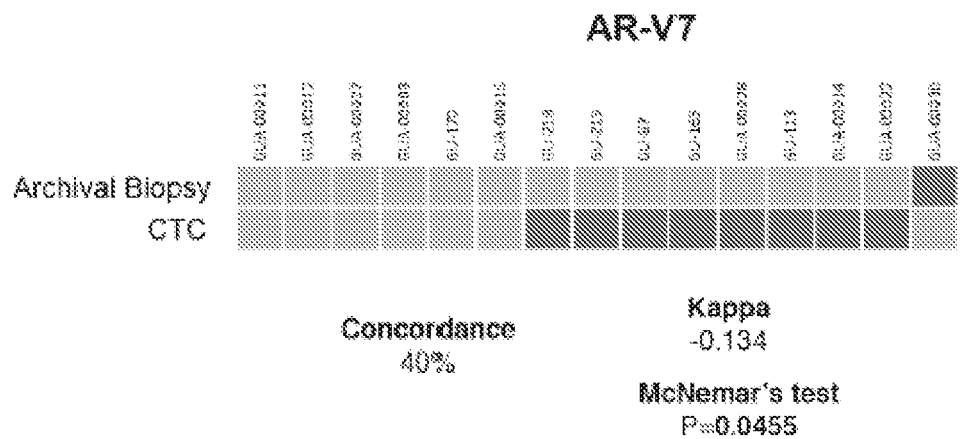

Example 4—Detection of AR-V7 and TMPRSS2-ERG Prostate Cancer Specific Transcripts in CTCs While recurrent missense mutations are rare in prostate cancer, two specific RNA fusion transcripts are characteristic of this tumor type. To complement the quantitation of prostate lineage-based transcripts in CTCs, we developed droplet PCR assays for both the TMPRSS2-ERG fusion transcript, which is present in 50% of cases, and the AR-V7 RNA splice variant, which constitutes a marker of resistance to anti-androgen therapy. Both tests were highly specific and sensitive when applied to prostate cell lines spiked into control blood specimens, followed by CTC-iChip purification (FIGS. 8A and 8B). When applied to blood samples from men with metastatic prostate cancer, 5 of 13 (38%) mCRPC patients had the TMPRSS2-ERG translocation, 11 (85%) had the AR-V7 splice variant, and 3 (23%) had both transcripts in their CTCs (FIG. 8C). Blood samples from 12 age-matched donors were negative for both transcripts (FIG. 8D). As expected, men whose CTCs were positive for TMPRSS2-ERG had archival primary tumors that were largely concordant for that marker (FIG. 8E). In contrast, the CTC-derived AR-V7 signal was virtually absent in matched primary prostate cancers (FIG. 8F), consistent with its characterization as a marker that emerges in the setting of advanced CRPC.

Example 5—Prospective Serial Monitoring of Patients on First-Line Abiraterone Therapy Virtually all patients with metastatic prostate cancer experience an initial clinical response following androgen deprivation therapy (ADT). As tumors develop castration-resistance, half of patients have a sustained second remission following treatment with the potent androgen synthesis inhibitor abiraterone, while others have only a short response and would hence benefit from alternative or combination therapies. To test whether CTC-derived signatures provide predictive markers of response to anti-androgen therapies after ADT, we prospectively evaluated 25 patients with metastatic CRPC who were initiating abiraterone therapy in the first-line setting.

Figure 9A:
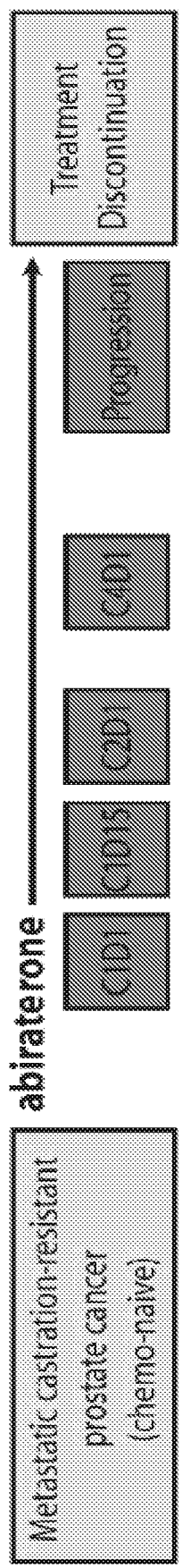
FIGS. 9A-9B show the results of a prospective study of first-line abiraterone therapy for prostate cancer patients.
Figure 9B:
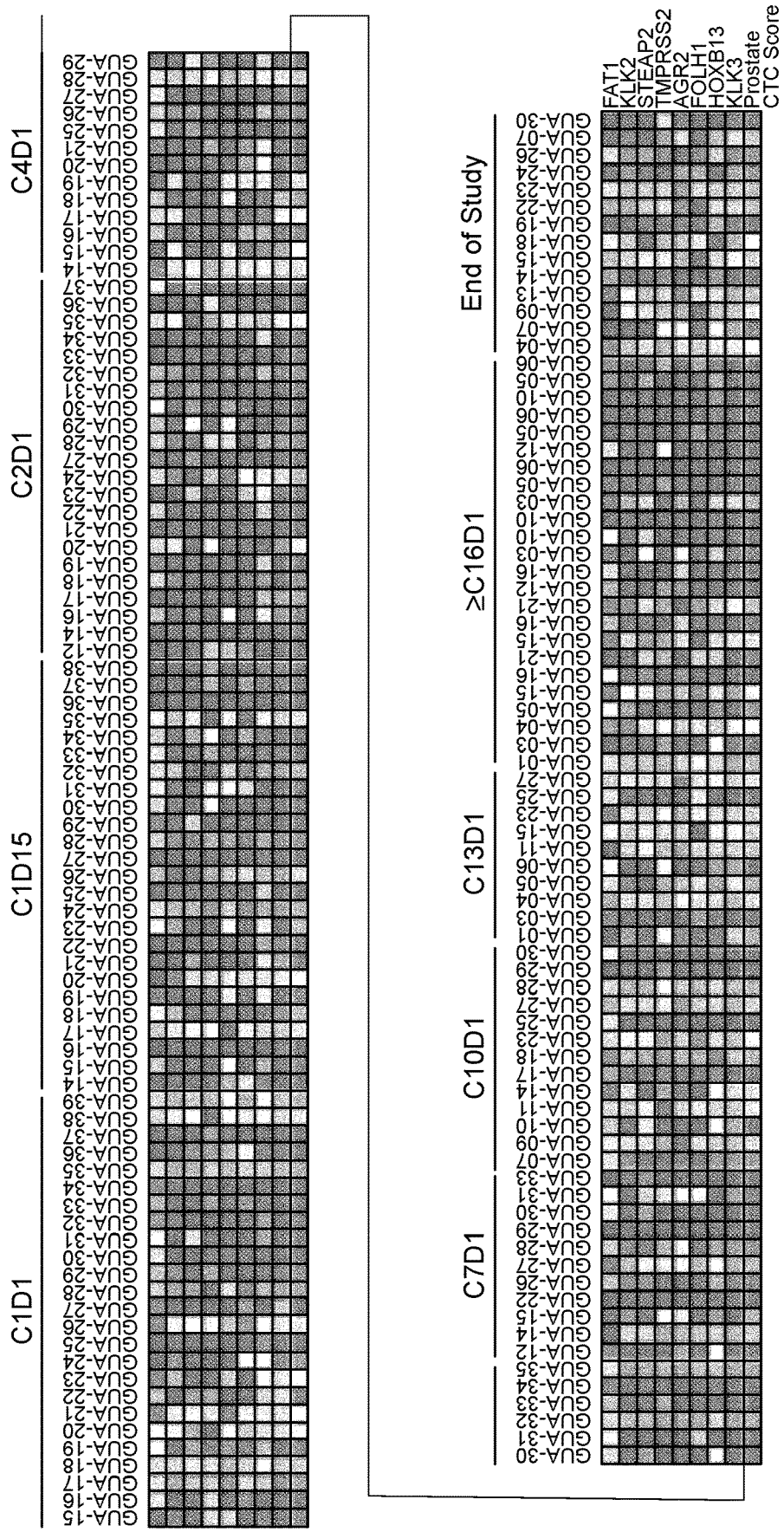

We first applied the prostate lineage CTC-Score at the baseline pretreatment time point (C1D1), at on-treatment time points of 2 weeks (C1D15), 4 weeks (C2D1), 12 weeks (C4D1), and at the time of disease progression and discontinuation of therapy (FIGS. 9A and 9B). Remarkably, an elevated CTC-Score at pretreatment baseline (C1D1) was predictive of early progression, an effect that was driven by expression of FOLH1 (PSMA) and HOXB13 within CTCs. Both of these markers have been associated with aberrant androgen receptor signaling, and HOXB13 has been associated with more aggressive, hormone refractory prostate cancer. The correlation between HOXB13 and FOLH1 CTC-derived signal was evident for radiographic progression (HOXB13, P=0.015; FOLH1, P=0.015), as well as overall survival (HOXB13, P=0.017; FOLH1, P=0.017). In contrast, the pretreatment serum PSA protein level is correlated with reduced overall survival, but it is not indicative of radiographic progression or PSA progression, and it is no longer correlated with outcome following initiation of treatment.

AR-V7 expression has been detected in patients with metastatic CRPC in the second line or greater setting, and it has been shown to predict acquired resistance to abiraterone when administered to patients with such advanced disease. Using the digital CTC assay, AR-V7 was detectable in 4/20 patients tested at the pretreatment baseline time point. In this first line setting, quantitative detection of AR-V7 was not predictive of radiographic progression or overall survival. However, serial monitoring of these patients indicated that the predictive value of AR-V7 increased during the first three courses of therapy, achieving a high predictive value for radiographic progression (P=0.026), and overall survival (P<0.001) using the 3-month time point. This observation is consistent with the initiation of anti-androgen therapy suppressing the proliferation of susceptible tumor cells, with the emergence of AR-V7-driven resistant disease in patients destined for early relapse. In contrast to AR-V7, the TMPRSS2-ERG translocation was not enriched as a function of anti-androgen therapy and it was not correlated with acquired resistance.

Figure 10A:
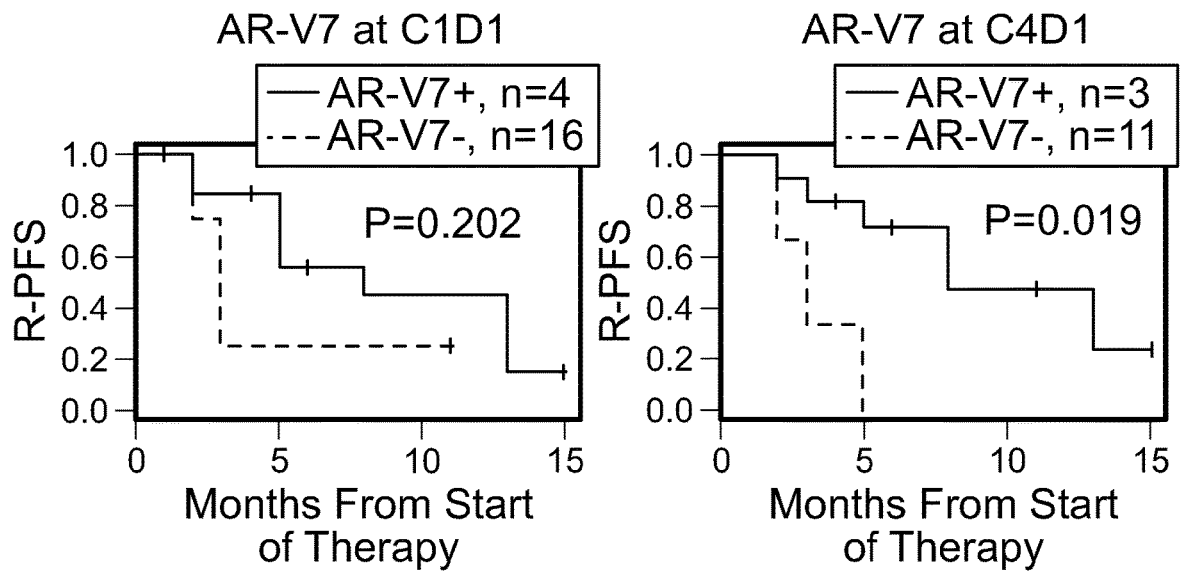
FIGS. 10A-10F are a series of Kaplan-Meier curves that show the results of a prospective evaluation of digital CTC markers.
Figure 10B:
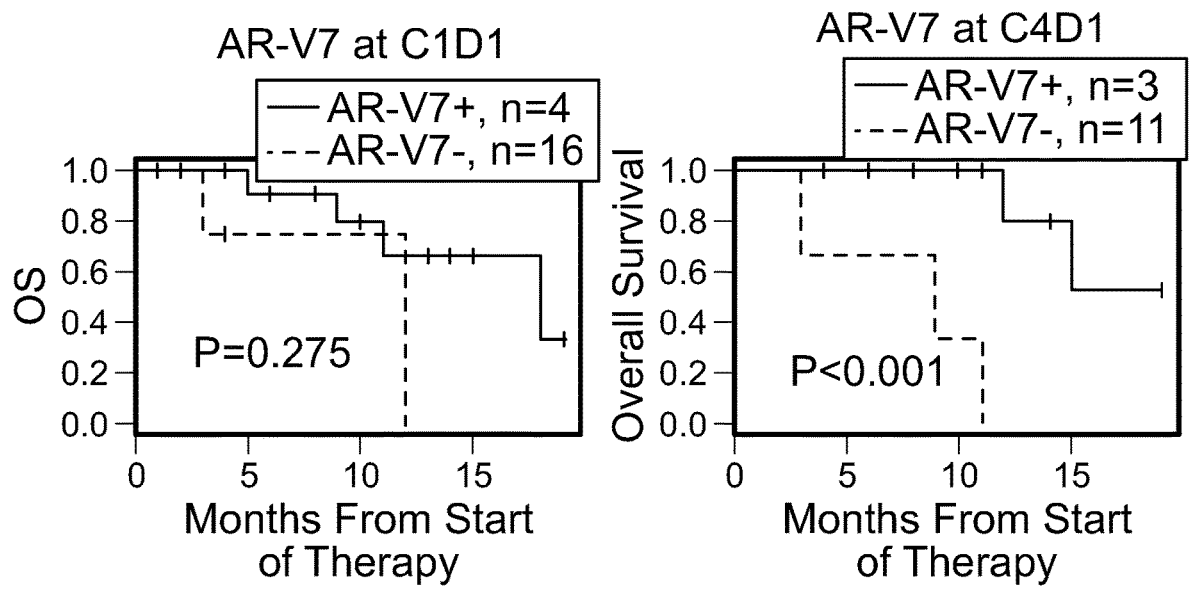
Figure 10C:
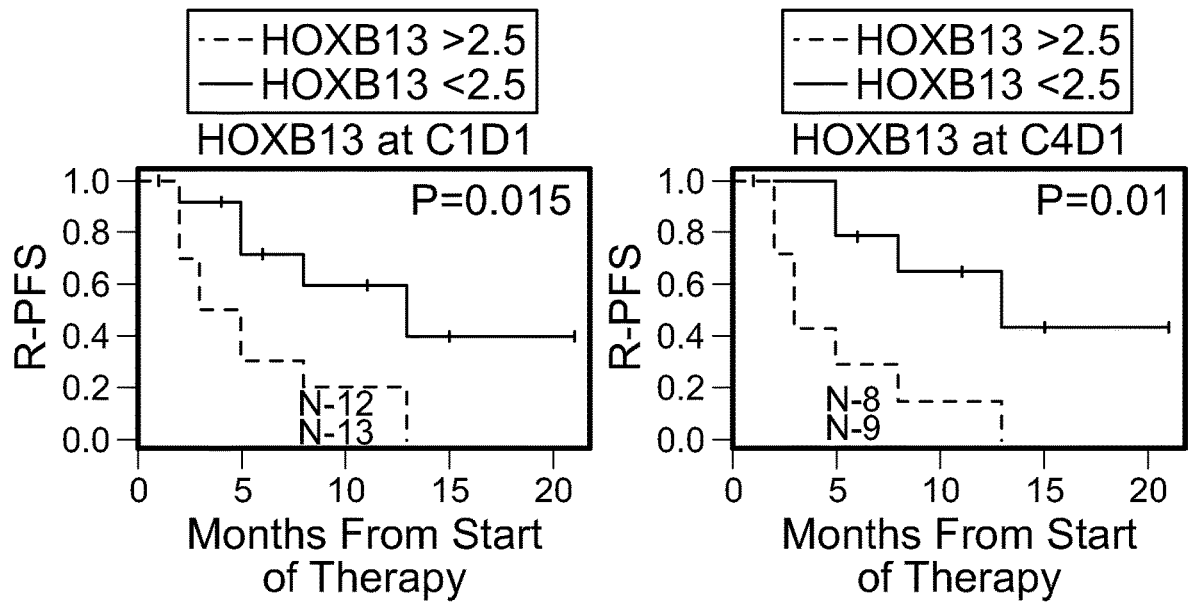
Figure 10D:
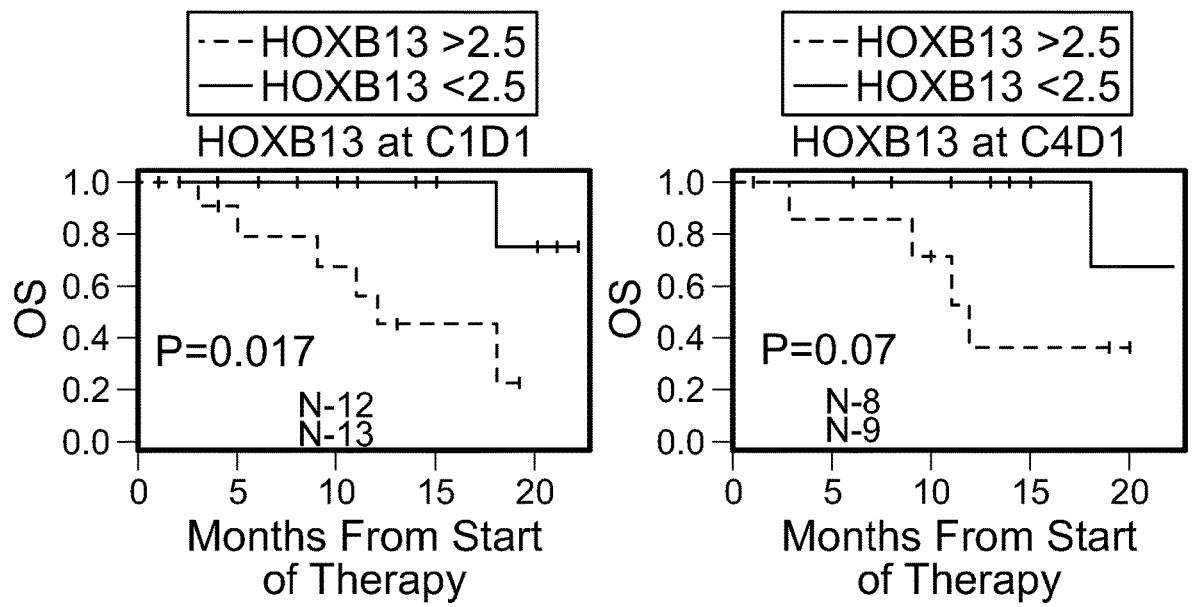
Figure 10E:
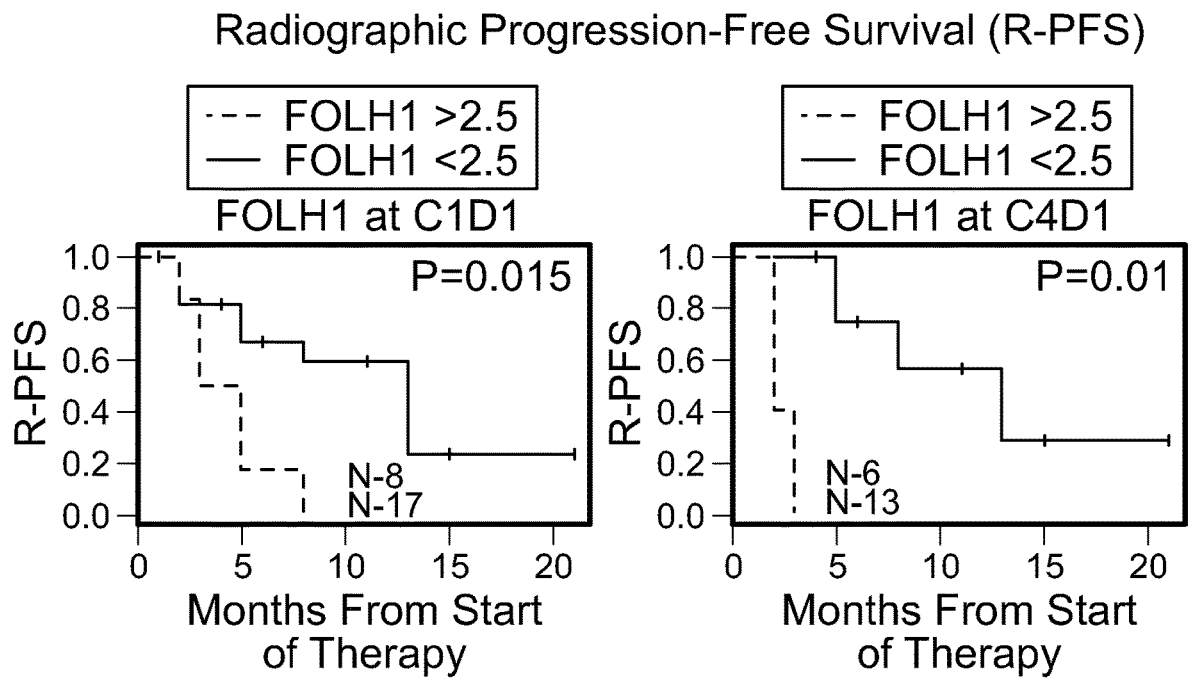
Figure 10F:
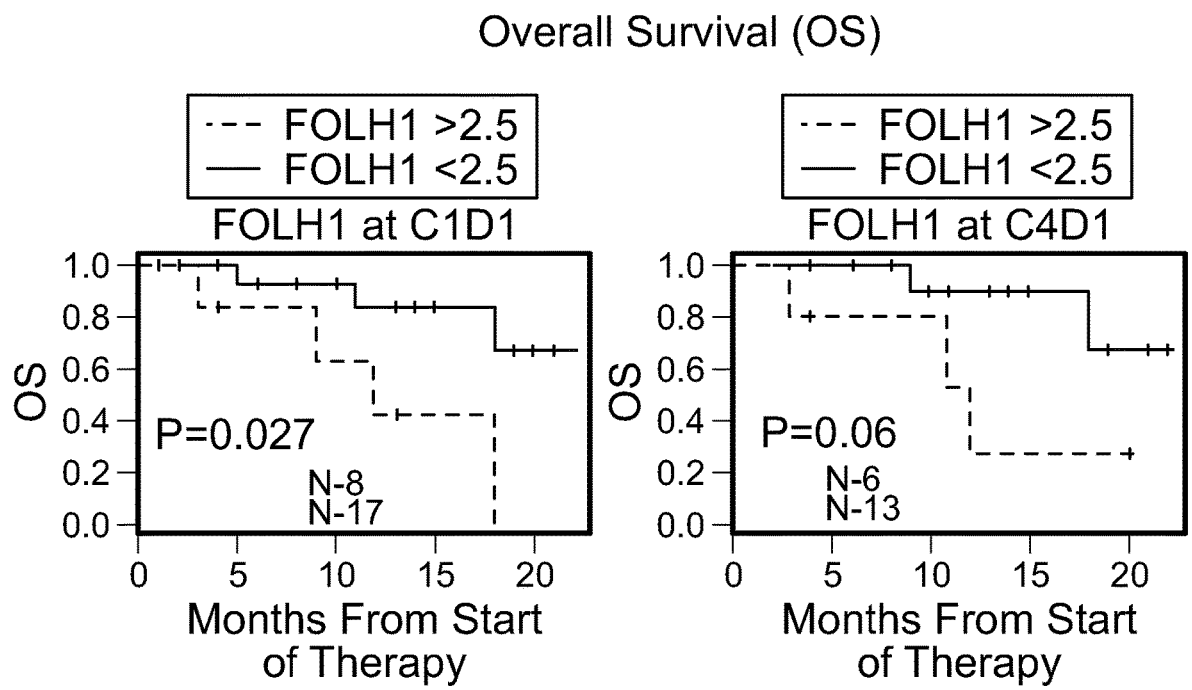

The AR-V7 splice variant measures one of several mechanisms linked to anti-androgen resistance, whereas expression of HOXB13 and FOLH1 are downstream indicators of aberrant androgen signaling. We therefore compared the predictive value of these orthogonal markers, either alone or in combination, in pretreatment CTCs drawn from patients in our prospective first line abiraterone cohort (FIG. 10). Positive signal for either HOXB13 or FOLH1 identified 8/11 (73%) of patients who went on to have early radiographic progression and 5/6 (83%) of those with a shortened overall survival (FIGS. 10C-F). At the same time point, AR-V7 positivity identified 3/11 (27%) of patients with radiographic progression and 2/6 (33%) with poor overall survival (FIGS. 10A-B). All AR-V7 positive patients also scored for HOXB13/FOLH1 expression, hence combining these two markers did not improve the predictive value of HOXB13/FOLH1 scoring alone. At the 3 months on-treatment time point (C4D1), the HOXB13/FOLH1 score identified 7/8 (88%) of patients with destined for radiographic progression and 5/5 (100%) of patients with shortened overall survival, compared with 3/8 (38%) and 3/5 (60%) for AR-V7 positivity. Taken all together, the analysis of CTC-derived digital signatures provides a novel and potentially powerful strategy for predictive assessment and disease monitoring in patients at first relapse of castration-resistant disease.

Example 6—Persistent Estrogen Receptor Signaling in CTCs Identifies Metastatic Breast Cancer Patients Who Will be Resistant to Hormonal Therapy In patients with hormone receptor-positive ("HR+") disease, persistent expression of a six-gene resistance signature ("RS") associated with estrogen signaling correlates with adverse outcomes, including shorter time to progression (TTP) and poor overall survival (OS) (p=0.02 (OS), p=0.003 (TTP)) when treated with drugs that target the estrogen-signaling pathway such as ER inhibitors (e.g., tamoxifen), selective ER degraders ("SERDs" such as fulvestrant), and aromatase inhibitors (AI), which block the production of estrogen (e.g., anastrozole, letrozole, and exemestane), e.g., in combination with CDK4/6 inhibitors.

Only half of the patients with a high RS score harbor ESR1 mutations, suggesting the involvement of additional mechanisms for drug-refractory estrogen signaling. Thus, digital RNA scoring of CTCs enables early monitoring of treatment response and provides the potential for a noninvasive measurement of drug effect on intracellular ER signaling pathways.

Patients

Patients were consented through an Institutional Review Board approved protocol for CTC collection (DFHCC 05-300). For the initial clinical benchmarking of the assay, 10-20 ml of peripheral blood (17 ml average) was collected from a total of 78 unique patients, representing 85 samples. These include pretreatment samples from 23 Stage I, 24 Stage II and 8 Stage III unique patients, and 30 on-treatment samples from 23 unique Stage IV patients. 33 samples from female healthy donors (HD) were obtained from the blood bank (9 ml average volume).

To determine if CTC monitoring through the breast CTC-ddPCR assay is predictive of treatment outcome and overall survival, we prospectively collected pretreatment and 3-4 weeks on-treatment draws from metastatic breast cancer patients initiating a new therapy (TRACK cohort). At least one sample was collected from 52 patients; 50% of the patients received some form of endocrine therapy, 10% received chemotherapy, 13% received anti-HER2 therapy while the rest were on a therapy that does not fall into any of these categories. To validate the assay detection characteristics established in the initial phase of assay development on the TRACK cohort, we also collected samples from 10 healthy women with negative breast biopsies after suspicious mammogram findings.

Microfluidic CTC Enrichment

The CTC-iChip technology for enrichment of CTC from whole blood, through the negative selection of RBC, WBC, and platelets, has been described above. In short, 8-20 ml of whole blood was incubated with biotinylated antibodies against the WBC markers CD45 (R&D Systems, clone 2D1), CD66b (AbD Serotec, clone 80H3), and CD16 (Janssen Diagnostics). Dynabeads MyOne Streptavidin T1 (Invitrogen) were then added to tag the WBC. The blood was subsequently fed through the CTC-iChip, where RBC and platelets were removed through size-based separation, while WBCs were depleted magnetically. The CTC-enriched product was centrifuged, preserved in RNA-later (Ambion) and flash-frozen for long-term storage.

Marker Selection and CTC Signal Scoring 17 markers for breast CTCs (AGR2, CXCL13, CXCL14, EFHD1, FAT1, FAT2, MGP, MUC16, PGR, PIP, PRAME, SCGB2A1, SERPINA3, SFRP1, SFRP2, TMPRSS4, WFDC2) were selected through literature search and mining in-house and publically available datasets including GTeX® and Oncomine® for markers expressed in breast cancer but not in whole blood. The specific genes and IDT probes used in the finalize breast cancer assay are listed in Table 6.

TABLE 6

| Primer name | Entrez Gene ID | IDT DNA Assay ID | ddPCR primer notes | ddPCR primer 1 | SEQ ID NO | ddPCR primer 2 | SEQ ID NO | ddPCR probe |
|---|---|---|---|---|---|---|---|---|
| AGR2 | 10551 | Hs.PT.58.3 8683802 | HEX "primary" probe | CTG ACA GTT AGA GCC GAT ATC AC | 378 | CAA TTC AGT CTT CAG CAA CTT GAG | 379 | /5HEX/ATG CTT ACG/ZEN/AAC CTG CAG ATA CAG CTC/3IABkFQ/ (SEQ ID NO: 355) |
| AGR2 | 10551 | HS.PT.58.20615543 | FAM, "secondary" probe | GTT TGT CCT CCT CAA TCT GGT | 380 | GTG ATA TCG GCT CTA ACT GTC AG | 381 | /56-FAM/TGA CAA ACA/ZEN/CCT TTC TCC TGA TGG CC/3IABkFQ/ (SEQ ID NO: 356) |
| CXCL13 | 10563 | Hs.PT.58.4 5801487 | FAM probe | TCA GCA GCC TCT CTC CA | 382 | GGG CAA GAT TTG AAT TCG ATC A | 383 | /56-FAM/TGT AGA TGT/ZEN/GTC CAA GAG AGC TCA GTC T/3IABkFQ/ (SEQ ID NO: 357) |
| CXCL14 | 9547 | Hs.PT.58.1 9273291 | FAM probe | GCT ACA GCG ACG TGA AGA AG | 384 | GAC CTC GGT ACC TGG ACA | 385 | /56-FAM/AAA TGA AGC/ZEN/CAA AGT ACC CGC ACT G/3IABkFQ/ (SEQ ID NO: 358) |
| EFHD1 | 80303 | Hs.PT..58.27534728 | FAM probe | TCG ATG TGG CCC TGG AG | 386 | TTC CGC TCA TCT TGC TCA G | 387 | /56-FAM/TCT TTG AAG/ZEN/CCA AGG TCC AAG CCT/3IABkFQ/ (SEQ ID NO: 359) |
| FAT1 | 2195 | Hs.PT.58.4 5775110 | HEX "primary" probe | ATC AGC AGA GTC AAT CAG TGA G | 388 | GAT CCT TAT GCC ATC ACC GT | 389 | /5HEX/TCT TGT CAG/ZEN/CAG CGT TCC CGG/3IABkFQ/ (SEQ ID NO: 360) |
| FAT1 | 2195 | HS.PT.58.14859907 | FAM, "secondary" probe | AGC TCC TTC CAG TCC GAA T | 390 | GTC TGC TCA TCA ATC ACC TCA | 391 | /56-FAM/ATC CCA GTG/ZEN/ATA CCC ATT GTC ATC GC/3IABkFQ/ (SEQ ID NO: 361) |
| FAT2 | 2196 | Hs.PT.58.2 4846942 | HEX "primary" probe | TCC TCC ACT CAT CTC CAA CT | 392 | CCT GGA TGC TGA CAT TTC TGA | 393 | /5HEX/ACC TGC TAC/ZEN/ATC ACA GAG GGA GAC C/3IABkFQ/ (SEQ ID NO: 362) |
| FAT2 | 2196 | HS.PT.58.3832648 | FAM, "secondary" probe | GGA CAG AGA GAA CAA GGA TGA AC | 394 | TGT GGG AGA ATA TAG GTG GAT TG | 395 | /56-FAM/TGG AGG TGA/ZEN/CTG TGC TGG ACA ATG/3IABkFQ/ (SEQ ID NO: 363) |
| MGP | 4256 | HS.PT.58.635768 | FAM probe | GGATTAAGTTCATA AGATTCCATGCT | 396 | CTTCGGCTTTGA TATCGTTTCAG | 397 | /56-FAM/CATGTGATT/ZEN/CCTG GGCACGATGC/3IABkFQ/ (SEQ ID NO: 364) |

TABLE 6-continued

| Primer name | Entrez Gene ID | IDT DNA Assay ID | ddPCR primer notes | ddPCR primer 1 | SEQ ID NO | ddPCR primer 2 | SEQ ID NO | ddPCR probe |
|---|---|---|---|---|---|---|---|---|
| MUC16 | 94025 | Hs.PT.58.3 543722 | FAM probe | GAC AAC AAC CAC CTT CAA TAC AC | 398 | AGA TCC AGG ACC GAT GGT T | 399 | /56-FAM/AGC CTC TTT/ZEN/ACT CCT CTG ACC ACA CC/3IABkFQ/ (SEQ ID NO: 365) |
| PGR | 5241 | Hs.PT.58.1 566542 | HEX "primary" probe | GGA CTG GAT AAA TGT ATT CAA GCA | 400 | GGC AAT TGG TTT GAG GCA A | 401 | /5HEX/ACA AGA TCA/ZEN/TGC AAG TTA TCA AGA AGT TTT GTA AGT T/3IABkFQ/ (SEQ ID NO: 366) |
| PGR | 5241 | Hs.Pt.58.5 0458902 | FAM, "secondary" probe | GGT GTT TGG TCT AGG ATG GAG | 402 | ACT GGG TTT GAC TTC GTA GC | 403 | /56-FAM/AGT GGG CAG/ZEN/ATG CTG TAT TTT GCA C/3IABkFQ/ (SEQ ID NO: 367) |
| PIP | 5304 | Hs.PT.58.1 9165954 | FAM, "secondary" probe | CAG TGC TTG CAG TTC AAA CAG | 404 | CCA GTA GAA GGT TTT TGG ATT GTC | 405 | /56-FAM/TGA GGT AAG/ZEN/TTT TAA CCA CCA TGC ATT CTT TC/3IABkFQ/ (SEQ ID NO: 368) |
| PIP | 5304 | Hs.PT.58.3 9868280 | HEX "primary" probe | TCA TTT GGA CGT ACT GAC TTG G | 406 | CTT GCT CCA GCT CCT GTT C | 407 | /5HEX/CCT GCT CCT/ZEN/GGT TCT CTG CCT G/3IABkFQ/ (SEQ ID NO: 369) |
| PRAME | 23532 | Hs.PT.58.4 5281469 | HEX "primary" probe | GCA ACA AGT GAC TGA GAC CTA | 408 | GTC CAC ACA CTC ATG CTG AT | 409 | /5HEX/CAA GCG TTG/ZEN/GAG GTC CTG AGG C/3IABkFQ/ (SEQ ID NO: 370) |
| SCGB2A1 | 4246 | Hs.PT.58.8 64035 | HEX "primary" probe | GTC TTT TCA ACC ATG TCC TCC A | 410 | ACT TCC TTG ATC CCT GCC A | 411 | /5HEX/CCA TGA AGC/ZEN/TGC TGA TGG TCC TCA /3IABkFQ/ (SEQ ID NO: 371) |
| SCGB2A1 | 4246 | HS.PT.58. 25526882 | FAM, "secondary" probe | ACT CTG AAA AAC TTT GGA CTG ATG | 412 | TCT AGC AAT CAA CAG ATG AGT TCT | 413 | /56-FAM/TAG CCC TCT/ZEN/GAG CCA AAC GCC/3IABkFQ/ (SEQ ID NO: 372) |
| SERPINA3 | 12 | Hs.PT.58.1 5580605 | FAM probe | CCT CAA ATA CAT CAA GCA CAG C | 414 | GGA AGC TTC ACC CAG CAA | 415 | /56-FAM/TAG CAG TCT/ZEN/CCC AGG TGG TCC A/3IABkFQ/ (SEQ ID NO: 373) |
| SFRP1 | 6422 | hs.pt.5803 8429156 | FAM probe | GAG ATG CTT AAG TGT GAC AAG TTC | 416 | CCT CAG ATT TCA ACT CGT TGT C | 417 | /56-FAM/TGG AGG CTT/ZEN/CGG TGG CAT TGG/3IABkFQ/ (SEQ ID NO: 374) |
| SFRP2 | 6423 | Hs.PT.58.2 0705989 | FAM probe | TTG CAG GCT TCA CAT ACC TT | 418 | GCC CGA CAT GCT TGA GT | 419 | /56-FAM/TTT CCC CCA/ZEN/GGA CAA CGA CCT TT/3IABkFQ/ (SEQ ID NO: 375) |
| TMPRSS4 | 56649 | Hs.PT.58.3 161735 | FAM probe | ATC TTC CCT CCA TTC TGC TTC | 420 | CAG TTC CCA CTC ACT TTC TCA G | 421 | /56-FAM/CTC ACT CCA/ZEN/GCC ACC CAC TC/3IABkFQ/ (SEQ ID NO: 376) |
| WFDC2 | 10406 | Hs.PT.58.2 5117187 | FAM probe | CCG ACA ACC TCA AGT GCT G | 422 | GCT GGG GAA AGT TAA TGT TCA C | 423 | /56-FAM/TGC TCT CTG/ZEN/CCC AAT GAT AAG GAG G/3IABkFQ/ (SEQ ID NO: 377) |

For the initial in vitro testing the panel, and to determine the linearity of the signal, we micro-manipulated increasing numbers of BRX-142 cells into 4 ml of HD blood and ran the samples through the CTC-iChip as described above. RNA was extracted using RNeasy® Micro Kit (Qiagen) and a quarter of it was then used for cDNA synthesis and amplification using the SMART-Seq v4 Ultra Low Input RNA Kit (Clontech). To establish the clinical specificity and sensitivity of the assay, CTC-iChip products from healthy donors and patients were similarly processed. ddPCR analysis was performed using predesigned Taqman-based qPCR assays (Invitrogen) and the ddPCR Supermix for Probes (No dUTP)(Biorad), on the Biorad ddPCR system. For markers detected with multiple probes, the average transcript number was used.

To normalize for differences in blood volumes among samples, all raw data were corrected for the blood-volume equivalent used in each ddPCR reaction. To further normalize the signal, the median and the doubled standard deviation of the expression of each marker within the 33 test healthy donors was established. The product of the two values was then subtracted from every patient and healthy donor sample analyzed in this study. The total CTC score was calculated by summing the normalized expression of all markers in a sample without additional weighing and reported as transcripts/ml of blood-volume equivalent used.

ESR1 Mutation Detection

Probes specific for the L536R, Y537C, Y537N, Y537S and D538G ESR1 mutations have been previously published. Their amplification efficiency, as well as that of their respective wild-type probes, was tested on synthetic sequences (data not shown). We established the ability of Y537S to detect mutations present in cDNA from CTC-enriched IFD product by micro-manipulating increasing number of BRx-68 cells in healthy donor blood, and then processing it as described above. 18-cycle WTA was performed using ⅓ of the extracted RNA with the SMART-Seq v4 Ultra Low Input RNA Kit (Clontech) following manufacturer protocols; 1 ul of undiluted WTA product was used per reaction. Patient samples were treated in identical manner; probe specificity was established at 100% after testing at least 5 healthy donor samples per probe. The cut-off for the presence of ESR1 mutation was established at >3 positive droplets.

Statistical Analysis

Receiver-operator curve analysis was performed to establish the specificity and sensitivity of each marker and the total CTC score for different cancer stages in our initial test cohort. The analysis was performed in R using the ROCR package. The specific script is available upon request. Wilcoxon tests were performed to establish significance of the AUC. The specificity and sensitivity in Stage IV cancer were validated using a new set of healthy donors and the pre-treatment samples from the TRACK cohort.

To determine the pre-treatment division point of high/low RS score, resampling using leave-one-out jack-knife was applied to the algorithm of Contal-O'Quigley to produce a division point that maximizes the difference in overall survival between the two resulting sub-groups. Comparisons of clinical variables between resulting groups are based on Fisher's exact tests for categorical characteristics and exact Wilcoxon rank-sum tests for continuous characteristics.

Survival analyses based on changes in CTC scores during treatment and on RS scores were analyzed using log-rank test, as subgroups within those comparisons had no events, preventing the use of cox model statistics. Unsupervised clustering of pretreatment and 3-4 week on-treatment samples was performed using Ward's minimum variance method.

Results

To develop an RNA expression signature to detect breast cancer cells within the background of contaminating normal blood cells, we first analyzed RNA-Seq and microarray gene expression data sets derived from normal breast tissue, breast cancer and whole blood as described above. We ultimately selected 17 markers whose expression is virtually absent in blood cells, but strongly expressed in breast-derived tissues. The markers include breast lineage-specific transcripts (PGR, SCGB2A1, PIP) and transcripts highly expressed in breast cancer (MGP, EFHD1), as well as genes implicated in endocrine signaling (SERPINA3, WFDC2), endocrine drug resistance (AGR2), cancer growth and metastasis (MUC16, TMPRSS4), cellular signaling (FAT1, FAT2, SFRP1, SFRP2), epithelial-derived cytokines (CXCL13, CXCL14), and oncofetal antigens (PRAME).

Single cell RNA sequencing revealed high, but variable, expression of the 17 markers in 15 individual CTCs isolated as single cells from the blood of women with breast cancer; 5 similarly analyzed single WBCs had negligible expression of these genes. Unlike traditional mutational signatures designed to distinguish between breast cancer and normal breast tissue, the CTC RNA signature panel was intended to inform on the tissue of origin of non-hematopoietic cells within a blood sample, with the potential to provide actionable clinical information for the diagnosis and monitoring of breast cancer.

Figure 11A:
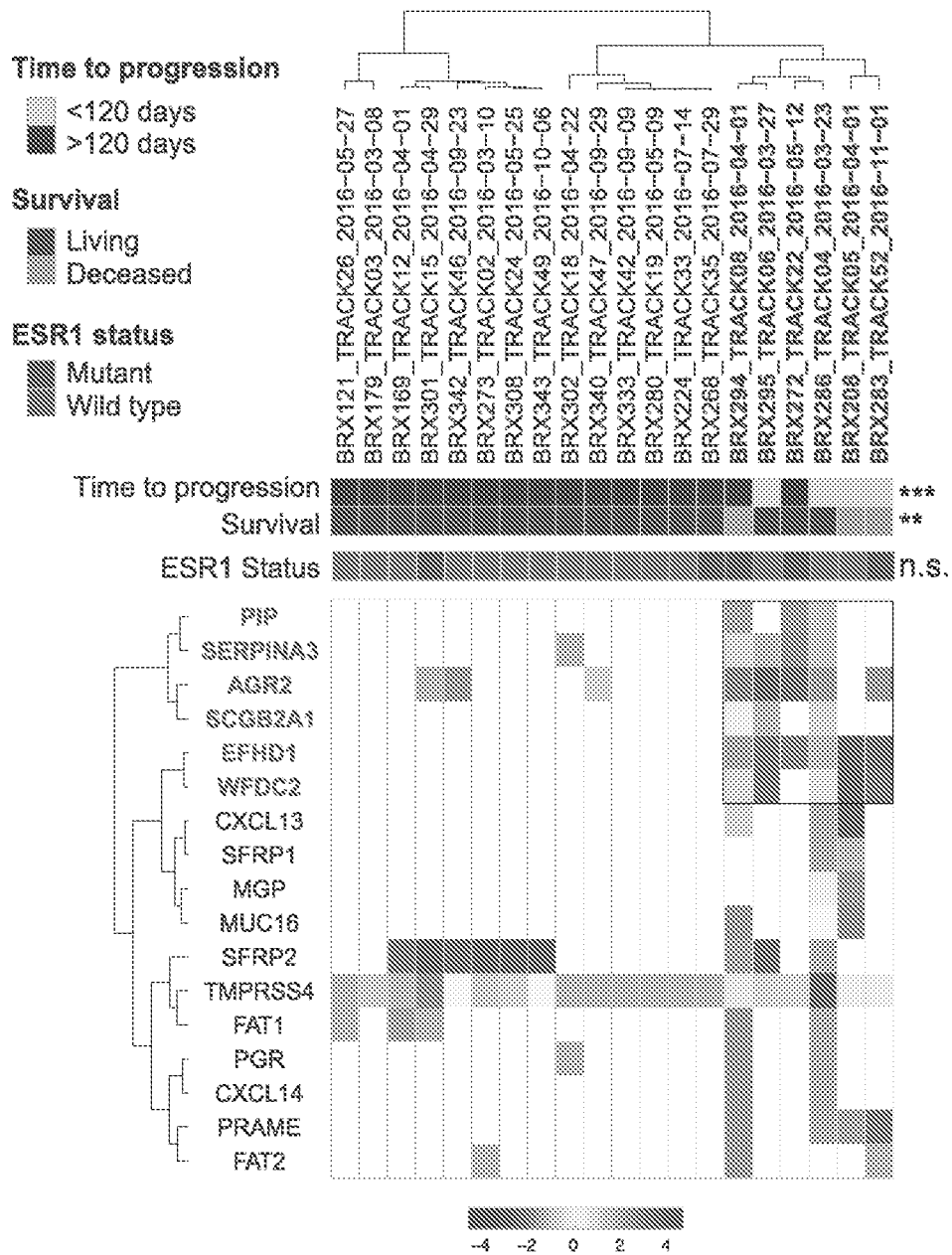
FIGS. 11A-D are a series of figures that show resistance signature (RS) markers that are associated with endocrine resistance ("ER") signaling identify high-risk HR+ patients receiving endocrine treatment and are prognostic of both OS and time to progression ("TTP") in this population.

To interrogate the entire panel of biomarkers for subsets that may be correlated with endocrine-refractory disease we performed unsupervised clustering of the breast assay components at 3-4 weeks after start of endocrine treatment in the subset of patients with HR+ disease, reasoning that treatment-induced expression changes may distinguish responding from non-responding patients. Indeed, we identified 6 genes (PIP, SERPINA3, AGR2, SCGB2A1, EFHD1 and WFDC2) within a Resistance Signature (RS), whose expression was associated with rapid disease progression (within 120 days) and poor survival ($p=0.0031$ and $p=0.0175$ respectively, Fisher's exact test) (FIG. 11A).

Figures 1, 11B:
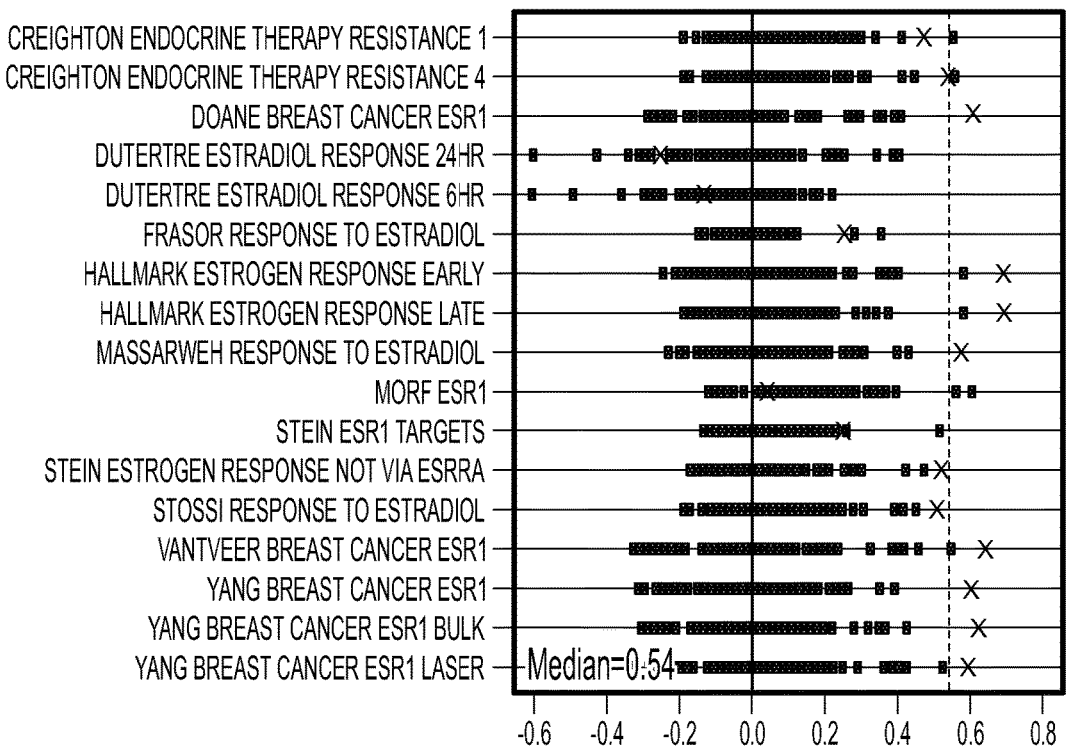
Figures 2, 11B:
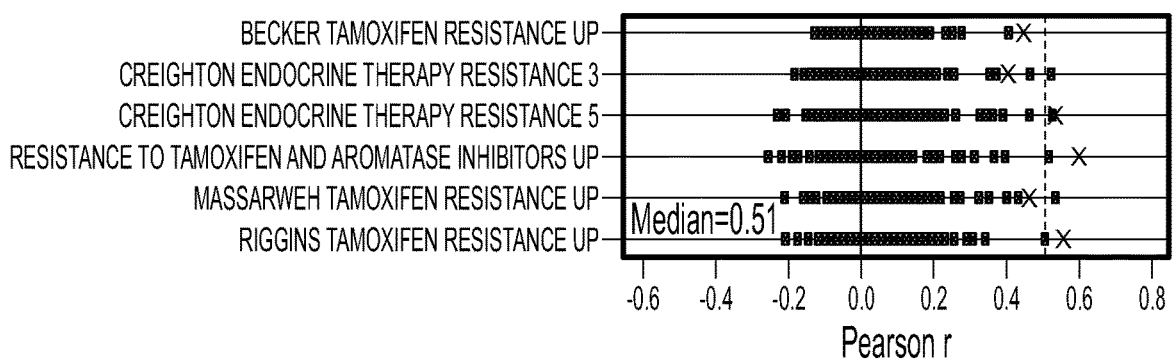

Remarkably, all 6 RS transcripts are significantly enriched in ER+ tumors compared to ER− tumors in the TCGA database, suggesting that their expression may be related to estrogen signaling. Indeed, a metascore based on the mean expression of the RS genes shows a highly significant correlation with the Hallmark Estrogen Receptor (Late) gene signature from the Molecular Signatures Database across multiple publically available gene expression datasets ($R=0.70$; $p=1.7e-70$). The RS gene metascore is also correlated with multiple other MSigDB sets related to estrogen signaling and endocrine resistance, resulting in median correlation coefficients of 0.54 and 0.51 respectively (FIGS. 11B-1 and 11B-2). Persistent enrichment of the RS transcripts in CTCs from women whose tumors are refractory to endocrine therapy suggests failure of these drugs to hit their target, as measured within circulating cancer cells.

Figures 1, 11C:
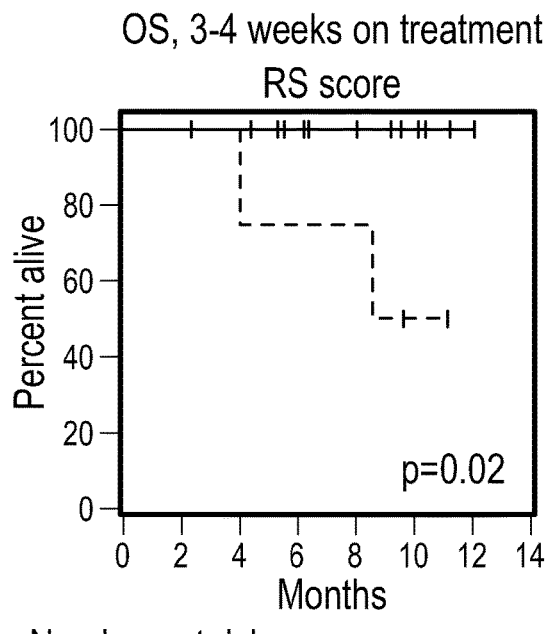
Figures 2, 11C:
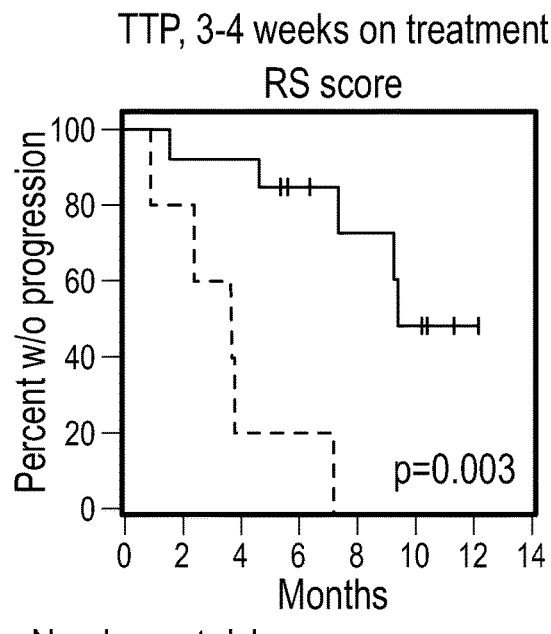
Figures 1, 11D:
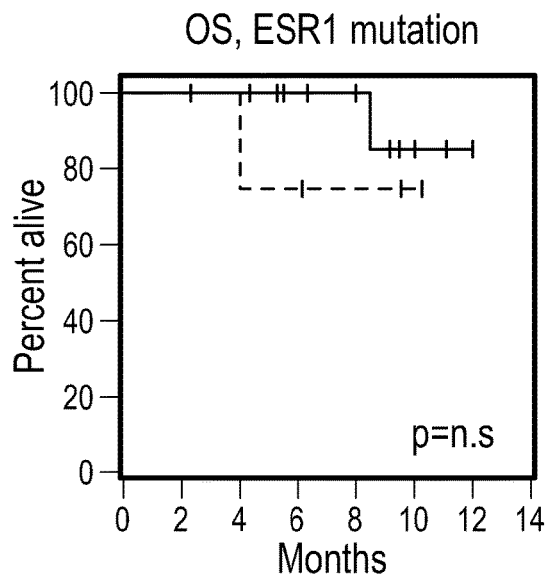
Figures 2, 11D:
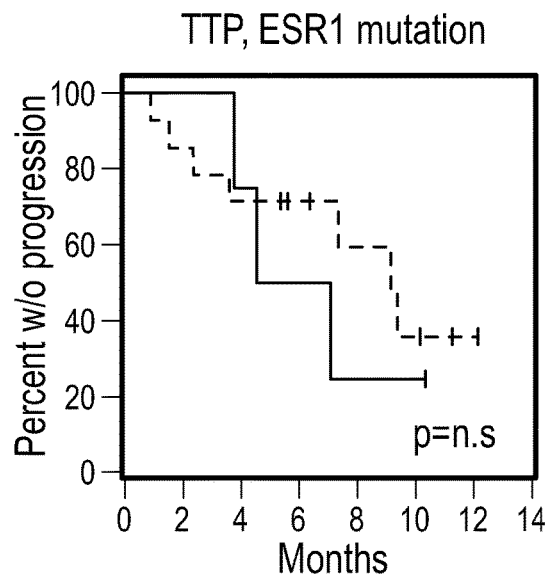

Activating mutations in the ESR1 gene encoding ER have been reported in breast cancers with acquired resistance to hormonal therapy and are thought to mediate persistent, ligand-independent ER signaling. In our 3-4 week HR+ patient cohort, 2/20 women had been diagnosed as having an ESR1 mutation based on tumor re-biopsy during the course of clinical care. See Table 7 below, which shows ESR1 mutations detected by CTC-ddPCR and SNapShot genotyping in HR+ patients on endocrine treatment and TNBC patients (negative control).

outcome (FIGS. 11D-1 and 11D-2). Expression of the RS expression signature at pretreatment baseline was not predictive of adverse outcome, suggesting that this signature

TABLE 7

| Sample | Date drawn | Mutation detected by CTC-ddPCR? | Specific ESR1 mutation detected by CTC-ddPCR | SNaPshot Date | SNaPshot Site | Mutation detected by SNaPshot? | Specific ESR1 mutation detected by SNaPshot |
|---|---|---|---|---|---|---|---|
| HR + patients receiving endocrine therapy | | | | | | | |
| BRX121_TRACK26 | 2016 May 27 | | | 2013 Aug. 26 | Primary | | |
| BRX169_TRACK12 | 2016 Apr. 1 | | | 2013 May 23 | Primary | | |
| BRX179_TRACK03 | 2016 Mar. 8 | | | 2014 Nov. 4 | Metastatic | | |
| BRX208_TRACK05 | 2016 Apr. 1 | | | 2015 Jun. 19 | Primary | | |
| BRX224_TRACK33 | 2016 Jul. 14 | | | 2015 Aug. 7 | Metastatic | | |
| BRX268_TRACK35 | 2016 Jul. 29 | X | D538G | 2015 Dec. 22 | Primary | | |
| BRX272_TRACK22 | 2016 May 12 | X | Y537N, D538G | 2016 Feb. 10 | Metastatic | | |
| BRX273_TRACK02 | 2016 Mar. 10 | NA | | 2013 Feb. 4 | Primary | NA | |
| BRX280_TRACK19 | 2016 May 9 | | | NA | NA | NA | |
| BRX283_TRACK52 | 2016 Nov. 1 | X | Y537C | 2016 Jan. 19 | Primary | | |
| BRX286_TRACK04 | 2016 Mar. 23 | | | 2016 Feb. 8 | Primary | NA | |
| BRX294_TRACK08 | 2016 Apr. 1 | X | L536R, Y537N | 2016 Feb. 5 | Metastatic | X | L536R, Y537N |
| BRX295_TRACK06 | 2016 Mar. 27 | | | NA | NA | NA | |
| BRX301_TRACK15 | 2016 Apr. 29 | | | 2014 Oct. 31 | Metastatic | X | L536Q* |
| BRX302_TRACK18 | 2016 Apr. 22 | | | NA | NA | NA | |
| BRX308_TRACK24 | 2016 May 25 | | | 2016 Mar. 6 | Primary | | |
| BRX333_TRACK42 | 2016 Sep. 9 | | | NA | NA | NA | |
| BRX340_TRACK47 | 2016 Sep. 29 | | | NA | NA | NA | |
| BRX342_TRACK46 | 2016 Sep. 23 | | | 2016 Aug. 26 | Metastatic | | |
| BRX343_TRACK49 | 2016 Oct. 6 | | | 2016 Aug. 15 | Metastatic | | |
| TNBC patients | !! | | !! | !! | !! | | !! |
| BRX167_TRACK01 | 2016 Feb. 9 | | | 2015 Sep. 24 | Metastatic | | |
| BRX213_TRACK07 | 2016 Mar. 3 | | | NA | NA | NA | |
| BRX279_TRACK20 | 2016 Apr. 14 | | | 2016 Jan. 8 | Primary | | |
| BRX281_TRACK25 | 2016 Apr. 22 | | | 2016 Mar. 6 | Metastatic | | |
| BRX287_TRACK09 | 2016 Mar. 8 | | | 2016 Jan. 28 | Metastatic | | |
| BRX289_TRACK17 | 2016 Mar. 31 | | | 2016 Feb. 9 | Metastatic | | |
| BRX319_TRACK32 | 2016 May 24 | | | 2016 Jul. 14 | Metastatic | | |
| BRX330_TRACK36 | 2016 Jul. 18 | | | 2015 Oct. 13 | Metastatic | NA | |
| BRX332_TRACK38 | 2016 Jul. 27 | | | 2016 Feb. 3 | Metastatic | NA | |
| BRX337_TRACK41 | 2016 Aug. 11 | | | 2016 Aug. 11 | Primary | | |
| BRX341_TRACK45 | 2016 Aug. 25 | | | 2016 May 20 | Metastatic | | |
| BRX345_TRACK50 | 2016 Sep. 16 | | | 2016 May 19 | Metastatic | | |

However many of the patients (8/20) had only undergone genotyping of their primary tumors, while others had had no genotyping performed (5/20). To noninvasively ascertain ESR1 mutation status in all patients, we established a specific digital PCR mutation assay using CTC-derived RNA template, with probes specific for L536R, Y537C, Y537N, Y537S and D538G, which together account for the majority of ESR1mutations (20, 22). The sensitivity and accuracy of the assay was confirmed by spiking single cells carrying the Y537S mutation into blood samples, followed by microfluidic CTC isolation and ddPCR performed on whole transcriptome-amplified cDNA from the product.

Using this CTC-based assay, additional 3 patients within our HR+ cohort were found to harbor ESR1 mutations, resulting in a total mutation frequency of 5/20 (25%), a prevalence that is consistent with previous studies of heavily treated metastatic HR+ breast cancer (20) (Table 7). Interestingly, the cases with ESR1 mutations were overlapping but not identical with those expressing the RS gene signature (FIG. 11A).

Of the 5 cases with an ESR1 mutation, 3 had the RS gene signature reflecting persistent ER signaling, and of 6 women with the RS signature, 3 had an ESR1 mutation. In our HR+ cohort, high RS score at 3-4 weeks after initiation of endocrine therapy, was highly prognostic of both poor survival and faster time to progression (FIGS. 11C-1 and 11C-2). In contrast, presence of an ESR1 mutation showed a trend but did not reach significance as predictive of adverse outcome (FIGS. 11D-1 and 11D-2). Expression of the RS expression signature at pretreatment baseline was not predictive of adverse outcome, suggesting that this signature only emerges as significant variable between responding and resistant patients following the administration of hormonal therapy that suppresses ER signaling within susceptible cancer cells.

The 17 genes that constitute the breast CTC signature were selected to include multiple tissue-derived and cancer-related transcripts with absent expression in blood cells that contaminate the enriched CTC product. As such, the 6 genes included in the RS sub-signature do not represent canonical ER targets, but their expression is, nonetheless, highly correlated with both ER signaling and resistance to endocrine therapy. Their persistent expression within CTCs after treatment initiation identifies women with greatly reduced response to hormonal therapy and shortened overall survival on treatment. The fact that this CTC signature emerges 3-4 weeks after start of hormonal therapy suggests that it may reflect drug-mediated effects on tumor cells. Initiation of novel ER-targeting therapy should suppress ER signaling in susceptible tumor cells, whereas persistent pathway activity would remain evident in cancer cells in which the drug fails to hit its intended target.

In addition, in this study, ESR1 mutations were noted at the expected frequency, but they were less predictive of adverse clinical outcome than persistent ER signaling as measured by the CTC expression signature.

Other Embodiments

It is to be understood that while the invention has been described in conjunction with the detailed description thereof, the foregoing description is intended to illustrate

What is claimed is:

1. A method for determining potential efficacy of an anti-cancer treatment regimen for hormone receptor-positive ("HR+") breast cancer in a subject and predicting if the subject will improve with the anti-cancer treatment regimen, the method comprising:
   isolating circulating tumor cells (CTCs) from a blood sample from the subject collected about three or more weeks after the start of treatment of the subject with the anti-cancer treatment regimen, wherein the anti-cancer treatment regimen comprises a drug targeting an estrogen-signaling pathway;
   converting CTC-derived RNA into cDNA;
   encapsulating the cDNA into individual droplets;
   amplifying the cDNA in each droplet using probes and primers specific for cDNA molecules within each of the droplets that correspond to three or more of PIP, SERPINA3, AGR2, SCGB2A1, EFHD1, and WFDC2 genes in the presence of a reporter group configured to bind specifically to cDNA molecules that correspond to three or more of PIP, SERPINA3, AGR2, SCGB2A1, EFHD1, and WFDC2 genes from CTCs and not to cDNA from other cells in the blood; and
   determining a presence and expression level of three or more of PIP, SERPINA3, AGR2, SCGB2A1, EFHD1, and WFDC2 genes in the CTCs in the blood sample, wherein an expression level of the three or more genes is predictive of progression-free survival and overall survival of the subject for the anti-cancer treatment regimen; and
   wherein if the expression levels of three or more of PIP, SERPINA3, AGR2, SCGB2A1, EFHD1, and WFDC2 genes at about three or more weeks after the start of treatment with a drug targeting an estrogen-signaling pathway are elevated above a background noise level determined by evaluation of healthy donors without cancer, then the method predicts that the subject will not improve if treated only with a drug that targets the estrogen-signaling pathway.

2. The method of claim 1, wherein the potential efficacy of a specific anti-cancer treatment regimen in the subject is determined by comparing the expression levels of three or more of PIP, SERPINA3, AGR2, SCGB2A1, EFHD1, and WFDC2 genes to a reference standard established for the specific anti-cancer treatment regimen to determine whether the subject will improve with the specific anti-cancer treatment regimen.

3. The method of claim 1, wherein the drug comprises an ER inhibitor, a selective ER degrader and an aromatase inhibitor which block the production of estrogen.

4. The method of claim 1, wherein the subject is further prescribed a combination therapy of a drug targeting the estrogen-signaling pathway and another anti-breast cancer therapy.

5. The method of claim 1, further comprising isolating from the blood sample a product including CTCs and other cells present in blood, and reducing a volume of the product before isolating RNA.

6. The method of claim 1, further comprising removing contaminants from the cDNA-containing solution before encapsulating the cDNA molecules.

7. The method of claim 1, wherein generating cDNA molecules from the CTC-derived RNA comprises conducting reverse transcription (RT) polymerase chain reaction (PCR) of the CTC-derived RNA molecules.

8. The method of claim 1, wherein amplifying cDNA or cDNA molecules within each of the droplets comprises conducting PCR in each droplet.

9. The method of claim 1, wherein encapsulating the cDNA further comprises encapsulating PCR reagents in individual droplets with the cDNA and forming at least 1000 droplets of a non-aqueous liquid.

10. The method of claim 1, wherein the reporter groups comprise a fluorescent label.

11. The method of claim 1, wherein probes and primers for use in amplifying the cDNA within each of the droplets are selected from probes and primers listed below:

PIP primers of SEQ ID NOs: 163 and 164, and PIP probe comprising a sequence of SEQ ID NO: 165;

SERPINA3 primers of SEQ ID NOs: 190 and 191, and SERPINA3 probe comprising a sequence of SEQ ID NO: 192;

AGR2 primers of SEQ ID NOs: 1 and 2, and AGR2 probe comprising a sequence of SEQ ID NO: 3;

SCGB2A1 primers of SEQ ID NOs: 82 and 83, and SCGB2A1 probe comprising a sequence of SEQ ID NO: 84;

EFHD1 primers of SEQ ID NOs: 386 and 387, and EFHD1 probe comprising a sequence of SEQ ID NO: 359; and WFDC2 primers of SEQ ID NOs: 422 and 423, and WFDC2 probe comprising a sequence of SEQ ID NO: 377.

12. The method of claim 1, wherein the CTCs arise from metastatic or primary/localized cancers.

13. The method of claim 3, wherein the drug comprises one or more of an ER inhibitor comprising tamoxifen, a selective ER degrader comprising fulvestrant, and an aromatase inhibitor comprising one or more of anastrozole, letrozole, and exemestane.

14. The method of claim 4, further comprising administering to the subject the combination therapy of a drug targeting the estrogen-signaling pathway and another anti-breast cancer therapy.

15. The method of claim 14, wherein the combination therapy is selected from the group consisting of endocrine therapies and CDK 4/6 inhibitors; endocrine therapies and PI3K inhibitors; endocrine therapies and mTOR inhibitors; chemotherapy and PARP inhibitors; and chemotherapy and HER2 inhibitors.

* * * * *

SEQUENCE LISTING

<160> NUMBER OF SEQ ID NOS: 423

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctgacagtta gagccgatat cac                                              23

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caattcagtc ttcagcaact tgag                                             24

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
aacctgcaga tacagctc                                                    18

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggtggcttta aaatgtcagg aa                                               22

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgtcgccaag tttgatggt                                                   19

<210> SEQ ID NO 6
<211> LENGTH: 19
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 6
ctgtgtattc ggccaaagc                                                    19

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctctgcattt ttggacatag gag                                               23

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gccttgcact tccattatga c                                                 21

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
gtactgtcat tcacct                                                       16

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaggcctaca ttctgaacgc                                                   20

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtggttcttt cttttgcctt ctc                                               23

<210> SEQ ID NO 12
<211> LENGTH: 15
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 12
ctgcatcgtc attct                                                      15

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtttcatcct ccctgtgctg                                                 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gctccttgat cttccgcttc                                                 20

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
ctgcttttgt tggt                                                       14

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gatgccccac ttgcagta                                                   18

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cctcgtaaac tggctaatgg t                                               21

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 18
acctacccca atatatgaag gaaa                                          24

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctgctgccac aaccagt                                                  17

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttcacatcca tctggtacgt g                                             21

<210> SEQ ID NO 21
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
ctgccgcaaa ttc                                                      13

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gatccttatg ccatcaccgt                                               20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atcagcagag tcaatcagtg ag                                            22

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
cagcgttccc gg                                                          12

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cctggatgct gacatttctg a                                                21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tcctccactc atctccaact                                                  20

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
atcacagagg gagacc                                                      16

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
caatgtgata ggtactctca gagg                                             24

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgttccaaag ctcctcacaa                                                  20

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence: Synthetic
      probe -continued

```
<400> SEQUENCE: 30
agctgctcca ctctga                                                     16

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cagccagatg tgttgcca                                                   18

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctgtacggaa tgcgtttctt g                                               21

<210> SEQ ID NO 33
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
cagactccag cgg                                                        13

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gctgtgtaca gtcatggatg g                                               21

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gtcttcaggc tcaaacaggt                                                 20

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
```

```
ttctttaggc aatgggca                                              18

<210> SEQ ID NO 37
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gtgtgctgga cgctgga                                               17

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtgatacctt gaagcacacc attac                                      25

<210> SEQ ID NO 39
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
gctcgggtga ttct                                                  14

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cacatttgag tgaagcttgt cg                                         22

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gcggatgtca aacaagtcaa g                                          21

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
```
aatgaagcca ccaca                                                    15

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gaaggagaag atctgccagt g                                             21

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gctgactcct ctgctcaag                                                19

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
ccagagtcat catgc                                                    15

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccagtagcct gattgtgcat                                               20

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgtcagtgat tctgttcaag ga                                            22

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
aagagggcat tttggttgt                                                19

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
actcttacac cacggctga                                                19

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ccatcaaggc tctgtatcca t                                             21

<210> SEQ ID NO 51
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
aggatcactg tcagga                                                   16

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggatctgagc aggagaaata cc                                            22

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gaattcttca ttcccttgaa ctga                                          24

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
gaaaaagaca aattccaaag                                               20

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aagatggaca ggtatgacaa gtc                                          23

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
actctttcca catagtcaga tgg                                          23

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
atttttaacc cactcctcg                                               19

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tgtcctggct gttcattctg                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tggatcccta tctcttgcca                                              20

<210> SEQ ID NO 60
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 60
ctgtccatct cct                                                     13

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
ggcaattggt ttgaggcaa                                    19

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
ggactggata aatgtattca agca                              24

<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence: Synthetic probe

<400> SEQUENCE: 63
tgcaagttat caagaagttt tgtaagtt                          28

<210> SEQ ID NO 64
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
ctggtggagg agaacgg                                      17

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
ggtcgctgga tgaaaggtt                                    19

<210> SEQ ID NO 66
<211> LENGTH: 11
<212> TYPE: DNA
<213> ORGANISM: Artificial Sequence
<220> FEATURE:
<223> OTHER INFORMATION: Description of Artificial Sequence: Synthetic probe

<400> SEQUENCE: 66
agcagctcga a                                            11

<210> SEQ ID NO 67

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
caggcatcgt cagtttcct                                                19

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
acacaatgga tctggtgcta a                                             21

<210> SEQ ID NO 69
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 69
gataggtgct ttgctg                                                   16

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gaggagagaa tcaacaaact gc                                            22

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
aggttcaggt actccttcca g                                             21

<210> SEQ ID NO 72
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 72
attgaggcgc acat                                                     14

<210> SEQ ID NO 73
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
atacttctgc ttggtgtagg c                                              21

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
agccattgta ctctttaacc ca                                             22

<210> SEQ ID NO 75
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75
ggagactctg cgaga                                                     15

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ccgagaatta cgttcctaca gtg                                            23

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gcggacattg tcatagtaag ga                                             22

<210> SEQ ID NO 78
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 78
tttgaaatcg acacac                                                    16

<210> SEQ ID NO 79
<211> LENGTH: 18
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 79
ctgccttgct ctccttcc                                                    18

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cttactcagc ttgaacttgt cg                                               22

<210> SEQ ID NO 81
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 81
gccacagatc catg                                                        14

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
acttccttga tccctgcca                                                   19

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gtcttttcaa ccatgtcctc ca                                               22

<210> SEQ ID NO 84
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
tgctgatggt cctca                                                       15

<210> SEQ ID NO 85
<211> LENGTH: 17
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 85
caatgccacc gaagcct                                                    17

<210> SEQ ID NO 86
<211> LENGTH: 26
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 86
cttttatttt catcctcagt gcaaac                                          26

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 87
gagttgaaat ctgaggcc                                                   18

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 88
cttgtcactt tcgttcagca g                                               21

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 89
cttcatggtg tgggctca                                                   18

<210> SEQ ID NO 90
<211> LENGTH: 12
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 90
tgcgggtact gg                                                         12

<210> SEQ ID NO 91
<211> LENGTH: 21
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 91
tccttggatg actctcccta c                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
agataccacc tccctgaaga a                                              21

<210> SEQ ID NO 93
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 93
aggagcggga tggag                                                     15

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
agaggtttaa tgggctcaca g                                              21

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ctctggtctg tcgtcatgta ag                                             22

<210> SEQ ID NO 96
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 96
tcaccttctc cacca                                                     15

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 97
cacaccacca tacctggata at                                              22

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
tcacttgagg ccaagagttc                                                 20

<210> SEQ ID NO 99
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99
ggtccagcca agttc                                                      15

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ctttcttcag ggtctggtca tt                                              22

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
cttgtcgtct tcggaaatgt tatg                                            24

<210> SEQ ID NO 102
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
tgactctggg agaaa                                                      15

<210> SEQ ID NO 103
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gaggcaagtc agcctttct                                              19

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
tgtccatctt gtcgtcttcg                                             20

<210> SEQ ID NO 105
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
gatgactctg ggaga                                                  15

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
gctcaccatg tgtgacttga                                             20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
tgggagagag acagcttgta                                             20

<210> SEQ ID NO 108
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
gagagctgca tcagt                                                  15

<210> SEQ ID NO 109
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gaaagtccac gctcaccat                                                  19

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gcagccttgc tctctagc                                                   18

<210> SEQ ID NO 111
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111
gagagctgca tcagt                                                      15

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
ctctgcacaa actcttccat ttc                                             23

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
tttcctcgcc cattcttacc                                                 20

<210> SEQ ID NO 114
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 114
ttacagtgaa gtcctcc                                                    17

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ggaaggaggg aacagaaatc c                                              21

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gtgagctact ggctgaacta tt                                             22

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 117
atttgagaag aatggtgga                                                 19

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
aggagatgtg ctggattgtc                                                20

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
tctgcatgaa ttatacattg accac                                          25

<210> SEQ ID NO 120
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 120
aactgaccac gctg                                                      14

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
actgcagaga taagtttagc tgac                                          24

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
tcaccatttt gcttacttcc ttg                                           23

<210> SEQ ID NO 123
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 123
ttgttcaaga agccac                                                   16

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
catgttgcct acagcctct                                                19

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
tctccaaact tcttcctcat tcc                                           23

<210> SEQ ID NO 126
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 126
atcagcaggt tcatgca                                                  17

<210> SEQ ID NO 127
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gaagatcatc ctgtcagacg ag                                            22

```
<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
cttccgagct agaacctgta tg                                                22

<210> SEQ ID NO 129
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 129
tcaactcatt tcggc                                                        15

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
gatcagacag tcattcgcaa ag                                                22

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gacaatcttc cagggactga g                                                 21

<210> SEQ ID NO 132
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 132
gttcagaggg ttctt                                                        15

<210> SEQ ID NO 133
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
cccaacccag gcatgatg                                                     18
```

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
tcaatgagaa gcaccttggc                                              20

<210> SEQ ID NO 135
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 135
tccagcagag ct                                                      12

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
tgctggaatg gacaagaact c                                            21

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gctcatggag attgaactgg t                                            21

<210> SEQ ID NO 138
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 138 cctttggct gtatct                                                   16

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
cttactggcg ttttctcatg c                                            21

```
<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
ccaactcttg tagaggtctc aag                                              23

<210> SEQ ID NO 141
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 141
gcccactttt cctaggt                                                     17

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
ggaccaggga aagataaagc c                                                21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gcaaggtaga ttcgtgacag a                                                21

<210> SEQ ID NO 144
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 144
aatcccaacc acaaa                                                       15

<210> SEQ ID NO 145
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
cattttgtgg ttgggattct gg                                               22

<210> SEQ ID NO 146
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gatgctgtgg atgtggct                                                 18

<210> SEQ ID NO 147
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 147
atctaccttg ctgctca                                                  17

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
gccttgcact tccattatga c                                             21

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
ctctgcattt ttggacatag gag                                           23

<210> SEQ ID NO 150
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 150
gaggtcctga ggc                                                      13

<210> SEQ ID NO 151
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
atgtggagtt tacagtgtct gg                                            22

<210> SEQ ID NO 152
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
agcttctcac tgagtgttgc                                                 20

<210> SEQ ID NO 153
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 153
cagccaagtg taacc                                                      15

<210> SEQ ID NO 154
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
acggctccca tcctcct                                                    17

<210> SEQ ID NO 155
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
ccactatgtc accatgtacc tg                                              22

<210> SEQ ID NO 156
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 156
agaaccagca gc                                                         12

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
tgctctgaca acccttatgc                                                 20

<210> SEQ ID NO 158
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 158
ggctgaggat cactttgtag a                                              21

<210> SEQ ID NO 159
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 159
gtctttgctg acatt                                                     15

<210> SEQ ID NO 160
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
catcagcagg accagtagc                                                 19

<210> SEQ ID NO 161
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
tgtctgtgct ccctgatct                                                 19

<210> SEQ ID NO 162
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 162
agtaccagga ctgct                                                     15

<210> SEQ ID NO 163
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tcatttggac gtactgactt gg                                             22

<210> SEQ ID NO 164
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 164
cttgctccag ctcctgttc                                                  19

<210> SEQ ID NO 165
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 165
ggttctctgc ctg                                                        13

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
ggtgtttggt ctaggatgga g                                               21

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
actgggtttg acttcgtagc                                                 20

<210> SEQ ID NO 168
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 168
atgctgtatt ttgcac                                                     16

<210> SEQ ID NO 169
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
gtgactctcc tgacatcctt ag                                              22

<210> SEQ ID NO 170
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 170
ccatctcatt tcgtcctcca a                                            21

<210> SEQ ID NO 171
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 171
acagacatag gcaaagt                                                 17

<210> SEQ ID NO 172
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
actctgaaaa actttggact gatg                                         24

<210> SEQ ID NO 173
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
tctagcaatc aacagatgag ttct                                         24

<210> SEQ ID NO 174
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 174
gagccaaacg cc                                                      12

<210> SEQ ID NO 175
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
agctccttcc agtccgaat                                               19

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 176
gtctgctcat caatcacctc a                                              21

<210> SEQ ID NO 177
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 177
atacccattg tcatcgc                                                   17

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
ggacagagag aacaaggatg aac                                            23

<210> SEQ ID NO 179
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
tgtgggagaa tataggtgga ttg                                            23

<210> SEQ ID NO 180
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 180
ctgtgctgga caatg                                                     15

<210> SEQ ID NO 181
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
gctttgacat cagtagacca gag                                            23

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 182
ctgtccgcag atcagacttg                                              20

<210> SEQ ID NO 183
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 183
tcaaaaagtg gaaaggtga                                               19

<210> SEQ ID NO 184
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
cctggaaaat ggcctcctt                                               19

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
cattgcctac aggaagtctg g                                            21

<210> SEQ ID NO 186
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 186
tatgccaaga gtgtgag                                                 17

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
ccagaggtaa aggtgccaac                                              20

<210> SEQ ID NO 188
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 188
tcccagataa ctgtcatgaa gc                                        22

<210> SEQ ID NO 189
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 189
gcagagtaac tacaaaggc                                            19

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
cctcaaatac atcaagcaca gc                                        22

<210> SEQ ID NO 191
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
ggaagccttc accagcaa                                             18

<210> SEQ ID NO 192
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 192
cccaggtggt cca                                                  13

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
ttgcaggctt cacatacctt                                           20

<210> SEQ ID NO 194
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
gcccgacatg cttgagt					17

<210> SEQ ID NO 195
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 195
ggacaacgac cttt					14

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
ctcttgcagc cattcctctt					20

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
cccttacccc agtcacttct					20

<210> SEQ ID NO 198
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 198
cctcttctct cctcccct					18

<210> SEQ ID NO 199
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
tggacagaag acatactcat aaagg					25

<210> SEQ ID NO 200
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
ggtgccagca tgaatccc                                              18

<210> SEQ ID NO 201
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 201
tggacctgca gttatca                                               17

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
atcttccctc cattctgctt c                                          21

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
cagttcccac tcactttctc ag                                         22

<210> SEQ ID NO 204
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 204
gccaccccac tc                                                    12

<210> SEQ ID NO 205
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
ttttgcacca gtctcgctt                                             19

<210> SEQ ID NO 206
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
gccgcactga cagtatgag                                             19

<210> SEQ ID NO 207
<211> LENGTH: 11
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 207
tgggagccct g                                                        11

<210> SEQ ID NO 208
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
cgactgcgag tgataccg                                                 18

<210> SEQ ID NO 209
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
ctctccacgc actccct                                                  17

<210> SEQ ID NO 210
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 210
aacagccaca acg                                                      13

<210> SEQ ID NO 211
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
tgccgctcat gttcatgc                                                 18

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
caggacacca tgaggaacag                                               20

<210> SEQ ID NO 213
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 213
tcccgcttca                                                              10

<210> SEQ ID NO 214
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
aagatgtcag acactgagaa cg                                                22

<210> SEQ ID NO 215
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
cgaagcccga tgtggtc                                                      17

<210> SEQ ID NO 216
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 216
agtccaaagc acacga                                                       16

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
aggagatgtg ctggattgtc                                                   20

<210> SEQ ID NO 218
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
tctgcatgaa ttatacattg accac                                             25

```
<210> SEQ ID NO 219
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 219
aactgaccac gctg                                                       14

<210> SEQ ID NO 220
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
atgtggagtt tacagtgtct gg                                              22

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
agcttctcac tgagtgttgc                                                 20

<210> SEQ ID NO 222
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 222
cagccaagtg taacc                                                      15

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
gagatctgct tgaatgtgct g                                               21

<210> SEQ ID NO 224
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
caacagaggt ttttcacagc at                                              22

<210> SEQ ID NO 225
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 225
tggcaaggtc cgccc                                                  15

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
catggtaggc tgagatgctt t                                           21

<210> SEQ ID NO 227
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
gacgataagg agacctgctt tg                                          22

<210> SEQ ID NO 228
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 228
tgcaagtcaa gctgc                                                  15

<210> SEQ ID NO 229
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
gcgcattctg gaatttgtac tc                                          22

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
gctatgccaa agtgttcgat g                                           21

<210> SEQ ID NO 231
<211> LENGTH: 15
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 231
ggaagagcct cagaa                                                     15

<210> SEQ ID NO 232
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
tgatggatat tctctggatg gc                                             22

<210> SEQ ID NO 233
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
cctgaatctt tactctctct ccttg                                          25

<210> SEQ ID NO 234
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 234
cagtttggta cattctattt cttcc                                          25

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
gcacttcaag ttcaccatca c                                              21

<210> SEQ ID NO 236
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
accagtttat tgtcaccttc ca                                             22

<210> SEQ ID NO 237
<211> LENGTH: 17
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 237
cttgactttc tcccctg                                                    17

<210> SEQ ID NO 238
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
acatctatta ttgctactat tgtgtgtt                                        28

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
tgggagcctc ttctctcttc                                                 20

<210> SEQ ID NO 240
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 240
attgtcgttg acacc                                                      15

<210> SEQ ID NO 241
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
ttcatttgat aagcacacag tctg                                            24

<210> SEQ ID NO 242
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
accttgaaca tggcatagtc tg                                              22

<210> SEQ ID NO 243
<211> LENGTH: 16
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 243
agtcttccag ttccac                                                    16

<210> SEQ ID NO 244
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
aatcagctcc gcttccttg                                                 19

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
tgcttatctc gttgtccttc g                                              21

<210> SEQ ID NO 246
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 246
catcatccac atcc                                                      14

<210> SEQ ID NO 247
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
cagaagcgca gaagattgta ag                                             22

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
tctttctgat ctgccatcgc                                                20

<210> SEQ ID NO 249
<211> LENGTH: 13
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 249
gtccacaacg gtt                                                         13

<210> SEQ ID NO 250
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
agaagcgagt ccgactgt                                                    18

<210> SEQ ID NO 251
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
cactgcacac catctcaca                                                   19

<210> SEQ ID NO 252
<211> LENGTH: 11
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 252
gccccaggac g                                                           11

<210> SEQ ID NO 253
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
cagatggagg aggaagattc tg                                               22

<210> SEQ ID NO 254
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
gtatactgcc tggagttctc tg                                               22

<210> SEQ ID NO 255
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 255
ctggttcagg tctccattac ag                                              22

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
gctgtgactc tgagcaagta                                                 20

<210> SEQ ID NO 257
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
tgtcctcctc aatctggttt atg                                             23

<210> SEQ ID NO 258
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
gacagaaggg cttggagatt t                                               21

<210> SEQ ID NO 259
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
cggtggcgtt gtagaagat                                                  19

<210> SEQ ID NO 260
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
agaagatctc tgcctccga                                                  19

<210> SEQ ID NO 261
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
caagatagtt gtggtgggag ac                                            22

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
agggtctctg gtctactgat g                                             21

<210> SEQ ID NO 263
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
tttggattta ccgcttggg                                                19

<210> SEQ ID NO 264
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
gactccagtg tgggagag                                                 18

<210> SEQ ID NO 265
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
gggcccacat ataaatcctc ac                                            22

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
ctgctggtca ctgttctcat c                                             21

<210> SEQ ID NO 267
<211> LENGTH: 17
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 267
cttcgcggtg tggtgaa                                                  17

<210> SEQ ID NO 268
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
gctgtgtctc ccgtcaaa                                                 18

<210> SEQ ID NO 269
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
ctgggacaca ttgccttct                                                19

<210> SEQ ID NO 270
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
ccaccatgca ttctttcaat tct                                           23

<210> SEQ ID NO 271
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
aaacccagtt tgaggagatg ag                                            22

<210> SEQ ID NO 272
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
ccctgccaat atcttgggta at                                            22

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
acagcaactt ccttgatccc                        20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
gcggcatcac tgtctatgaa                        20

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
ccttgccttc tcttaggctt t                      21

<210> SEQ ID NO 276
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
agcagtggtt tcagcatca                         19

<210> SEQ ID NO 277
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
cagataactc tcattcagta ttcttgg                27

<210> SEQ ID NO 278
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
ctctaatgta gcttgacctc atct                   24

<210> SEQ ID NO 279
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
gagaagttgg acaagattgg g                                          21

<210> SEQ ID NO 280
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
gctgagaagt tctgtgaatt cttta                                      25

<210> SEQ ID NO 281
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
gtttcctcaa ccagtcacat aga                                        23

<210> SEQ ID NO 282
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
agttgtctag cagtttccac ata                                        23

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
gggaaagcct gtctgaagtg                                            20

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
tcgtagcctc cagggtaata g                                          21

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
gttacaggtc tcctatctac agc                                        23

<210> SEQ ID NO 286
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
gctcagcctc tctggaag                                                 18

<210> SEQ ID NO 287
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
ctctcttacc ctgattcgga tg                                            22

<210> SEQ ID NO 288
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
ggcgtctgcc tgtgatt                                                  17

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
cctgagttct ggtgccaaag                                               20

<210> SEQ ID NO 290
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
gggcatgagc agcttcaa                                                 18

<210> SEQ ID NO 291
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
ccactggctt ggtggattt                                                19

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 292
tcaacagaaa tgcccagagt t           21

<210> SEQ ID NO 293
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 293
cttctccagc tgggcatt           18

<210> SEQ ID NO 294
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 294
tgctgtggca gcagatg           17

<210> SEQ ID NO 295
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 295
cggtcatgtc cgccttc           17

<210> SEQ ID NO 296
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 296
gcgtttccat tatgtcgttg tc           22

<210> SEQ ID NO 297
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 297
ccctccttct aggatagcg           19

-continued

```
<210> SEQ ID NO 298
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
aacccggaat gggtgat                                                      17

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
aaacggactg atgtcactgg                                                   20

<210> SEQ ID NO 300
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
tggacagaag acatactcat aaagg                                             25

<210> SEQ ID NO 301
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
cccactgctt caggaaacat a                                                 21

<210> SEQ ID NO 302
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
gtcagacatc ttccctccat tc                                                22

<210> SEQ ID NO 303
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
gccgcactga cagtatga                                                     18

<210> SEQ ID NO 304
```

<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
cagaaggagc aggactgaaa                                              20

<210> SEQ ID NO 305
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
agcggcgcct cttatatc                                                18

<210> SEQ ID NO 306
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
gcgttgaaag agaagacaaa ct                                           22

<210> SEQ ID NO 307
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
ctactgcaac ggcaacct                                                18

<210> SEQ ID NO 308
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
gggccatgtt cttgctca                                                18

<210> SEQ ID NO 309
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
cagactcgct cgctcattt                                               19

<210> SEQ ID NO 310
<211> LENGTH: 19

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
cctccatgcc cactttctt                                                 19

<210> SEQ ID NO 311
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
cccaagtcag tacgtccaaa t                                              21

<210> SEQ ID NO 312
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
gcctaattcc cgaataacat caac                                           24

<210> SEQ ID NO 313
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
gctttaaaga aagtgtttgc tg                                             22

<210> SEQ ID NO 314
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
ctgtatctgc aggttcgtaa g                                              21

<210> SEQ ID NO 315
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
aagttccccg tgtgcatc                                                  18

<210> SEQ ID NO 316
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 316
ctcagcctcc tcgatgaa                                                 18

<210> SEQ ID NO 317
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
gtgaggaggc aaggttctg                                                19

<210> SEQ ID NO 318
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
ggctccagag agggtagtt                                                19

<210> SEQ ID NO 319
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
tttggattta ccgcttggg                                                19

<210> SEQ ID NO 320
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
gactccagtg tgggagag                                                 18

<210> SEQ ID NO 321
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
cttcgcggtg tggtgaa                                                  17

<210> SEQ ID NO 322
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 322
gctgtgtctc ccgtcaaa                                                   18

<210> SEQ ID NO 323
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
atcctgctgt atcacatcat g                                               21

<210> SEQ ID NO 324
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
ctgacaggtt tcaaagaacc t                                               21

<210> SEQ ID NO 325
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
ccagtgcctt tggttgct                                                   18

<210> SEQ ID NO 326
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
caagagccag atgggcaag                                                  19

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
tgccaagaga agatgctcac                                                 20

<210> SEQ ID NO 328
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 328
cattgagtgc aacatgaag ac                                           22

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
aagaagctgc caatagggat                                             20

<210> SEQ ID NO 330
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
tgtccagaga ggtggatg                                               18

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
tcaatgagaa gcaccttggc                                             20

<210> SEQ ID NO 332
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
atcagcagag tcaatcagtg ag                                          22

<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
gtcttcaggc tcaaacaggt                                             20

<210> SEQ ID NO 334
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
                        primer

<400> SEQUENCE: 334
tctccaaact tcttcctcat tcc                                              23

<210> SEQ ID NO 335
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
gtgtgctgga cgctgga                                                     17

<210> SEQ ID NO 336
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
ctgtacggaa tgcgtttctt g                                                21

<210> SEQ ID NO 337
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
caattcagtc ttcagcaact tgag                                             24

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
tgttccaaag ctcctcacaa                                                  20

<210> SEQ ID NO 339
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
cccaacccag gcatgatg                                                    18

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 340
gatccttatg ccatcaccgt                                          20

<210> SEQ ID NO 341
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
gctgtgtaca gtcatggatg g                                        21

<210> SEQ ID NO 342
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
catgttgcct acagcctct                                           19

<210> SEQ ID NO 343
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
gtgatacctt gaagcacacc attac                                    25

<210> SEQ ID NO 344
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
cagccagatg tgttgcca                                            18

<210> SEQ ID NO 345
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
ctgacagtta gagccgatat cac                                      23

<210> SEQ ID NO 346
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 346
caatgtgata ggtactctca gagg                                              24

<210> SEQ ID NO 347
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 347
acccggaaac cagcagagct                                                   20

<210> SEQ ID NO 348
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 348
tcttgtcagc agcgttcccg g                                                 21

<210> SEQ ID NO 349
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 349
tggctattct tctttaggca atgggca                                           27

<210> SEQ ID NO 350
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 350
acatggctta tcagcaggtt catgca                                            26

<210> SEQ ID NO 351
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 351
aaagcacctg ctcgggtgat tct                                               23

<210> SEQ ID NO 352
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 352
```
cagcatttgc agactccagc gg                                           22

<210> SEQ ID NO 353
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 353
atgcttacga acctgcagat acagctc                                      27

<210> SEQ ID NO 354
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 354
atgaacaaca gctgctccac tctga                                        25

<210> SEQ ID NO 355
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 355
aacctgcaga tacagctc                                                18

<210> SEQ ID NO 356
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 356
cctttctcct gatggcc                                                 17

<210> SEQ ID NO 357
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 357
gtccaagaga gctcagtct                                               19

<210> SEQ ID NO 358
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 358
caaagtaccc gcactg                                                    16

<210> SEQ ID NO 359
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 359
ccaaggtcca agcct                                                     15

<210> SEQ ID NO 360
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 360
cagcgttccc gg                                                        12

<210> SEQ ID NO 361
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 361
atacccattg tcatcgc                                                   17

<210> SEQ ID NO 362
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 362
atcacagagg gagacc                                                    16

<210> SEQ ID NO 363
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 363
ctgtgctgga caatg                                                     15

<210> SEQ ID NO 364
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 364
cctgggcacg atgc                                                      14

<210> SEQ ID NO 365
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 365
actcctctga ccacacc                                                17

<210> SEQ ID NO 366
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 366
tgcaagttat caagaagttt tgtaagtt                                    28

<210> SEQ ID NO 367
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 367
atgctgtatt ttgcac                                                 16

<210> SEQ ID NO 368
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 368
ttttaaccac catgcattct ttc                                         23

<210> SEQ ID NO 369
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 369
ggttctctgc ctg                                                    13

<210> SEQ ID NO 370
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 370
gaggtcctga ggc                                                    13

<210> SEQ ID NO 371
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 371
tgctgatggt cctca                                                    15

<210> SEQ ID NO 372
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 372
gagccaaacg cc                                                       12

<210> SEQ ID NO 373
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 373
cccaggtggt cca                                                      13

<210> SEQ ID NO 374
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 374
cggtggcatt gg                                                       12

<210> SEQ ID NO 375
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 375
ggacaacgac cttt                                                     14

<210> SEQ ID NO 376
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 376
gccaccccac tc                                                       12

<210> SEQ ID NO 377
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 377
cccaatgata aggagg                                                          16

<210> SEQ ID NO 378
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
ctgacagtta gagccgatat cac                                                  23

<210> SEQ ID NO 379
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
caattcagtc ttcagcaact tgag                                                 24

<210> SEQ ID NO 380
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
gtttgtcctc ctcaatctgg t                                                    21

<210> SEQ ID NO 381
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
gtgatatcgg ctctaactgt cag                                                  23

<210> SEQ ID NO 382
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 382
tcagcagcct ctctcca                                                         17

<210> SEQ ID NO 383

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 383
gggcaagatt tgaattcgat ca                                            22

<210> SEQ ID NO 384
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 384
gctacagcga cgtgaagaag                                               20

<210> SEQ ID NO 385
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
gacctcggta cctggaca                                                 18

<210> SEQ ID NO 386
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 386
tcgatgtggc cctggag                                                  17

<210> SEQ ID NO 387
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 387
ttccgctcat cttgctcag                                                19

<210> SEQ ID NO 388
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 388
atcagcagag tcaatcagtg ag                                            22

<210> SEQ ID NO 389
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 389
gatccttatg ccatcaccgt                                                   20

<210> SEQ ID NO 390
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 390
agctccttcc agtccgaat                                                    19

<210> SEQ ID NO 391
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 391
gtctgctcat caatcacctc a                                                 21

<210> SEQ ID NO 392
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
tcctccactc atctccaact                                                   20

<210> SEQ ID NO 393
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
cctggatgct gacatttctg a                                                 21

<210> SEQ ID NO 394
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
ggacagagag aacaaggatg aac                                               23

<210> SEQ ID NO 395
<211> LENGTH: 23
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 395
tgtgggagaa tataggtgga ttg                                          23

<210> SEQ ID NO 396
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
ggattaagtt cataagattc catgct                                       26

<210> SEQ ID NO 397
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
cttcggcttt gatatcgttt cag                                          23

<210> SEQ ID NO 398
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398
gacaacaacc accttcaata cac                                          23

<210> SEQ ID NO 399
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
agatccagga ccgatggtt                                               19

<210> SEQ ID NO 400
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 400
ggactggata aatgtattca agca                                         24

<210> SEQ ID NO 401
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
ggcaattggt ttgaggcaa                                                19

<210> SEQ ID NO 402
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 402
ggtgtttggt ctaggatgga g                                             21

<210> SEQ ID NO 403
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 403
actgggtttg acttcgtagc                                               20

<210> SEQ ID NO 404
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 404
cagtgcttgc agttcaaaca g                                             21

<210> SEQ ID NO 405
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405
ccagtagaag gttttggat tgtc                                           24

<210> SEQ ID NO 406
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 406
tcatttggac gtactgactt gg                                            22

<210> SEQ ID NO 407
<211> LENGTH: 19
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 407
cttgctccag ctcctgttc                                                 19

<210> SEQ ID NO 408
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408
gcaacaagtg actgagacct a                                              21

<210> SEQ ID NO 409
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 409
gtccacacac tcatgctgat                                                20

<210> SEQ ID NO 410
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410
gtcttttcaa ccatgtcctc ca                                             22

<210> SEQ ID NO 411
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
acttccttga tccctgcca                                                 19

<210> SEQ ID NO 412
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 412
actctgaaaa actttggact gatg                                           24

<210> SEQ ID NO 413
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 413
tctagcaatc aacagatgag ttct                                              24

<210> SEQ ID NO 414
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 414
cctcaaatac atcaagcaca gc                                                22

<210> SEQ ID NO 415
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 415
ggaagccttc accagcaa                                                     18

<210> SEQ ID NO 416
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 416
gagatgctta agtgtgacaa gttc                                              24

<210> SEQ ID NO 417
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417
cctcagattt caactcgttg tc                                                22

<210> SEQ ID NO 418
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 418
ttgcaggctt cacatacctt                                                   20

<210> SEQ ID NO 419
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 419
gcccgacatg cttgagt                                                    17

<210> SEQ ID NO 420
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 420
atcttccctc cattctgctt c                                               21

<210> SEQ ID NO 421
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
cagttcccac tcactttctc ag                                              22

<210> SEQ ID NO 422
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 422
ccgacaacct caagtgctg                                                  19

<210> SEQ ID NO 423
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423
gctggggaaa gttaatgttc ac                                              22
```